(12) United States Patent
Landers et al.

(10) Patent No.: US 6,703,228 B1
(45) Date of Patent: Mar. 9, 2004

(54) METHODS AND PRODUCTS RELATED TO GENOTYPING AND DNA ANALYSIS

(75) Inventors: John Landers, Watertown, MA (US); Barbara Jordan, Libertyville, IL (US); David E. Housman, Newton, MA (US); Alain Charest, Chelsea, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/404,912

(22) Filed: Sep. 24, 1999

Related U.S. Application Data

(60) Provisional application No. 60/101,757, filed on Sep. 25, 1998.

(51) Int. Cl.⁷ .......................... C12Q 1/68; C12P 19/34; C07H 21/04; G01N 33/48

(52) U.S. Cl. .................. 435/91.2; 435/6; 536/24.3; 536/24.31; 536/24.32; 536/24.33; 702/19; 702/20

(58) Field of Search .................. 702/19, 20; 435/320.1, 435/325, 252.3, 6, 91.2; 536/23.1, 24.1, 24.3, 24.31, 24.32, 24.33

(56) References Cited

U.S. PATENT DOCUMENTS

| | | |
|---|---|---|
| 4,588,682 A | 5/1986 | Groet et al. |
| 4,829,098 A | 5/1989 | Hoffman et al. |
| 4,946,980 A | 8/1990 | Halm et al. |
| 4,963,663 A | 10/1990 | White et al. |
| 5,032,502 A | 7/1991 | Stodolsky |
| 5,034,428 A | 7/1991 | Hoffman et al. |
| 5,043,272 A | 8/1991 | Hartley |
| 5,104,792 A | 4/1992 | Silver et al. |
| 5,106,727 A | 4/1992 | Hartely et al. |
| 5,126,239 A | 6/1992 | Livak et al. |
| 5,220,004 A | 6/1993 | Saiki et al. |
| 5,445,934 A | 8/1995 | Fodor et al. |
| 5,468,613 A | 11/1995 | Erlich et al. |
| 5,487,985 A | 1/1996 | McClelland et al. |
| 5,510,084 A | 4/1996 | Cros et al. |
| 5,518,900 A | 5/1996 | Nikiforov et al. |
| 5,545,527 A | 8/1996 | Stevens et al. ................ 435/6 |
| 5,565,322 A | 10/1996 | Heller |
| 5,576,180 A | 11/1996 | Melanon et al. |
| 5,578,443 A | 11/1996 | Santamaria et al. |
| 5,578,458 A | 11/1996 | Caskey et al. |
| 5,582,989 A | 12/1996 | Caskey et al. |
| 5,589,330 A | 12/1996 | Shuber |
| 5,597,694 A | 1/1997 | Munroe et al. |
| 5,599,674 A | 2/1997 | Pena et al. |
| 5,599,921 A | 2/1997 | Sorge et al. |
| 5,604,097 A | 2/1997 | Brenner |
| 5,604,099 A | 2/1997 | Erlich et al. |
| 5,605,662 A | 2/1997 | Heller et al. |
| 5,610,287 A | 3/1997 | Nikiforov et al. |
| 5,612,179 A | 3/1997 | Simons ........................ 435/6 |
| 5,632,957 A | 5/1997 | Heller et al. |
| 5,633,134 A | 5/1997 | Shuber |
| 5,639,611 A | 6/1997 | Wallace et al. |
| 5,663,062 A | 9/1997 | Sorge et al. |
| 5,667,972 A | 9/1997 | Drmanac et al. |
| 5,667,976 A | 9/1997 | Van Ness et al. |
| 5,679,524 A | 10/1997 | Nikiforov et al. |
| 5,683,872 A | 11/1997 | Rudert et al. |
| 5,695,933 A | 12/1997 | Schalling et al. |
| 5,702,890 A | 12/1997 | Housman |
| 5,707,806 A | 1/1998 | Shuber ......................... 435/6 |
| 5,710,000 A | 1/1998 | Sapolsky et al. |
| 5,721,098 A | 2/1998 | Pinkel et al. |
| 5,728,524 A | 3/1998 | Sibson |
| 5,728,530 A | 3/1998 | Rust et al. .................... 435/6 |
| 5,731,171 A | 3/1998 | Bohlander |

(List continued on next page.)

FOREIGN PATENT DOCUMENTS

| | | | |
|---|---|---|---|
| EP | 0 534 858 A1 | 3/1993 | |
| EP | 0950720 A1 | 10/1999 | ............ C12Q/1/68 |
| WO | WO95/12607 | 5/1995 | |
| WO | WO96/17082 | 6/1996 | |
| WO | WO96/17957 | 6/1996 | |
| WO | WO96/38591 | 12/1996 | |
| WO | WO97/12030 | 4/1997 | |
| WO | WO97/29212 | 8/1997 | |
| WO | WO97/31327 A | 8/1997 | |
| WO | WO97/39151 | 10/1997 | |
| WO | WO97/43450 | 11/1997 | |
| WO | WO98/12354 | 3/1998 | |
| WO | WO9818967 | 5/1998 | |
| WO | WO98/20165 A | 5/1998 | |
| WO | WO98/24796 | 6/1998 | |
| WO | WO98/30883 | 7/1998 | |
| WO | WO98/31836 | 7/1998 | |
| WO | WO 99/01576 | 1/1999 | ............ C12Q/1/68 |
| WO | WO 00/24939 | 5/2000 | ............ C12Q/1/68 |
| WO | 1001037 A2 | 5/2000 | ............ C12Q/1/68 |

OTHER PUBLICATIONS

Himmelbauer et al., Mammalian Genome, vol. 9, pp. 611–616, 1998.*

Telenius et al., Genomics, vol. 13, pp. 718–725, 1992.*

(List continued on next page.)

*Primary Examiner*—John S. Brusca
*Assistant Examiner*—Shubo "Joe" Zhou
(74) *Attorney, Agent, or Firm*—Wolf, Greenfield and Sacks, P.C.

(57) ABSTRACT

The invention encompasses methods and products related to genotyping. The method of genotyping of the invention is based on the use of single nucleotide polymorphisms (SNPs) to perform high throughput genome scans. The high throughput method can be performed by hybridizing SNP allele-specific oligonucleotides and a reduced complexity genome (RCG). The invention also relates to methods of preparing the SNP specific oligonucleotides and RCGs, methods of fingerprinting, determining allele frequency for a SNP, characterizing tumors, generating a genomic classification code for a genome, identifying previously unknown SNPs, and related compositions and kits.

40 Claims, 9 Drawing Sheets

U.S. PATENT DOCUMENTS

| | | | |
|---|---|---|---|
| 5,738,993 | A | 4/1998 | Fugono et al. |
| 5,741,678 | A | 4/1998 | Ronai |
| 5,744,305 | A | 4/1998 | Fodor et al. |
| 5,759,821 | A | 6/1998 | Teasdale |
| 5,760,130 | A | 6/1998 | Johnston et al. |
| 5,762,876 | A | 6/1998 | Lincoln et al. |
| 5,787,032 | A | 7/1998 | Heller et al. |
| 5,789,168 | A | 8/1998 | Leushner et al. |
| 5,795,722 | A | 8/1998 | Lacroix et al. |
| 5,811,239 | A | 9/1998 | Frayne |
| 5,814,444 | A | 9/1998 | Rabinovitch |
| 5,817,007 | A | 10/1998 | Fodgaard et al. |
| 5,834,181 | A | 11/1998 | Shuber ................ 435/5 |
| 5,834,189 | A | 11/1998 | Stevens et al. |
| 5,849,483 | A | 12/1998 | Shuber ................ 435/5 |
| 5,856,104 | A | 1/1999 | Chee et al. |
| 5,858,659 | A | 1/1999 | Sapolsky et al. |
| 5,861,245 | A | 1/1999 | McClelland et al. |
| 5,866,337 | A | 2/1999 | Schon |
| 5,869,237 | A | 2/1999 | Ward et al. |
| 5,885,775 | A | 3/1999 | Haff et al. |
| 5,888,778 | A | 3/1999 | Shuber |
| 5,908,978 | A | 6/1999 | Amerson et al. |
| 5,910,576 | A | * 6/1999 | Bertina et al. ......... 530/388 |
| 5,919,626 | A | 7/1999 | Shi et al. |
| 5,942,392 | A | 8/1999 | Amouyel et al. |
| 5,945,283 | A | 8/1999 | Kwok et al. |
| 5,945,675 | A | 8/1999 | Malins |
| 5,946,431 | A | 8/1999 | Fernandes |
| 5,981,176 | A | 11/1999 | Wallace ................ 435/6 |
| 5,994,056 | A | 11/1999 | Higuchi ................ 435/6 |
| 6,013,431 | A | 1/2000 | Söderlund et al. ......... 435/5 |
| 6,015,675 | A | 1/2000 | Caskey et al. ............ 435/6 |
| 6,027,889 | A | 2/2000 | Barany et al. ............ 435/6 |
| 6,037,124 | A | 3/2000 | Matson ................ 435/6 |
| 6,048,689 | A | 4/2000 | Murphy et al. ............ 435/6 |
| 6,083,763 | A | 7/2000 | Balch ................ 436/518 |
| 6,100,030 | A | 8/2000 | McCasky Feazel et al. .... 435/6 |
| 6,383,742 | B1 | * 5/2002 | Drmanac et al. ........... 435/6 |

OTHER PUBLICATIONS

Beltinger, C.P. et al., "Whole Genome Amplification of Single Cells From Clinical Peripheral Blood Smears," *J. Clin. Pathol: Mol. Pathol.* 50:272 (1997).

Cheung, V.G. et al., "Whole Genome Amplification Using a Degenerate Oligonucleotide Primer Allows Hundreds of Genotypes to be Genotypes to be Performed on Less Than One Nanagram of Genomic DNA," *Proc. Natl. Acad. Sci. USA* 93:14676 (1996).

Paunio, T. et al., "Preimplantation Diagnosis by Whole–Genome Amplification, PCR Amplification, and Solid–Phase Minisequencing of Blastomere DNA," *Clin. Chem.* 42(9):1382 (1996).

Snabes, M.C. et al., "Preimplantation Single–Cell Analysis of Multiple Genetic Loci by Whole–Genome Amplication," *Proc. Natl. Acad. Sci. USA* 91:6181 (1994).

Center for Medical Genetics: Marshfield Medical Research Foundation, "Genotyping Statistics", (1998).

Cheung, et al., "Whole genome amplification using a degenerate oligonucleotide primer allows hundreds of genotypes to be performed on less than one nanogram of genomic DNA", Proc. Natl. Acad. Sci. USA, vol. 93, pp. 14676–14679 (1996).

Delahunty, et al. "Testing the feasibility of DNA typing human identification by PCR and an oligonucleotide ligation assay", Am. J. Hum, Genet., 58, pp. 1239–1246 (1996).

Elango, et al., "Generation and mapping of Mus spretus strain–specific markers for rapid genomic scanning" Mammalian Genome 7, pp. 340–343 (1996).

Gilles, et al., "Single nucleotide polymorphic discrimination by an electronic dot blot assay on semiconductor microchips" Nature Biotechnology vol. 17, pp. 365–370 (1999).

Howell, et al., "Dynamic allele–specific hybridization: A new method for scoring single nucleotide polymorphisms", Nature Biotechnology, vol. 17, pp. 87–88 (1999).

Ledbetter, et al., "Rapid isolation of DNA probes within specific chromosome regions by interspersed repetitive sequence polymerase chain reaction" Genomics 6, pp. 475–481 (1990).

Hunter, et al., "Toward the construction of integrated physical and genetic maps of the mouse genome using interspersed repetitive sequence PCR (IRS–PCR) genomics", Genome Research, 6, pp. 290–299 (1996 ).

McCarthy, et al., "Efficient high–resolution genetic mapping of mouse interspersed repetitive sequence PCR products, toward integrated genetic and physical mapping of the mouse genome", Proc. Natl. Acad. Sci. USA, vol. 92, pp. 5302–5306 (1995).

Risch, et al., "The future of genetic studies of complex human diseases", Science, vol. 273, pp. 1516–1517 (1996).

Sinnett, et al., "Alumorphs–Human DNA polymorphisms detected by polymerase chain reaction using alu–specific primers", Genomics 7, pp. 331–334 (1990).

Telenius, et al., "Degenerate oligonucleotide–primed PCR: General amplification of target DNA by a single degenerate primer", Genomics 13, pp. 718–725 (1992).

Vos, et al., "AFLP: a new technique for DNA fingerprinting", Nucleic Acids Research, vol. 23, No. 21 pp. 4407–4414 (1995).

Wang, et al., Large–scale identification, mapping, and genotyping of single–nucleotide polymorphisms in the human genome, Science, 280:1077–1082 (1998).

Welsh, et al., "Fingerprinting genomes using PCR with arbitrary primers", Nucleic Acids Research, vol. 18, No. 24, pp. 7213–7218 (1990).

Zietkiewicz, et al., "Linkage mapping by simultaneous screening of multiple polymorphic loci using Alu oligonucleotide–directed PCR", Proc. Natl. Acad. Sci. USA vol. 89, pp. 8448–8451 (1992).

Winzler, et al., "Direct allelic variatio scanning of the yeast genom", Science vol. 281, pp. 1194–1197 (1998).

Armstrong et al., "Suspension Arrays for High Throughput, Multiplexed Single Nucleotide Polymorphism Genotyping", *Cytometry* 40:102–108 (2000).

Cronin et al., "Applying rapid DNA microarray optimization capability to SNP screening and genotyping", *American Journal of Human Genetics*, 65(4):pA224, Oct. 1999, No. 1238.

Griffin et al., "Direct genetic analysis by matrix–assisted laser desorption/ionization mass spectrometry", *Proc. Natl. Acad. Sci. USA*, vol. 96, pp. 6301–6306, May 1999, Genetics.

Holloway et al., "Comparison of Three Methods for Single Nucleotide Polymorphism Typing for DNA Bank Studies: Sequence–Specific Oligonucleotide Probe Hybridisation, TagMan Liquid Phase Hybridisation, and Microplate Array Diagonal Gel Electrophoresis (MADGE)", *Human Mutation*, 14:340–347 (1999).

Iannone et al., "Multiplexed Single Nucleotide Polymorphism Genotyping by Oligonucleotide Ligation and Flow Cytometry", *Cytometry*, 39:131–140, (2000).

Ruano et al., "Haplotype of multiple polymorphism resolved by enzymatic amplification of single DNA molecules", *Proc. Natl. Acad. Sci. USA*, vol. 87, pp. 6296–6300, Aug. 1990, *Genetics*.

Sauer et al., "A novel procedure for efficient genotyping of single nucleotide polymorphisms", *Nucleic Acids Research*, 2000, vol. 28, No. 5, E13–e13, Oxford University Press.

Toh et al., "Large–scale discovery and genotyping of single–nucleotide polymorphisms in the mouse", Nature Genetics, vol. 24, pp. 381–386, Apr. 2000.

Broude, et al., "Differential Display of Genome Subsets Containing Specific Interspersed Repeats" *PNAS*, 94: 4548–4553, (Apr. 1997).

Cheng et al., "Degenerate Oligonucleotide Primer–Polymerase Chain Reaction And Capillary Electrophoretic Analysis of Human DNA on Microchip–Based Devices", *Anal. Biochem.*, 257:101–106 (Mar. 1998).

Himmelbauer, et al., "Complex Probes for High–Throughput Parallel Genetic Mapping of Genomic Mouse Bac Clones", *Mammalian Genome*, 9:611–616 (Aug. 1998).

Kruglyak, L, "The Use of A Genetic Map of Biallelic Markers In Linkage Studies" *Nature Genetics*, 17(1):22–24 (Sep. 1, 1997).

Xiong M., et al., "Biallelic Markers In Genetics Studies of Human Diseases . . . ", *American Journal of Human Genetics*, 61(4):1759, 1999.

Wang, D. et al., "Large–Scale Identification, Mapping, and Genotyping . . . ", *Science, US, Am. Assoc. For the Advancement of Science*, 280 (280):1077–1082 (May 1998).

* cited by examiner

REDUCE GENOME COMPLEXITY
BY INTER-ALU PCR

ALU ALU ALU
PCR PCR PCR

MINILIBRARIES OF
CLONED ALU PCR PRODUCTS

MATCH CLONES BY HYBRIDIZATION

DIRECT SEQUENCE COMPARISON
GATC
GATC
GACC    SNP
GATC
GACC
GACC

SEQUENCE LISTING

```
<160> NUMBER OF SEQ ID NOS: 691

<210> SEQ ID NO 1
<211> LENGTH: 9
<212> TYPE: DNA
<213> ORGANISM: Homo Sapiens
<220> FEATURE:
<221> NAME/KEY: variation
<222> LOCATION: (4)...(6)
<223> OTHER INFORMATION: N = A, C, G or T

<400> SEQUENCE: 1 cagnnnctg                                                            9

<210> SEQ ID NO 2
<211> LENGTH: 13
<212> TYPE: DNA
<213> ORGANISM: Homo Sapiens

<400> SEQUENCE: 2
tttttttttt cag                                                      13

<210> SEQ ID NO 3
<211> LENGTH: 19
<212> TYPE: DNA
<213> ORGANISM: Homo Sapiens

<400> SEQUENCE: 3
cttgcagtga gccgagatc                                                19

<210> SEQ ID NO 4
<211> LENGTH: 20
<212> TYPE: DNA
<213> ORGANISM: Homo Sapiens
<220> FEATURE:
<221> NAME/KEY: variation
<222> LOCATION: (7)...(12)
```

<223> OTHER INFORMATION: N = A, C, G or T

<400> SEQUENCE: 4
ctcgagnnnn nnaagcgatg                                              20

<210> SEQ ID NO 5
<211> LENGTH: 11
<212> TYPE: DNA
<213> ORGANISM: Homo Sapiens

<400> SEQUENCE: 5
taagtgtaca a                                                       11

<210> SEQ ID NO 6
<211> LENGTH: 11
<212> TYPE: DNA
<213> ORGANISM: Homo Sapiens

<400> SEQUENCE: 6
taagtataca a                                                       11

<210> SEQ ID NO 7
<211> LENGTH: 11
<212> TYPE: DNA
<213> ORGANISM: Homo Sapiens

<400> SEQUENCE: 7
cccacggaga a                                                       11

<210> SEQ ID NO 8
<211> LENGTH: 11
<212> TYPE: DNA
<213> ORGANISM: Homo Sapiens

<400> SEQUENCE: 8
cccacagaga a                                                       11

<210> SEQ ID NO 9
<211> LENGTH: 11
<212> TYPE: DNA
<213> ORGANISM: Homo Sapiens

<400> SEQUENCE: 9
aattgcttcc c                                                       11

<210> SEQ ID NO 10
<211> LENGTH: 11
<212> TYPE: DNA
<213> ORGANISM: Homo Sapiens

<400> SEQUENCE: 10
aattgtttcc c                                                       11

<210> SEQ ID NO 11
<211> LENGTH: 11
<212> TYPE: DNA
<213> ORGANISM: Homo Sapiens

<400> SEQUENCE: 11
aaattcaatg t                                                       11

<210> SEQ ID NO 12
<211> LENGTH: 11

-continued

```
<212> TYPE: DNA
<213> ORGANISM: Homo Sapiens

<400> SEQUENCE: 12
aaattaaatg t                                                           11

<210> SEQ ID NO 13
<211> LENGTH: 24
<212> TYPE: DNA
<213> ORGANISM: Homo Sapiens

<400> SEQUENCE: 13
attaaaggcg tgcgccacca tgcc                                             24

<210> SEQ ID NO 14
<211> LENGTH: 18
<212> TYPE: DNA
<213> ORGANISM: Homo Sapiens

<400> SEQUENCE: 14
tttatgaagg cataaaaa                                                    18

<210> SEQ ID NO 15
<211> LENGTH: 18
<212> TYPE: DNA
<213> ORGANISM: Homo Sapiens

<400> SEQUENCE: 15
tttatggagg cataaaaa                                                    18

<210> SEQ ID NO 16
<211> LENGTH: 18
<212> TYPE: DNA
<213> ORGANISM: Homo Sapiens

<400> SEQUENCE: 16
tttatgaagg tataaaaa                                                    18

<210> SEQ ID NO 17
<211> LENGTH: 17
<212> TYPE: DNA
<213> ORGANISM: Homo Sapiens

<400> SEQUENCE: 17
ctgggctgta ttcattt                                                     17

<210> SEQ ID NO 18
<211> LENGTH: 17
<212> TYPE: DNA
<213> ORGANISM: Homo Sapiens

<400> SEQUENCE: 18
ctgggctgca ttcattt                                                     17

<210> SEQ ID NO 19
<211> LENGTH: 17
<212> TYPE: DNA
<213> ORGANISM: Homo Sapiens

<400> SEQUENCE: 19
tctgcctcct gagtgct                                                     17

<210> SEQ ID NO 20
```

-continued

```
<211> LENGTH: 17
<212> TYPE: DNA
<213> ORGANISM: Homo Sapiens

<400> SEQUENCE: 20
tctacctccc aagtgct                                                  17

<210> SEQ ID NO 21
<211> LENGTH: 17
<212> TYPE: DNA
<213> ORGANISM: Homo Sapiens

<400> SEQUENCE: 21
tagctagaat caagctt                                                  17

<210> SEQ ID NO 22
<211> LENGTH: 17
<212> TYPE: DNA
<213> ORGANISM: Homo Sapiens

<400> SEQUENCE: 22
tagctagagt caagctt                                                  17

<210> SEQ ID NO 23
<211> LENGTH: 17
<212> TYPE: DNA
<213> ORGANISM: Homo Sapiens

<400> SEQUENCE: 23
gctgtgcaac aaatcac                                                  17

<210> SEQ ID NO 24
<211> LENGTH: 17
<212> TYPE: DNA
<213> ORGANISM: Homo Sapiens

<400> SEQUENCE: 24
cagctgtgca aatcacc                                                  17

<210> SEQ ID NO 25
<211> LENGTH: 17
<212> TYPE: DNA
<213> ORGANISM: Homo Sapiens

<400> SEQUENCE: 25
tttcgtgatg tttctat                                                  17

<210> SEQ ID NO 26
<211> LENGTH: 17
<212> TYPE: DNA
<213> ORGANISM: Homo Sapiens

<400> SEQUENCE: 26
tttcgtgaat gtttcta                                                  17

<210> SEQ ID NO 27
<211> LENGTH: 17
<212> TYPE: DNA
<213> ORGANISM: Homo Sapiens

<400> SEQUENCE: 27
cactgtctac atcttta                                                  17
```

-continued

```
<210> SEQ ID NO 28
<211> LENGTH: 17
<212> TYPE: DNA
<213> ORGANISM: Homo Sapiens

<400> SEQUENCE: 28
cactgtctcc atcttta                                                    17

<210> SEQ ID NO 29
<211> LENGTH: 17
<212> TYPE: DNA
<213> ORGANISM: Homo Sapiens

<400> SEQUENCE: 29
taacattctt gaagcca                                                    17

<210> SEQ ID NO 30
<211> LENGTH: 17
<212> TYPE: DNA
<213> ORGANISM: Homo Sapiens

<400> SEQUENCE: 30
taacattcct gaagcca                                                    17

<210> SEQ ID NO 31
<211> LENGTH: 17
<212> TYPE: DNA
<213> ORGANISM: Homo Sapiens

<400> SEQUENCE: 31
gcttccattt cctaagg                                                    17

<210> SEQ ID NO 32
<211> LENGTH: 17
<212> TYPE: DNA
<213> ORGANISM: Homo Sapiens

<400> SEQUENCE: 32
gcttccactt cctaagg                                                    17

<210> SEQ ID NO 33
<211> LENGTH: 17
<212> TYPE: DNA
<213> ORGANISM: Homo Sapiens

<400> SEQUENCE: 33
aggaatggca ataatcc                                                    17

<210> SEQ ID NO 34
<211> LENGTH: 17
<212> TYPE: DNA
<213> ORGANISM: Homo Sapiens

<400> SEQUENCE: 34
aggaatggcg ataatcc                                                    17

<210> SEQ ID NO 35
<211> LENGTH: 17
<212> TYPE: DNA
<213> ORGANISM: Homo Sapiens

<400> SEQUENCE: 35
aggaatgaca ataatcc                                                    17
```

<210> SEQ ID NO 36
<211> LENGTH: 17
<212> TYPE: DNA
<213> ORGANISM: Homo Sapiens

<400> SEQUENCE: 36
ttaaattcgt aaatgga                                                17

<210> SEQ ID NO 37
<211> LENGTH: 17
<212> TYPE: DNA
<213> ORGANISM: Homo Sapiens

<400> SEQUENCE: 37
ttaaattcat aaatgga                                                17

<210> SEQ ID NO 38
<211> LENGTH: 17
<212> TYPE: DNA
<213> ORGANISM: Homo Sapiens

<400> SEQUENCE: 38
taacattctt gaagcca                                                17

<210> SEQ ID NO 39
<211> LENGTH: 17
<212> TYPE: DNA
<213> ORGANISM: Homo Sapiens

<400> SEQUENCE: 39
taacattcct gaagcca                                                17

<210> SEQ ID NO 40
<211> LENGTH: 17
<212> TYPE: DNA
<213> ORGANISM: Homo Sapiens

<400> SEQUENCE: 40
ttctgtgact ccacttg                                                17

<210> SEQ ID NO 41
<211> LENGTH: 17
<212> TYPE: DNA
<213> ORGANISM: Homo Sapiens

<400> SEQUENCE: 41
ttctgtgact ccatttg                                                17

<210> SEQ ID NO 42
<211> LENGTH: 17
<212> TYPE: DNA
<213> ORGANISM: Homo Sapiens

<400> SEQUENCE: 42
ttccctgtct ccatttg                                                17

<210> SEQ ID NO 43
<211> LENGTH: 17
<212> TYPE: DNA
<213> ORGANISM: Homo Sapiens

<400> SEQUENCE: 43
gtagtttgcc aggaacc                                                17

-continued

<210> SEQ ID NO 44
<211> LENGTH: 17
<212> TYPE: DNA
<213> ORGANISM: Homo Sapiens

<400> SEQUENCE: 44
gtagtttgtc aggaacc                                                17

<210> SEQ ID NO 45
<211> LENGTH: 19
<212> TYPE: DNA
<213> ORGANISM: Homo Sapiens

<400> SEQUENCE: 45
tgctactcct ctctactcg                                              19

<210> SEQ ID NO 46
<211> LENGTH: 19
<212> TYPE: DNA
<213> ORGANISM: Homo Sapiens

<400> SEQUENCE: 46
tgctattcct ctctgctcg                                              19

<210> SEQ ID NO 47
<211> LENGTH: 19
<212> TYPE: DNA
<213> ORGANISM: Homo Sapiens

<400> SEQUENCE: 47
cttgatcacc ctctgatga                                              19

<210> SEQ ID NO 48
<211> LENGTH: 19
<212> TYPE: DNA
<213> ORGANISM: Homo Sapiens

<400> SEQUENCE: 48
cttggtcacc ctctaatga                                              19

<210> SEQ ID NO 49
<211> LENGTH: 17
<212> TYPE: DNA
<213> ORGANISM: Homo Sapiens

<400> SEQUENCE: 49
gaggtggtgc agagtga                                                17

<210> SEQ ID NO 50
<211> LENGTH: 17
<212> TYPE: DNA
<213> ORGANISM: Homo Sapiens

<400> SEQUENCE: 50
gaggtggcgc agagtga                                                17

<210> SEQ ID NO 51
<211> LENGTH: 17
<212> TYPE: DNA
<213> ORGANISM: Homo Sapiens

<400> SEQUENCE: 51

-continued gaggtggccc agagtga                                                    17

<210> SEQ ID NO 52
<211> LENGTH: 17
<212> TYPE: DNA
<213> ORGANISM: Homo Sapiens

<400> SEQUENCE: 52
cccactgaac cgcacag                                                    17

<210> SEQ ID NO 53
<211> LENGTH: 17
<212> TYPE: DNA
<213> ORGANISM: Homo Sapiens

<400> SEQUENCE: 53
cccactgagc tgcacag                                                    17

<210> SEQ ID NO 54
<211> LENGTH: 17
<212> TYPE: DNA
<213> ORGANISM: Homo Sapiens

<400> SEQUENCE: 54
cccactcagc cgcacag                                                    17

<210> SEQ ID NO 55
<211> LENGTH: 17
<212> TYPE: DNA
<213> ORGANISM: Homo Sapiens

<400> SEQUENCE: 55
tgaagacaca gccagcc                                                    17

<210> SEQ ID NO 56
<211> LENGTH: 17
<212> TYPE: DNA
<213> ORGANISM: Homo Sapiens

<400> SEQUENCE: 56
tgaagacgca gccagcc                                                    17

<210> SEQ ID NO 57
<211> LENGTH: 17
<212> TYPE: DNA
<213> ORGANISM: Homo Sapiens

<400> SEQUENCE: 57
tgaagacgaa gccagcc                                                    17

<210> SEQ ID NO 58
<211> LENGTH: 17
<212> TYPE: DNA
<213> ORGANISM: Homo Sapiens

<400> SEQUENCE: 58
agaagttggt accaggg                                                    17

<210> SEQ ID NO 59
<211> LENGTH: 17
<212> TYPE: DNA
<213> ORGANISM: Homo Sapiens

<400> SEQUENCE: 59

-continued agaagttgtt accaggg                          17

<210> SEQ ID NO 60
<211> LENGTH: 17
<212> TYPE: DNA
<213> ORGANISM: Homo Sapiens

<400> SEQUENCE: 60
tatgattacg taatgtt                          17

<210> SEQ ID NO 61
<211> LENGTH: 17
<212> TYPE: DNA
<213> ORGANISM: Homo Sapiens

<400> SEQUENCE: 61
tatgattatg taatgtt                          17

<210> SEQ ID NO 62
<211> LENGTH: 17
<212> TYPE: DNA
<213> ORGANISM: Homo Sapiens

<400> SEQUENCE: 62
atgattccag tgagtta                          17

<210> SEQ ID NO 63
<211> LENGTH: 17
<212> TYPE: DNA
<213> ORGANISM: Homo Sapiens

<400> SEQUENCE: 63
atgattcctg tgagtta                          17

<210> SEQ ID NO 64
<211> LENGTH: 19
<212> TYPE: DNA
<213> ORGANISM: Homo Sapiens

<400> SEQUENCE: 64
catactatta acactggaa                        19

<210> SEQ ID NO 65
<211> LENGTH: 19
<212> TYPE: DNA
<213> ORGANISM: Homo Sapiens

<400> SEQUENCE: 65
catattatta acacaggaa                        19

<210> SEQ ID NO 66
<211> LENGTH: 17
<212> TYPE: DNA
<213> ORGANISM: Homo Sapiens

<400> SEQUENCE: 66
gtcaagaaca ggcaata                          17

<210> SEQ ID NO 67
<211> LENGTH: 17
<212> TYPE: DNA
<213> ORGANISM: Homo Sapiens -continued

```
<400> SEQUENCE: 67
gtcaagaata ggcaata                                                    17

<210> SEQ ID NO 68
<211> LENGTH: 17
<212> TYPE: DNA
<213> ORGANISM: Homo Sapiens

<400> SEQUENCE: 68
cagactaggg aaccttc                                                    17

<210> SEQ ID NO 69
<211> LENGTH: 17
<212> TYPE: DNA
<213> ORGANISM: Homo Sapiens

<400> SEQUENCE: 69
cagacgaggg aaccttc                                                    17

<210> SEQ ID NO 70
<211> LENGTH: 17
<212> TYPE: DNA
<213> ORGANISM: Homo Sapiens

<400> SEQUENCE: 70
cagactaggg agccttc                                                    17

<210> SEQ ID NO 71
<211> LENGTH: 17
<212> TYPE: DNA
<213> ORGANISM: Homo Sapiens

<400> SEQUENCE: 71
tgtccagttg tttgcat                                                    17

<210> SEQ ID NO 72
<211> LENGTH: 17
<212> TYPE: DNA
<213> ORGANISM: Homo Sapiens

<400> SEQUENCE: 72
tgtccagtcg tttgcat                                                    17

<210> SEQ ID NO 73
<211> LENGTH: 17
<212> TYPE: DNA
<213> ORGANISM: Homo Sapiens

<400> SEQUENCE: 73
ggggtagcca gtttggt                                                    17

<210> SEQ ID NO 74
<211> LENGTH: 17
<212> TYPE: DNA
<213> ORGANISM: Homo Sapiens

<400> SEQUENCE: 74
ggggtagcaa gtttggt                                                    17

<210> SEQ ID NO 75
<211> LENGTH: 17
<212> TYPE: DNA
<213> ORGANISM: Homo Sapiens
```

```
<400> SEQUENCE: 75
caggaagctg tagctcc                                              17

<210> SEQ ID NO 76
<211> LENGTH: 17
<212> TYPE: DNA
<213> ORGANISM: Homo Sapiens

<400> SEQUENCE: 76
caggaagccg tagctcc                                              17

<210> SEQ ID NO 77
<211> LENGTH: 17
<212> TYPE: DNA
<213> ORGANISM: Homo Sapiens

<400> SEQUENCE: 77
cctgagcctg tctacct                                              17

<210> SEQ ID NO 78
<211> LENGTH: 17
<212> TYPE: DNA
<213> ORGANISM: Homo Sapiens

<400> SEQUENCE: 78
cctgagcccg tctacct                                              17

<210> SEQ ID NO 79
<211> LENGTH: 17
<212> TYPE: DNA
<213> ORGANISM: Homo Sapiens

<400> SEQUENCE: 79
taacattctt gaagcca                                              17

<210> SEQ ID NO 80
<211> LENGTH: 17
<212> TYPE: DNA
<213> ORGANISM: Homo Sapiens

<400> SEQUENCE: 80
taacattcct gaagcca                                              17

<210> SEQ ID NO 81
<211> LENGTH: 17
<212> TYPE: DNA
<213> ORGANISM: Homo Sapiens

<400> SEQUENCE: 81
ccaactgaac cgcacag                                              17

<210> SEQ ID NO 82
<211> LENGTH: 17
<212> TYPE: DNA
<213> ORGANISM: Homo Sapiens

<400> SEQUENCE: 82
ccaactgagc tgcacag                                              17

<210> SEQ ID NO 83
<211> LENGTH: 19
<212> TYPE: DNA
```

<213> ORGANISM: Homo Sapiens

<400> SEQUENCE: 83
gagctagctc acacattct                                              19

<210> SEQ ID NO 84
<211> LENGTH: 19
<212> TYPE: DNA
<213> ORGANISM: Homo Sapiens

<400> SEQUENCE: 84
gagttagctc acacgttct                                              19

<210> SEQ ID NO 85
<211> LENGTH: 17
<212> TYPE: DNA
<213> ORGANISM: Homo Sapiens

<400> SEQUENCE: 85
acgggggggt ggcgtta                                                17

<210> SEQ ID NO 86
<211> LENGTH: 17
<212> TYPE: DNA
<213> ORGANISM: Homo Sapiens

<400> SEQUENCE: 86
acggggggtg gcgttaa                                                17

<210> SEQ ID NO 87
<211> LENGTH: 19
<212> TYPE: DNA
<213> ORGANISM: Homo Sapiens

<400> SEQUENCE: 87
tagacagcca gcgcgtcac                                              19

<210> SEQ ID NO 88
<211> LENGTH: 19
<212> TYPE: DNA
<213> ORGANISM: Homo Sapiens

<400> SEQUENCE: 88
tagatagcca gcgcatcac                                              19

<210> SEQ ID NO 89
<211> LENGTH: 18
<212> TYPE: DNA
<213> ORGANISM: Homo Sapiens

<400> SEQUENCE: 89
gcttttcttg agagtggc                                               18

<210> SEQ ID NO 90
<211> LENGTH: 18
<212> TYPE: DNA
<213> ORGANISM: Homo Sapiens

<400> SEQUENCE: 90
gcttttcttt agagtggc                                               18

<210> SEQ ID NO 91
<211> LENGTH: 18

<212> TYPE: DNA
<213> ORGANISM: Homo Sapiens

<400> SEQUENCE: 91
gcttttcgtg agagtggc                                                 18

<210> SEQ ID NO 92
<211> LENGTH: 17
<212> TYPE: DNA
<213> ORGANISM: Homo Sapiens

<400> SEQUENCE: 92
ctacagataa agttata                                                  17

<210> SEQ ID NO 93
<211> LENGTH: 17
<212> TYPE: DNA
<213> ORGANISM: Homo Sapiens

<400> SEQUENCE: 93
ctacagatga agttata                                                  17

<210> SEQ ID NO 94
<211> LENGTH: 17
<212> TYPE: DNA
<213> ORGANISM: Homo Sapiens

<400> SEQUENCE: 94
tagacctgct gctatct                                                  17

<210> SEQ ID NO 95
<211> LENGTH: 17
<212> TYPE: DNA
<213> ORGANISM: Homo Sapiens

<400> SEQUENCE: 95
tagacctgtt gctatct                                                  17

<210> SEQ ID NO 96
<211> LENGTH: 17
<212> TYPE: DNA
<213> ORGANISM: Homo Sapiens

<400> SEQUENCE: 96
tgttgttctg gcctcca                                                  17

<210> SEQ ID NO 97
<211> LENGTH: 17
<212> TYPE: DNA
<213> ORGANISM: Homo Sapiens

<400> SEQUENCE: 97
tgttgttttg gcctcca                                                  17

<210> SEQ ID NO 98
<211> LENGTH: 17
<212> TYPE: DNA
<213> ORGANISM: Homo Sapiens

<400> SEQUENCE: 98
ttctgagaat ttgttag                                                  17

<210> SEQ ID NO 99

```
<211> LENGTH: 17
<212> TYPE: DNA
<213> ORGANISM: Homo Sapiens

<400> SEQUENCE: 99
ttctgagagt ttgttag                                                    17

<210> SEQ ID NO 100
<211> LENGTH: 17
<212> TYPE: DNA
<213> ORGANISM: Homo Sapiens

<400> SEQUENCE: 100
caggaagcag tagctcc                                                    17

<210> SEQ ID NO 101
<211> LENGTH: 17
<212> TYPE: DNA
<213> ORGANISM: Homo Sapiens

<400> SEQUENCE: 101
caggaagccg tagctcc                                                    17

<210> SEQ ID NO 102
<211> LENGTH: 17
<212> TYPE: DNA
<213> ORGANISM: Homo Sapiens

<400> SEQUENCE: 102
agagtcaggt aagttgc                                                    17

<210> SEQ ID NO 103
<211> LENGTH: 17
<212> TYPE: DNA
<213> ORGANISM: Homo Sapiens

<400> SEQUENCE: 103
agagtcagat aagttgc                                                    17

<210> SEQ ID NO 104
<211> LENGTH: 17
<212> TYPE: DNA
<213> ORGANISM: Homo Sapiens

<400> SEQUENCE: 104
agatttcaaa aagtttt                                                    17

<210> SEQ ID NO 105
<211> LENGTH: 17
<212> TYPE: DNA
<213> ORGANISM: Homo Sapiens

<400> SEQUENCE: 105
agattccaaa aggtttt                                                    17

<210> SEQ ID NO 106
<211> LENGTH: 17
<212> TYPE: DNA
<213> ORGANISM: Homo Sapiens

<400> SEQUENCE: 106
agatttcaaa aagtttt                                                    17
```

```
<210> SEQ ID NO 107
<211> LENGTH: 17
<212> TYPE: DNA
<213> ORGANISM: Homo Sapiens

<400> SEQUENCE: 107
cctgagggga gcaatca                                                    17

<210> SEQ ID NO 108
<211> LENGTH: 17
<212> TYPE: DNA
<213> ORGANISM: Homo Sapiens

<400> SEQUENCE: 108
cctgagggaa gcaatca                                                    17

<210> SEQ ID NO 109
<211> LENGTH: 17
<212> TYPE: DNA
<213> ORGANISM: Homo Sapiens

<400> SEQUENCE: 109
aaggtaagat aactaag                                                    17

<210> SEQ ID NO 110
<211> LENGTH: 17
<212> TYPE: DNA
<213> ORGANISM: Homo Sapiens

<400> SEQUENCE: 110
aaggtaaggt aactaag                                                    17

<210> SEQ ID NO 111
<211> LENGTH: 17
<212> TYPE: DNA
<213> ORGANISM: Homo Sapiens

<400> SEQUENCE: 111
ggactacaca gagaaac                                                    17

<210> SEQ ID NO 112
<211> LENGTH: 17
<212> TYPE: DNA
<213> ORGANISM: Homo Sapiens

<400> SEQUENCE: 112
ggactacata gagaaac                                                    17

<210> SEQ ID NO 113
<211> LENGTH: 17
<212> TYPE: DNA
<213> ORGANISM: Homo Sapiens

<400> SEQUENCE: 113
cccaggctac acgaggg                                                    17

<210> SEQ ID NO 114
<211> LENGTH: 17
<212> TYPE: DNA
<213> ORGANISM: Homo Sapiens

<400> SEQUENCE: 114
cccaggctac atgaggg                                                    17
```

-continued

<210> SEQ ID NO 115
<211> LENGTH: 17
<212> TYPE: DNA
<213> ORGANISM: Homo Sapiens

<400> SEQUENCE: 115
cttaccagtt gtgagac                                                17

<210> SEQ ID NO 116
<211> LENGTH: 17
<212> TYPE: DNA
<213> ORGANISM: Homo Sapiens

<400> SEQUENCE: 116
cttaccactt gtgagac                                                17

<210> SEQ ID NO 117
<211> LENGTH: 17
<212> TYPE: DNA
<213> ORGANISM: Homo Sapiens

<400> SEQUENCE: 117
cttaccagtc gtgagac                                                17

<210> SEQ ID NO 118
<211> LENGTH: 17
<212> TYPE: DNA
<213> ORGANISM: Homo Sapiens

<400> SEQUENCE: 118
ctgccctcag gtcttta                                                17

<210> SEQ ID NO 119
<211> LENGTH: 17
<212> TYPE: DNA
<213> ORGANISM: Homo Sapiens

<400> SEQUENCE: 119
ctgccctccg gtcttta                                                17

<210> SEQ ID NO 120
<211> LENGTH: 17
<212> TYPE: DNA
<213> ORGANISM: Homo Sapiens

<400> SEQUENCE: 120
gcaataaaat tgtttta                                                17

<210> SEQ ID NO 121
<211> LENGTH: 17
<212> TYPE: DNA
<213> ORGANISM: Homo Sapiens

<400> SEQUENCE: 121
gcaatgagat cgtttta                                                17

<210> SEQ ID NO 122
<211> LENGTH: 17
<212> TYPE: DNA
<213> ORGANISM: Homo Sapiens

<400> SEQUENCE: 122
tgttctgtgg agacccc                                                17

<210> SEQ ID NO 123
<211> LENGTH: 17
<212> TYPE: DNA
<213> ORGANISM: Homo Sapiens

<400> SEQUENCE: 123
tgttctgtag agacccc                                                17

<210> SEQ ID NO 124
<211> LENGTH: 17
<212> TYPE: DNA
<213> ORGANISM: Homo Sapiens

<400> SEQUENCE: 124
cacattgaat caaagcc                                                17

<210> SEQ ID NO 125
<211> LENGTH: 17
<212> TYPE: DNA
<213> ORGANISM: Homo Sapiens

<400> SEQUENCE: 125
cacattgagt caaagcc                                                17

<210> SEQ ID NO 126
<211> LENGTH: 17
<212> TYPE: DNA
<213> ORGANISM: Homo Sapiens

<400> SEQUENCE: 126
ggactaccca cccgttc                                                17

<210> SEQ ID NO 127
<211> LENGTH: 17
<212> TYPE: DNA
<213> ORGANISM: Homo Sapiens

<400> SEQUENCE: 127
gcgactgcac ccattct                                                17

<210> SEQ ID NO 128
<211> LENGTH: 17
<212> TYPE: DNA
<213> ORGANISM: Homo Sapiens

<400> SEQUENCE: 128
gcgactgccc ccattct                                                17

<210> SEQ ID NO 129
<211> LENGTH: 17
<212> TYPE: DNA
<213> ORGANISM: Homo Sapiens

<400> SEQUENCE: 129
cctgggccag ccaggaa                                                17

<210> SEQ ID NO 130
<211> LENGTH: 17
<212> TYPE: DNA
<213> ORGANISM: Homo Sapiens

<400> SEQUENCE: 130

-continued cctgggcctg ccaggaa                                                    17

<210> SEQ ID NO 131
<211> LENGTH: 17
<212> TYPE: DNA
<213> ORGANISM: Homo Sapiens

<400> SEQUENCE: 131
ccccaggtaa ccatctt                                                    17

<210> SEQ ID NO 132
<211> LENGTH: 17
<212> TYPE: DNA
<213> ORGANISM: Homo Sapiens

<400> SEQUENCE: 132
ccccaggtga ccatctt                                                    17

<210> SEQ ID NO 133
<211> LENGTH: 17
<212> TYPE: DNA
<213> ORGANISM: Homo Sapiens

<400> SEQUENCE: 133
ttctgtatat tagctga                                                    17

<210> SEQ ID NO 134
<211> LENGTH: 17
<212> TYPE: DNA
<213> ORGANISM: Homo Sapiens

<400> SEQUENCE: 134
tttctatatt aactgac                                                    17

<210> SEQ ID NO 135
<211> LENGTH: 17
<212> TYPE: DNA
<213> ORGANISM: Homo Sapiens

<400> SEQUENCE: 135
ggacccggac ggtcttc                                                    17

<210> SEQ ID NO 136
<211> LENGTH: 17
<212> TYPE: DNA
<213> ORGANISM: Homo Sapiens

<400> SEQUENCE: 136
ggacccggtc ggtcttc                                                    17

<210> SEQ ID NO 137
<211> LENGTH: 17
<212> TYPE: DNA
<213> ORGANISM: Homo Sapiens

<400> SEQUENCE: 137
gtccctaatg ttagcat                                                    17

<210> SEQ ID NO 138
<211> LENGTH: 17
<212> TYPE: DNA
<213> ORGANISM: Homo Sapiens

<400> SEQUENCE: 138

-continued gtccccaatg tcagcat                                                17

<210> SEQ ID NO 139
<211> LENGTH: 17
<212> TYPE: DNA
<213> ORGANISM: Homo Sapiens

<400> SEQUENCE: 139
acgggggggt ggcgtta                                                17

<210> SEQ ID NO 140
<211> LENGTH: 17
<212> TYPE: DNA
<213> ORGANISM: Homo Sapiens

<400> SEQUENCE: 140
acggggggtg gcgttaa                                                17

<210> SEQ ID NO 141
<211> LENGTH: 19
<212> TYPE: DNA
<213> ORGANISM: Homo Sapiens

<400> SEQUENCE: 141
tagacagcca gcgcgtcac                                              19

<210> SEQ ID NO 142
<211> LENGTH: 19
<212> TYPE: DNA
<213> ORGANISM: Homo Sapiens

<400> SEQUENCE: 142
tagatagcca gcgcatcac                                              19

<210> SEQ ID NO 143
<211> LENGTH: 17
<212> TYPE: DNA
<213> ORGANISM: Homo Sapiens

<400> SEQUENCE: 143
gattcttcgt gttcctt                                                17

<210> SEQ ID NO 144
<211> LENGTH: 17
<212> TYPE: DNA
<213> ORGANISM: Homo Sapiens

<400> SEQUENCE: 144
gattcttcat gttcctt                                                17

<210> SEQ ID NO 145
<211> LENGTH: 17
<212> TYPE: DNA
<213> ORGANISM: Homo Sapiens

<400> SEQUENCE: 145
tgtaaaaact tagaata                                                17

<210> SEQ ID NO 146
<211> LENGTH: 17
<212> TYPE: DNA
<213> ORGANISM: Homo Sapiens -continued

```
<400> SEQUENCE: 146
tgtaaaaatt tagaata                                                 17

<210> SEQ ID NO 147
<211> LENGTH: 17
<212> TYPE: DNA
<213> ORGANISM: Homo Sapiens

<400> SEQUENCE: 147
tgtgaaagcg ctcccaa                                                 17

<210> SEQ ID NO 148
<211> LENGTH: 17
<212> TYPE: DNA
<213> ORGANISM: Homo Sapiens

<400> SEQUENCE: 148
tgtgaaagtg ctcccaa                                                 17

<210> SEQ ID NO 149
<211> LENGTH: 17
<212> TYPE: DNA
<213> ORGANISM: Homo Sapiens

<400> SEQUENCE: 149
caaaggctca gagaatc                                                 17

<210> SEQ ID NO 150
<211> LENGTH: 17
<212> TYPE: DNA
<213> ORGANISM: Homo Sapiens

<400> SEQUENCE: 150
caaaggctta gagaatc                                                 17

<210> SEQ ID NO 151
<211> LENGTH: 17
<212> TYPE: DNA
<213> ORGANISM: Homo Sapiens

<400> SEQUENCE: 151
ttaattctct ccaaaca                                                 17

<210> SEQ ID NO 152
<211> LENGTH: 17
<212> TYPE: DNA
<213> ORGANISM: Homo Sapiens

<400> SEQUENCE: 152
ttaaggctct ccggaca                                                 17

<210> SEQ ID NO 153
<211> LENGTH: 17
<212> TYPE: DNA
<213> ORGANISM: Homo Sapiens

<400> SEQUENCE: 153
ctgccaccgt gcacaca                                                 17

<210> SEQ ID NO 154
<211> LENGTH: 17
<212> TYPE: DNA
<213> ORGANISM: Homo Sapiens
```

```
<400> SEQUENCE: 154
ctgccaccat gcacaca                                                    17

<210> SEQ ID NO 155
<211> LENGTH: 17
<212> TYPE: DNA
<213> ORGANISM: Homo Sapiens

<400> SEQUENCE: 155
ccaaatattc tgattcc                                                    17

<210> SEQ ID NO 156
<211> LENGTH: 17
<212> TYPE: DNA
<213> ORGANISM: Homo Sapiens

<400> SEQUENCE: 156
ccaaatattc tttttttt                                                   17

<210> SEQ ID NO 157
<211> LENGTH: 17
<212> TYPE: DNA
<213> ORGANISM: Homo Sapiens

<400> SEQUENCE: 157
atgagctgac cctccct                                                    17

<210> SEQ ID NO 158
<211> LENGTH: 17
<212> TYPE: DNA
<213> ORGANISM: Homo Sapiens

<400> SEQUENCE: 158
atgagctgcc cctccct                                                    17

<210> SEQ ID NO 159
<211> LENGTH: 17
<212> TYPE: DNA
<213> ORGANISM: Homo Sapiens

<400> SEQUENCE: 159
acactaggta aaagctc                                                    17

<210> SEQ ID NO 160
<211> LENGTH: 17
<212> TYPE: DNA
<213> ORGANISM: Homo Sapiens

<400> SEQUENCE: 160
acactaggca aaagctc                                                    17

<210> SEQ ID NO 161
<211> LENGTH: 17
<212> TYPE: DNA
<213> ORGANISM: Homo Sapiens

<400> SEQUENCE: 161
agacaccacg accgagg                                                    17

<210> SEQ ID NO 162
<211> LENGTH: 17
<212> TYPE: DNA
```

```
<213> ORGANISM: Homo Sapiens

<400> SEQUENCE: 162
agacaccaag accgagg                                                 17

<210> SEQ ID NO 163
<211> LENGTH: 17
<212> TYPE: DNA
<213> ORGANISM: Homo Sapiens

<400> SEQUENCE: 163
gcagcgtccg gttaagt                                                 17

<210> SEQ ID NO 164
<211> LENGTH: 17
<212> TYPE: DNA
<213> ORGANISM: Homo Sapiens

<400> SEQUENCE: 164
gcagcgtctg gttaagt                                                 17

<210> SEQ ID NO 165
<211> LENGTH: 17
<212> TYPE: DNA
<213> ORGANISM: Homo Sapiens

<400> SEQUENCE: 165
cagatactac aaggatg                                                 17

<210> SEQ ID NO 166
<211> LENGTH: 17
<212> TYPE: DNA
<213> ORGANISM: Homo Sapiens

<400> SEQUENCE: 166
tacagataca aggatgc                                                 17

<210> SEQ ID NO 167
<211> LENGTH: 17
<212> TYPE: DNA
<213> ORGANISM: Homo Sapiens

<400> SEQUENCE: 167
tcagctagtg tatctgt                                                 17

<210> SEQ ID NO 168
<211> LENGTH: 17
<212> TYPE: DNA
<213> ORGANISM: Homo Sapiens

<400> SEQUENCE: 168
tcacctagtg tatttgt                                                 17

<210> SEQ ID NO 169
<211> LENGTH: 17
<212> TYPE: DNA
<213> ORGANISM: Homo Sapiens

<400> SEQUENCE: 169 tttttttattt ttggatt                                                17

<210> SEQ ID NO 170
<211> LENGTH: 17
```

```
<212> TYPE: DNA
<213> ORGANISM: Homo Sapiens

<400> SEQUENCE: 170
ttttaatttt tggattt                                                17

<210> SEQ ID NO 171
<211> LENGTH: 17
<212> TYPE: DNA
<213> ORGANISM: Homo Sapiens

<400> SEQUENCE: 171
gatattgttt tcattta                                                17

<210> SEQ ID NO 172
<211> LENGTH: 17
<212> TYPE: DNA
<213> ORGANISM: Homo Sapiens

<400> SEQUENCE: 172
gatattgtct tcattta                                                17

<210> SEQ ID NO 173
<211> LENGTH: 17
<212> TYPE: DNA
<213> ORGANISM: Homo Sapiens

<400> SEQUENCE: 173
agacccggtg ctggtgt                                                17

<210> SEQ ID NO 174
<211> LENGTH: 17
<212> TYPE: DNA
<213> ORGANISM: Homo Sapiens

<400> SEQUENCE: 174
agacccggcg ctggtgt                                                17

<210> SEQ ID NO 175
<211> LENGTH: 17
<212> TYPE: DNA
<213> ORGANISM: Homo Sapiens

<400> SEQUENCE: 175
cttctaagct ttgtctt                                                17

<210> SEQ ID NO 176
<211> LENGTH: 17
<212> TYPE: DNA
<213> ORGANISM: Homo Sapiens

<400> SEQUENCE: 176
cttctaagtt ttgtctt                                                17

<210> SEQ ID NO 177
<211> LENGTH: 17
<212> TYPE: DNA
<213> ORGANISM: Homo Sapiens

<400> SEQUENCE: 177
agttggcaac cagcatg                                                17

<210> SEQ ID NO 178
```

```
<211> LENGTH: 17
<212> TYPE: DNA
<213> ORGANISM: Homo Sapiens

<400> SEQUENCE: 178
agttggcatc cagcatg                                                    17

<210> SEQ ID NO 179
<211> LENGTH: 17
<212> TYPE: DNA
<213> ORGANISM: Homo Sapiens

<400> SEQUENCE: 179
ggtgaaatgg taattac                                                    17

<210> SEQ ID NO 180
<211> LENGTH: 17
<212> TYPE: DNA
<213> ORGANISM: Homo Sapiens

<400> SEQUENCE: 180
ggtgaaatag taattac                                                    17

<210> SEQ ID NO 181
<211> LENGTH: 17
<212> TYPE: DNA
<213> ORGANISM: Homo Sapiens

<400> SEQUENCE: 181
acgggatata acgagtt                                                    17

<210> SEQ ID NO 182
<211> LENGTH: 17
<212> TYPE: DNA
<213> ORGANISM: Homo Sapiens

<400> SEQUENCE: 182
acgggataca acgagtt                                                    17

<210> SEQ ID NO 183
<211> LENGTH: 17
<212> TYPE: DNA
<213> ORGANISM: Homo Sapiens

<400> SEQUENCE: 183
gggatacaac gagtttc                                                    17

<210> SEQ ID NO 184
<211> LENGTH: 17
<212> TYPE: DNA
<213> ORGANISM: Homo Sapiens

<400> SEQUENCE: 184
gggatacacc gagtttc                                                    17

<210> SEQ ID NO 185
<211> LENGTH: 17
<212> TYPE: DNA
<213> ORGANISM: Homo Sapiens

<400> SEQUENCE: 185
gtatcttggg tgtcctg                                                    17
```

-continued

<210> SEQ ID NO 186
<211> LENGTH: 17
<212> TYPE: DNA
<213> ORGANISM: Homo Sapiens

<400> SEQUENCE: 186
gtaacttggg tgttctg                                                  17

<210> SEQ ID NO 187
<211> LENGTH: 17
<212> TYPE: DNA
<213> ORGANISM: Homo Sapiens

<400> SEQUENCE: 187
gggtgtcctg ccccatc                                                  17

<210> SEQ ID NO 188
<211> LENGTH: 17
<212> TYPE: DNA
<213> ORGANISM: Homo Sapiens

<400> SEQUENCE: 188
gggtgttctg ttttatc                                                  17

<210> SEQ ID NO 189
<211> LENGTH: 17
<212> TYPE: DNA
<213> ORGANISM: Homo Sapiens

<400> SEQUENCE: 189
tgtccagttg ttttgca                                                  17

<210> SEQ ID NO 190
<211> LENGTH: 17
<212> TYPE: DNA
<213> ORGANISM: Homo Sapiens

<400> SEQUENCE: 190
tgtccagtcg ttttgca                                                  17

<210> SEQ ID NO 191
<211> LENGTH: 17
<212> TYPE: DNA
<213> ORGANISM: Homo Sapiens

<400> SEQUENCE: 191
aagacagccg gaactct                                                  17

<210> SEQ ID NO 192
<211> LENGTH: 17
<212> TYPE: DNA
<213> ORGANISM: Homo Sapiens

<400> SEQUENCE: 192
aagacagcag gaactct                                                  17

<210> SEQ ID NO 193
<211> LENGTH: 17
<212> TYPE: DNA
<213> ORGANISM: Homo Sapiens

<400> SEQUENCE: 193
tgataggacc aaagaga                                                  17

<210> SEQ ID NO 194
<211> LENGTH: 17
<212> TYPE: DNA
<213> ORGANISM: Homo Sapiens

<400> SEQUENCE: 194
cgataggact aaagaga                                                17

<210> SEQ ID NO 195
<211> LENGTH: 17
<212> TYPE: DNA
<213> ORGANISM: Homo Sapiens

<400> SEQUENCE: 195
tccaaagcca gggccca                                                17

<210> SEQ ID NO 196
<211> LENGTH: 17
<212> TYPE: DNA
<213> ORGANISM: Homo Sapiens

<400> SEQUENCE: 196
tccaaattca gggccca                                                17

<210> SEQ ID NO 197
<211> LENGTH: 17
<212> TYPE: DNA
<213> ORGANISM: Homo Sapiens

<400> SEQUENCE: 197
cctgggccag ccagaag                                                17

<210> SEQ ID NO 198
<211> LENGTH: 17
<212> TYPE: DNA
<213> ORGANISM: Homo Sapiens

<400> SEQUENCE: 198
cctgggcctg ccagaag                                                17

<210> SEQ ID NO 199
<211> LENGTH: 17
<212> TYPE: DNA
<213> ORGANISM: Homo Sapiens

<400> SEQUENCE: 199
gattctctga gcctttg                                                17

<210> SEQ ID NO 200
<211> LENGTH: 17
<212> TYPE: DNA
<213> ORGANISM: Homo Sapiens

<400> SEQUENCE: 200
gattctctaa gcctttg                                                17

<210> SEQ ID NO 201
<211> LENGTH: 17
<212> TYPE: DNA
<213> ORGANISM: Homo Sapiens

<400> SEQUENCE: 201
taccattttt tagatga                                                17

<210> SEQ ID NO 202
<211> LENGTH: 17
<212> TYPE: DNA
<213> ORGANISM: Homo Sapiens

<400> SEQUENCE: 202
taccatttct tagatga                                                    17

<210> SEQ ID NO 203
<211> LENGTH: 17
<212> TYPE: DNA
<213> ORGANISM: Homo Sapiens

<400> SEQUENCE: 203
ctggaagggc agtgaat                                                    17

<210> SEQ ID NO 204
<211> LENGTH: 17
<212> TYPE: DNA
<213> ORGANISM: Homo Sapiens

<400> SEQUENCE: 204
tctggacgag ggtgaat                                                    17

<210> SEQ ID NO 205
<211> LENGTH: 17
<212> TYPE: DNA
<213> ORGANISM: Homo Sapiens

<400> SEQUENCE: 205
tagttgcagc acaaatg                                                    17

<210> SEQ ID NO 206
<211> LENGTH: 17
<212> TYPE: DNA
<213> ORGANISM: Homo Sapiens

<400> SEQUENCE: 206
tagttgtagc acaaatg                                                    17

<210> SEQ ID NO 207
<211> LENGTH: 17
<212> TYPE: DNA
<213> ORGANISM: Homo Sapiens

<400> SEQUENCE: 207
acactaccgc acagagc                                                    17

<210> SEQ ID NO 208
<211> LENGTH: 17
<212> TYPE: DNA
<213> ORGANISM: Homo Sapiens

<400> SEQUENCE: 208
acactaccac acagagc                                                    17

<210> SEQ ID NO 209
<211> LENGTH: 17
<212> TYPE: DNA
<213> ORGANISM: Homo Sapiens

<400> SEQUENCE: 209

-continued aataataagt aaataag         17

<210> SEQ ID NO 210
<211> LENGTH: 17
<212> TYPE: DNA
<213> ORGANISM: Homo Sapiens

<400> SEQUENCE: 210
aataataaat aaataag         17

<210> SEQ ID NO 211
<211> LENGTH: 17
<212> TYPE: DNA
<213> ORGANISM: Homo Sapiens

<400> SEQUENCE: 211
tggcagtagt tgttcat         17

<210> SEQ ID NO 212
<211> LENGTH: 17
<212> TYPE: DNA
<213> ORGANISM: Homo Sapiens

<400> SEQUENCE: 212
tggcagtaat tgttcat         17

<210> SEQ ID NO 213
<211> LENGTH: 17
<212> TYPE: DNA
<213> ORGANISM: Homo Sapiens

<400> SEQUENCE: 213
aggtatgacg tcataag         17

<210> SEQ ID NO 214
<211> LENGTH: 17
<212> TYPE: DNA
<213> ORGANISM: Homo Sapiens

<400> SEQUENCE: 214
aggtatgatg tcataag         17

<210> SEQ ID NO 215
<211> LENGTH: 17
<212> TYPE: DNA
<213> ORGANISM: Homo Sapiens

<400> SEQUENCE: 215
gttgttgttg aagattt         17

<210> SEQ ID NO 216
<211> LENGTH: 17
<212> TYPE: DNA
<213> ORGANISM: Homo Sapiens

<400> SEQUENCE: 216
ttgttgttga agattta         17

<210> SEQ ID NO 217
<211> LENGTH: 19
<212> TYPE: DNA
<213> ORGANISM: Homo Sapiens

<400> SEQUENCE: 217
gatagtacag gtgttgtca                                                19

<210> SEQ ID NO 218
<211> LENGTH: 19
<212> TYPE: DNA
<213> ORGANISM: Homo Sapiens

<400> SEQUENCE: 218
gatggtacag gtgtcgtca                                                19

<210> SEQ ID NO 219
<211> LENGTH: 17
<212> TYPE: DNA
<213> ORGANISM: Homo Sapiens

<400> SEQUENCE: 219
aatataatgt aacagga                                                  17

<210> SEQ ID NO 220
<211> LENGTH: 17
<212> TYPE: DNA
<213> ORGANISM: Homo Sapiens

<400> SEQUENCE: 220
aatataatat aacagga                                                  17

<210> SEQ ID NO 221
<211> LENGTH: 17
<212> TYPE: DNA
<213> ORGANISM: Homo Sapiens

<400> SEQUENCE: 221
ttaaccattt atctgat                                                  17

<210> SEQ ID NO 222
<211> LENGTH: 17
<212> TYPE: DNA
<213> ORGANISM: Homo Sapiens

<400> SEQUENCE: 222
ttaaccatat atctgat                                                  17

<210> SEQ ID NO 223
<211> LENGTH: 17
<212> TYPE: DNA
<213> ORGANISM: Homo Sapiens

<400> SEQUENCE: 223
agagcccagc aaagttc                                                  17

<210> SEQ ID NO 224
<211> LENGTH: 17
<212> TYPE: DNA
<213> ORGANISM: Homo Sapiens

<400> SEQUENCE: 224
agagcccaac aaagttc                                                  17

<210> SEQ ID NO 225
<211> LENGTH: 19
<212> TYPE: DNA
<213> ORGANISM: Homo Sapiens

```
<400> SEQUENCE: 225
atcccgaacc ggggaaaat                                              19

<210> SEQ ID NO 226
<211> LENGTH: 19
<212> TYPE: DNA
<213> ORGANISM: Homo Sapiens

<400> SEQUENCE: 226
atcccaaacc gggggaaat                                              19

<210> SEQ ID NO 227
<211> LENGTH: 17
<212> TYPE: DNA
<213> ORGANISM: Homo Sapiens

<400> SEQUENCE: 227
atgacaccac cacaacc                                                17

<210> SEQ ID NO 228
<211> LENGTH: 17
<212> TYPE: DNA
<213> ORGANISM: Homo Sapiens

<400> SEQUENCE: 228
atgacaccgc cacaacc                                                17

<210> SEQ ID NO 229
<211> LENGTH: 17
<212> TYPE: DNA
<213> ORGANISM: Homo Sapiens

<400> SEQUENCE: 229
aggcaaacag atataac                                                17

<210> SEQ ID NO 230
<211> LENGTH: 17
<212> TYPE: DNA
<213> ORGANISM: Homo Sapiens

<400> SEQUENCE: 230
aggcaaacgg atataac                                                17

<210> SEQ ID NO 231
<211> LENGTH: 17
<212> TYPE: DNA
<213> ORGANISM: Homo Sapiens

<400> SEQUENCE: 231
tgtattcact aataaga                                                17

<210> SEQ ID NO 232
<211> LENGTH: 17
<212> TYPE: DNA
<213> ORGANISM: Homo Sapiens

<400> SEQUENCE: 232
tgtattcatt aataaga                                                17

<210> SEQ ID NO 233
<211> LENGTH: 17
<212> TYPE: DNA
<213> ORGANISM: Homo Sapiens
```

```
<400> SEQUENCE: 233
ttggcgtata cttcata                                                17

<210> SEQ ID NO 234
<211> LENGTH: 17
<212> TYPE: DNA
<213> ORGANISM: Homo Sapiens

<400> SEQUENCE: 234
ttggcgtaca cttcata                                                17

<210> SEQ ID NO 235
<211> LENGTH: 17
<212> TYPE: DNA
<213> ORGANISM: Homo Sapiens

<400> SEQUENCE: 235
ctcaccacgc tccatct                                                17

<210> SEQ ID NO 236
<211> LENGTH: 17
<212> TYPE: DNA
<213> ORGANISM: Homo Sapiens

<400> SEQUENCE: 236
ctcaccaccc tccatct                                                17

<210> SEQ ID NO 237
<211> LENGTH: 16
<212> TYPE: DNA
<213> ORGANISM: Homo Sapiens

<400> SEQUENCE: 237
atatctaaag gcacag                                                 16

<210> SEQ ID NO 238
<211> LENGTH: 17
<212> TYPE: DNA
<213> ORGANISM: Homo Sapiens

<400> SEQUENCE: 238
tatctacata aaggcac                                                17

<210> SEQ ID NO 239
<211> LENGTH: 17
<212> TYPE: DNA
<213> ORGANISM: Homo Sapiens

<400> SEQUENCE: 239
gtgtctccta gtctccc                                                17

<210> SEQ ID NO 240
<211> LENGTH: 17
<212> TYPE: DNA
<213> ORGANISM: Homo Sapiens

<400> SEQUENCE: 240
gtgtctccca gtctccc                                                17

<210> SEQ ID NO 241
<211> LENGTH: 17
<212> TYPE: DNA
```

```
<213> ORGANISM: Homo Sapiens

<400> SEQUENCE: 241
atgagctgac cctccct                                                    17

<210> SEQ ID NO 242
<211> LENGTH: 17
<212> TYPE: DNA
<213> ORGANISM: Homo Sapiens

<400> SEQUENCE: 242
atgagctgcc cctccct                                                    17

<210> SEQ ID NO 243
<211> LENGTH: 17
<212> TYPE: DNA
<213> ORGANISM: Homo Sapiens

<400> SEQUENCE: 243
ggacaacatt taattgg                                                    17

<210> SEQ ID NO 244
<211> LENGTH: 17
<212> TYPE: DNA
<213> ORGANISM: Homo Sapiens

<400> SEQUENCE: 244
ggacaacact taattgg                                                    17

<210> SEQ ID NO 245
<211> LENGTH: 17
<212> TYPE: DNA
<213> ORGANISM: Homo Sapiens

<400> SEQUENCE: 245
gctttaaaat ttttatt                                                    17

<210> SEQ ID NO 246
<211> LENGTH: 17
<212> TYPE: DNA
<213> ORGANISM: Homo Sapiens

<400> SEQUENCE: 246
gctttaaatt ttttatt                                                    17

<210> SEQ ID NO 247
<211> LENGTH: 17
<212> TYPE: DNA
<213> ORGANISM: Homo Sapiens

<400> SEQUENCE: 247
aaatttgttc ctaaatg                                                    17

<210> SEQ ID NO 248
<211> LENGTH: 17
<212> TYPE: DNA
<213> ORGANISM: Homo Sapiens

<400> SEQUENCE: 248
aaatttgtac ctaaatg                                                    17

<210> SEQ ID NO 249
<211> LENGTH: 17
```

```
<212> TYPE: DNA
<213> ORGANISM: Homo Sapiens

<400> SEQUENCE: 249
gtgttgttct ggcctcc                                                  17

<210> SEQ ID NO 250
<211> LENGTH: 17
<212> TYPE: DNA
<213> ORGANISM: Homo Sapiens

<400> SEQUENCE: 250
gtgttgtttt ggcctcc                                                  17

<210> SEQ ID NO 251
<211> LENGTH: 17
<212> TYPE: DNA
<213> ORGANISM: Homo Sapiens

<400> SEQUENCE: 251
tgaatgacaa aaagaca                                                  17

<210> SEQ ID NO 252
<211> LENGTH: 17
<212> TYPE: DNA
<213> ORGANISM: Homo Sapiens

<400> SEQUENCE: 252
tgaatgacga aaagaca                                                  17

<210> SEQ ID NO 253
<211> LENGTH: 18
<212> TYPE: DNA
<213> ORGANISM: Homo Sapiens

<400> SEQUENCE: 253
actgagccat ctcwccag                                                 18

<210> SEQ ID NO 254
<211> LENGTH: 17
<212> TYPE: DNA
<213> ORGANISM: Homo Sapiens

<400> SEQUENCE: 254
acttaactta agctggc                                                  17

<210> SEQ ID NO 255
<211> LENGTH: 17
<212> TYPE: DNA
<213> ORGANISM: Homo Sapiens

<400> SEQUENCE: 255
gtacttaagc tggcctg                                                  17

<210> SEQ ID NO 256
<211> LENGTH: 17
<212> TYPE: DNA
<213> ORGANISM: Homo Sapiens

<400> SEQUENCE: 256
actctaatat cccacag                                                  17

<210> SEQ ID NO 257
```

<210> SEQ ID NO 257
<211> LENGTH: 17
<212> TYPE: DNA
<213> ORGANISM: Homo Sapiens

<400> SEQUENCE: 257
actctaatct cccacag                                                  17

<210> SEQ ID NO 258
<211> LENGTH: 17
<212> TYPE: DNA
<213> ORGANISM: Homo Sapiens

<400> SEQUENCE: 258
cggatcggct ctagttc                                                  17

<210> SEQ ID NO 259
<211> LENGTH: 17
<212> TYPE: DNA
<213> ORGANISM: Homo Sapiens

<400> SEQUENCE: 259
cggatcagct ctagttc                                                  17

<210> SEQ ID NO 260
<211> LENGTH: 17
<212> TYPE: DNA
<213> ORGANISM: Homo Sapiens

<400> SEQUENCE: 260
tcaaaccaat aaggagg                                                  17

<210> SEQ ID NO 261
<211> LENGTH: 17
<212> TYPE: DNA
<213> ORGANISM: Homo Sapiens

<400> SEQUENCE: 261
tcaaaccagt aaggagg                                                  17

<210> SEQ ID NO 262
<211> LENGTH: 17
<212> TYPE: DNA
<213> ORGANISM: Homo Sapiens

<400> SEQUENCE: 262
gtgtgtgtgt gggggggg                                                 17

<210> SEQ ID NO 263
<211> LENGTH: 17
<212> TYPE: DNA
<213> ORGANISM: Homo Sapiens

<400> SEQUENCE: 263
gtgtgtgtgg gggggt                                                   17

<210> SEQ ID NO 264
<211> LENGTH: 17
<212> TYPE: DNA
<213> ORGANISM: Homo Sapiens

<400> SEQUENCE: 264
cttaataata atttcat                                                  17

```
<210> SEQ ID NO 265
<211> LENGTH: 17
<212> TYPE: DNA
<213> ORGANISM: Homo Sapiens

<400> SEQUENCE: 265
cttaataaca atttcat                                                17

<210> SEQ ID NO 266
<211> LENGTH: 17
<212> TYPE: DNA
<213> ORGANISM: Homo Sapiens

<400> SEQUENCE: 266
gtgtctccat atgtgtg                                                17

<210> SEQ ID NO 267
<211> LENGTH: 17
<212> TYPE: DNA
<213> ORGANISM: Homo Sapiens

<400> SEQUENCE: 267
gtgtctacac atgtgtg                                                17

<210> SEQ ID NO 268
<211> LENGTH: 17
<212> TYPE: DNA
<213> ORGANISM: Homo Sapiens

<400> SEQUENCE: 268
aactcatcat gatggtt                                                17

<210> SEQ ID NO 269
<211> LENGTH: 17
<212> TYPE: DNA
<213> ORGANISM: Homo Sapiens

<400> SEQUENCE: 269
aactcataat gatggtt                                                17

<210> SEQ ID NO 270
<211> LENGTH: 17
<212> TYPE: DNA
<213> ORGANISM: Homo Sapiens

<400> SEQUENCE: 270
aactcatcac gatggtt                                                17

<210> SEQ ID NO 271
<211> LENGTH: 17
<212> TYPE: DNA
<213> ORGANISM: Homo Sapiens

<400> SEQUENCE: 271
atcactcata gcccaga                                                17

<210> SEQ ID NO 272
<211> LENGTH: 17
<212> TYPE: DNA
<213> ORGANISM: Homo Sapiens

<400> SEQUENCE: 272
atcacttata gcccaga                                                17
```

```
<210> SEQ ID NO 273
<211> LENGTH: 17
<212> TYPE: DNA
<213> ORGANISM: Homo Sapiens

<400> SEQUENCE: 273
atcactcata tcccaga                                                17

<210> SEQ ID NO 274
<211> LENGTH: 17
<212> TYPE: DNA
<213> ORGANISM: Homo Sapiens

<400> SEQUENCE: 274
catcttacca gcattga                                                17

<210> SEQ ID NO 275
<211> LENGTH: 17
<212> TYPE: DNA
<213> ORGANISM: Homo Sapiens

<400> SEQUENCE: 275
catcttacta gcattga                                                17

<210> SEQ ID NO 276
<211> LENGTH: 17
<212> TYPE: DNA
<213> ORGANISM: Homo Sapiens

<400> SEQUENCE: 276
agtcagccgg ctctggc                                                17

<210> SEQ ID NO 277
<211> LENGTH: 17
<212> TYPE: DNA
<213> ORGANISM: Homo Sapiens

<400> SEQUENCE: 277
agtcagccag ctctggc                                                17

<210> SEQ ID NO 278
<211> LENGTH: 19
<212> TYPE: DNA
<213> ORGANISM: Homo Sapiens

<400> SEQUENCE: 278
gggtaggagt gggggtgag                                              19

<210> SEQ ID NO 279
<211> LENGTH: 19
<212> TYPE: DNA
<213> ORGANISM: Homo Sapiens

<400> SEQUENCE: 279
gggcaggagt gggggtgag                                              19

<210> SEQ ID NO 280
<211> LENGTH: 19
<212> TYPE: DNA
<213> ORGANISM: Homo Sapiens

<400> SEQUENCE: 280
gggtaggagt gggggtgag                                              19
```

<210> SEQ ID NO 281
<211> LENGTH: 17
<212> TYPE: DNA
<213> ORGANISM: Homo Sapiens

<400> SEQUENCE: 281
tcagtattgt tcttctc                                                17

<210> SEQ ID NO 282
<211> LENGTH: 17
<212> TYPE: DNA
<213> ORGANISM: Homo Sapiens

<400> SEQUENCE: 282
tcagtatttt tcttctc                                                17

<210> SEQ ID NO 283
<211> LENGTH: 17
<212> TYPE: DNA
<213> ORGANISM: Homo Sapiens

<400> SEQUENCE: 283
agcagagact gagctcg                                                17

<210> SEQ ID NO 284
<211> LENGTH: 17
<212> TYPE: DNA
<213> ORGANISM: Homo Sapiens

<400> SEQUENCE: 284
agcagagacc gagctcg                                                17

<210> SEQ ID NO 285
<211> LENGTH: 17
<212> TYPE: DNA
<213> ORGANISM: Homo Sapiens

<400> SEQUENCE: 285 acagggtcg attcgtc                                                 17

<210> SEQ ID NO 286
<211> LENGTH: 17
<212> TYPE: DNA
<213> ORGANISM: Homo Sapiens

<400> SEQUENCE: 286
acagggatcg attcgtc                                                17

<210> SEQ ID NO 287
<211> LENGTH: 17
<212> TYPE: DNA
<213> ORGANISM: Homo Sapiens

<400> SEQUENCE: 287 acagggtcg tttcgtc                                                 17

<210> SEQ ID NO 288
<211> LENGTH: 17
<212> TYPE: DNA
<213> ORGANISM: Homo Sapiens

<400> SEQUENCE: 288
tcccaaagca ttcaagg    17

<210> SEQ ID NO 289
<211> LENGTH: 17
<212> TYPE: DNA
<213> ORGANISM: Homo Sapiens

<400> SEQUENCE: 289
tcccaaagta ttcaagg    17

<210> SEQ ID NO 290
<211> LENGTH: 17
<212> TYPE: DNA
<213> ORGANISM: Homo Sapiens

<400> SEQUENCE: 290
gaccagggtt aatgact    17

<210> SEQ ID NO 291
<211> LENGTH: 17
<212> TYPE: DNA
<213> ORGANISM: Homo Sapiens

<400> SEQUENCE: 291
gaccagggct aatgact    17

<210> SEQ ID NO 292
<211> LENGTH: 17
<212> TYPE: DNA
<213> ORGANISM: Homo Sapiens

<400> SEQUENCE: 292
ctattaacag agtcgag    17

<210> SEQ ID NO 293
<211> LENGTH: 17
<212> TYPE: DNA
<213> ORGANISM: Homo Sapiens

<400> SEQUENCE: 293
ctattaacgg agtcgag    17

<210> SEQ ID NO 294
<211> LENGTH: 17
<212> TYPE: DNA
<213> ORGANISM: Homo Sapiens

<400> SEQUENCE: 294
gtgatactgg atgtctg    17

<210> SEQ ID NO 295
<211> LENGTH: 17
<212> TYPE: DNA
<213> ORGANISM: Homo Sapiens

<400> SEQUENCE: 295
gtgataccga tgtctgg    17

<210> SEQ ID NO 296
<211> LENGTH: 17
<212> TYPE: DNA
<213> ORGANISM: Homo Sapiens

<400> SEQUENCE: 296

-continued ctctctcgat agtctaa 17

<210> SEQ ID NO 297
<211> LENGTH: 17
<212> TYPE: DNA
<213> ORGANISM: Homo Sapiens

<400> SEQUENCE: 297
ctctctcgct agtctaa 17

<210> SEQ ID NO 298
<211> LENGTH: 17
<212> TYPE: DNA
<213> ORGANISM: Homo Sapiens

<400> SEQUENCE: 298
tctctcgata gtctaat 17

<210> SEQ ID NO 299
<211> LENGTH: 17
<212> TYPE: DNA
<213> ORGANISM: Homo Sapiens

<400> SEQUENCE: 299
tctctcgctg gtctaat 17

<210> SEQ ID NO 300
<211> LENGTH: 17
<212> TYPE: DNA
<213> ORGANISM: Homo Sapiens

<400> SEQUENCE: 300
agatgcaaaa ttcttag 17

<210> SEQ ID NO 301
<211> LENGTH: 17
<212> TYPE: DNA
<213> ORGANISM: Homo Sapiens

<400> SEQUENCE: 301
agatgcacag ttcttag 17

<210> SEQ ID NO 302
<211> LENGTH: 17
<212> TYPE: DNA
<213> ORGANISM: Homo Sapiens

<400> SEQUENCE: 302
ggaaaatgct caggtag 17

<210> SEQ ID NO 303
<211> LENGTH: 17
<212> TYPE: DNA
<213> ORGANISM: Homo Sapiens

<400> SEQUENCE: 303
ggaaaatgtt caggtag 17

<210> SEQ ID NO 304
<211> LENGTH: 17
<212> TYPE: DNA
<213> ORGANISM: Homo Sapiens

```
<400> SEQUENCE: 304
tctgggcaga gtgcagg                                                    17

<210> SEQ ID NO 305
<211> LENGTH: 17
<212> TYPE: DNA
<213> ORGANISM: Homo Sapiens

<400> SEQUENCE: 305
tctgggcagc gtgcagg                                                    17

<210> SEQ ID NO 306
<211> LENGTH: 17
<212> TYPE: DNA
<213> ORGANISM: Homo Sapiens

<400> SEQUENCE: 306
tatggaacgg ttgcttc                                                    17

<210> SEQ ID NO 307
<211> LENGTH: 17
<212> TYPE: DNA
<213> ORGANISM: Homo Sapiens

<400> SEQUENCE: 307
tatggaactg ttgcttc                                                    17

<210> SEQ ID NO 308
<211> LENGTH: 17
<212> TYPE: DNA
<213> ORGANISM: Homo Sapiens

<400> SEQUENCE: 308
aagcctggta cccgctg                                                    17

<210> SEQ ID NO 309
<211> LENGTH: 17
<212> TYPE: DNA
<213> ORGANISM: Homo Sapiens

<400> SEQUENCE: 309
aagcctggca cccgctg                                                    17

<210> SEQ ID NO 310
<211> LENGTH: 17
<212> TYPE: DNA
<213> ORGANISM: Homo Sapiens

<400> SEQUENCE: 310
cattcttctt tttctga                                                    17

<210> SEQ ID NO 311
<211> LENGTH: 17
<212> TYPE: DNA
<213> ORGANISM: Homo Sapiens

<400> SEQUENCE: 311
cattcttcgt tttctga                                                    17

<210> SEQ ID NO 312
<211> LENGTH: 17
<212> TYPE: DNA
<213> ORGANISM: Homo Sapiens
```

-continued

```
<400> SEQUENCE: 312
ctgcaggctt gtctgtg                                                    17

<210> SEQ ID NO 313
<211> LENGTH: 17
<212> TYPE: DNA
<213> ORGANISM: Homo Sapiens

<400> SEQUENCE: 313
ctgcaggttt gtctgtg                                                    17

<210> SEQ ID NO 314
<211> LENGTH: 17
<212> TYPE: DNA
<213> ORGANISM: Homo Sapiens

<400> SEQUENCE: 314
tgccatttcc tataaca                                                    17

<210> SEQ ID NO 315
<211> LENGTH: 17
<212> TYPE: DNA
<213> ORGANISM: Homo Sapiens

<400> SEQUENCE: 315
tgccatttgc tataaca                                                    17

<210> SEQ ID NO 316
<211> LENGTH: 17
<212> TYPE: DNA
<213> ORGANISM: Homo Sapiens

<400> SEQUENCE: 316
ccgccacacc cgctcct                                                    17

<210> SEQ ID NO 317
<211> LENGTH: 17
<212> TYPE: DNA
<213> ORGANISM: Homo Sapiens

<400> SEQUENCE: 317
ccgccacagc cgctcct                                                    17

<210> SEQ ID NO 318
<211> LENGTH: 17
<212> TYPE: DNA
<213> ORGANISM: Homo Sapiens

<400> SEQUENCE: 318
caaataatgc tagttat                                                    17

<210> SEQ ID NO 319
<211> LENGTH: 17
<212> TYPE: DNA
<213> ORGANISM: Homo Sapiens

<400> SEQUENCE: 319
caaataatgt tagttat                                                    17

<210> SEQ ID NO 320
<211> LENGTH: 17
<212> TYPE: DNA
```

```
<213> ORGANISM: Homo Sapiens

<400> SEQUENCE: 320
ggatgttgac acgctac                                                 17

<210> SEQ ID NO 321
<211> LENGTH: 17
<212> TYPE: DNA
<213> ORGANISM: Homo Sapiens

<400> SEQUENCE: 321
ggatgttgtc acgctac                                                 17

<210> SEQ ID NO 322
<211> LENGTH: 17
<212> TYPE: DNA
<213> ORGANISM: Homo Sapiens

<400> SEQUENCE: 322
catgtgtcca acgccat                                                 17

<210> SEQ ID NO 323
<211> LENGTH: 17
<212> TYPE: DNA
<213> ORGANISM: Homo Sapiens

<400> SEQUENCE: 323
catgtgtcac aacgcca                                                 17

<210> SEQ ID NO 324
<211> LENGTH: 17
<212> TYPE: DNA
<213> ORGANISM: Homo Sapiens

<400> SEQUENCE: 324 aaagggcct taaagga                                                  17

<210> SEQ ID NO 325
<211> LENGTH: 17
<212> TYPE: DNA
<213> ORGANISM: Homo Sapiens

<400> SEQUENCE: 325 aaagggctt taaagga                                                  17

<210> SEQ ID NO 326
<211> LENGTH: 17
<212> TYPE: DNA
<213> ORGANISM: Homo Sapiens

<400> SEQUENCE: 326
tgaaaagttc ttttcat                                                 17

<210> SEQ ID NO 327
<211> LENGTH: 17
<212> TYPE: DNA
<213> ORGANISM: Homo Sapiens

<400> SEQUENCE: 327
tgaaaagtac ttttcat                                                 17

<210> SEQ ID NO 328
<211> LENGTH: 17
```

```
<212> TYPE: DNA
<213> ORGANISM: Homo Sapiens

<400> SEQUENCE: 328
cctctctatg tgtgagc                                                    17

<210> SEQ ID NO 329
<211> LENGTH: 17
<212> TYPE: DNA
<213> ORGANISM: Homo Sapiens

<400> SEQUENCE: 329
cctctctacg tgtgagc                                                    17

<210> SEQ ID NO 330
<211> LENGTH: 17
<212> TYPE: DNA
<213> ORGANISM: Homo Sapiens

<400> SEQUENCE: 330
gaagttttag gattctt                                                    17

<210> SEQ ID NO 331
<211> LENGTH: 19
<212> TYPE: DNA
<213> ORGANISM: Homo Sapiens

<400> SEQUENCE: 331
gaagatttag gagagtctc                                                  19

<210> SEQ ID NO 332
<211> LENGTH: 17
<212> TYPE: DNA
<213> ORGANISM: Homo Sapiens

<400> SEQUENCE: 332
agggatgtat tttgtta                                                    17

<210> SEQ ID NO 333
<211> LENGTH: 17
<212> TYPE: DNA
<213> ORGANISM: Homo Sapiens

<400> SEQUENCE: 333
agggatgtgt tttgtta                                                    17

<210> SEQ ID NO 334
<211> LENGTH: 17
<212> TYPE: DNA
<213> ORGANISM: Homo Sapiens

<400> SEQUENCE: 334
acaattcaaa tgtatat                                                    17

<210> SEQ ID NO 335
<211> LENGTH: 17
<212> TYPE: DNA
<213> ORGANISM: Homo Sapiens

<400> SEQUENCE: 335
acaattcata tgtatat                                                    17

<210> SEQ ID NO 336
```

-continued

```
<211> LENGTH: 17
<212> TYPE: DNA
<213> ORGANISM: Homo Sapiens

<400> SEQUENCE: 336
cttgcctaac ctgcaca                                                17

<210> SEQ ID NO 337
<211> LENGTH: 17
<212> TYPE: DNA
<213> ORGANISM: Homo Sapiens

<400> SEQUENCE: 337
cttgcctagc ctgcaca                                                17

<210> SEQ ID NO 338
<211> LENGTH: 17
<212> TYPE: DNA
<213> ORGANISM: Homo Sapiens

<400> SEQUENCE: 338
caacagcacc tcatatc                                                17

<210> SEQ ID NO 339
<211> LENGTH: 17
<212> TYPE: DNA
<213> ORGANISM: Homo Sapiens

<400> SEQUENCE: 339
acagcggtgc ctcgtat                                                17

<210> SEQ ID NO 340
<211> LENGTH: 17
<212> TYPE: DNA
<213> ORGANISM: Homo Sapiens

<400> SEQUENCE: 340
actcacagtg tcagggc                                                17

<210> SEQ ID NO 341
<211> LENGTH: 17
<212> TYPE: DNA
<213> ORGANISM: Homo Sapiens

<400> SEQUENCE: 341
actcacagcg tcagggc                                                17

<210> SEQ ID NO 342
<211> LENGTH: 17
<212> TYPE: DNA
<213> ORGANISM: Homo Sapiens

<400> SEQUENCE: 342
ggctgctcct gtgtctg                                                17

<210> SEQ ID NO 343
<211> LENGTH: 19
<212> TYPE: DNA
<213> ORGANISM: Homo Sapiens

<400> SEQUENCE: 343
ggctcttcct gtgtgtctg                                              19
```

```
<210> SEQ ID NO 344
<211> LENGTH: 19
<212> TYPE: DNA
<213> ORGANISM: Homo Sapiens

<400> SEQUENCE: 344
ggctgctcct gtgtttctg                                              19

<210> SEQ ID NO 345
<211> LENGTH: 17
<212> TYPE: DNA
<213> ORGANISM: Homo Sapiens

<400> SEQUENCE: 345
aatagatgcc cttctga                                                17

<210> SEQ ID NO 346
<211> LENGTH: 17
<212> TYPE: DNA
<213> ORGANISM: Homo Sapiens

<400> SEQUENCE: 346
aatagatgcc ctcttga                                                17

<210> SEQ ID NO 347
<211> LENGTH: 17
<212> TYPE: DNA
<213> ORGANISM: Homo Sapiens

<400> SEQUENCE: 347
aatcgatgcc cttctga                                                17

<210> SEQ ID NO 348
<211> LENGTH: 17
<212> TYPE: DNA
<213> ORGANISM: Homo Sapiens

<400> SEQUENCE: 348
ttggtctagc aggtagc                                                17

<210> SEQ ID NO 349
<211> LENGTH: 17
<212> TYPE: DNA
<213> ORGANISM: Homo Sapiens

<400> SEQUENCE: 349
ttggtctacc aggtagc                                                17

<210> SEQ ID NO 350
<211> LENGTH: 17
<212> TYPE: DNA
<213> ORGANISM: Homo Sapiens

<400> SEQUENCE: 350
agccttggct cttaaaa                                                17

<210> SEQ ID NO 351
<211> LENGTH: 17
<212> TYPE: DNA
<213> ORGANISM: Homo Sapiens

<400> SEQUENCE: 351
agccttggtt cttaaaa                                                17
```

<210> SEQ ID NO 352
<211> LENGTH: 17
<212> TYPE: DNA
<213> ORGANISM: Homo Sapiens

<400> SEQUENCE: 352
agtctctggc gcctttg 17

<210> SEQ ID NO 353
<211> LENGTH: 17
<212> TYPE: DNA
<213> ORGANISM: Homo Sapiens

<400> SEQUENCE: 353
agtctctgcc gcctttg 17

<210> SEQ ID NO 354
<211> LENGTH: 19
<212> TYPE: DNA
<213> ORGANISM: Homo Sapiens

<400> SEQUENCE: 354
tagcaggagg cacagctta 19

<210> SEQ ID NO 355
<211> LENGTH: 19
<212> TYPE: DNA
<213> ORGANISM: Homo Sapiens

<400> SEQUENCE: 355
aagcaggagg cacaactta 19

<210> SEQ ID NO 356
<211> LENGTH: 19
<212> TYPE: DNA
<213> ORGANISM: Homo Sapiens

<400> SEQUENCE: 356
aagcaggagg cacagctta 19

<210> SEQ ID NO 357
<211> LENGTH: 19
<212> TYPE: DNA
<213> ORGANISM: Homo Sapiens

<400> SEQUENCE: 357
tagcaggagg cacagcttg 19

<210> SEQ ID NO 358
<211> LENGTH: 17
<212> TYPE: DNA
<213> ORGANISM: Homo Sapiens

<400> SEQUENCE: 358
aggagagacc ggactcc 17

<210> SEQ ID NO 359
<211> LENGTH: 17
<212> TYPE: DNA
<213> ORGANISM: Homo Sapiens

<400> SEQUENCE: 359
aggagagagc ggactcc 17

```
<210> SEQ ID NO 360
<211> LENGTH: 17
<212> TYPE: DNA
<213> ORGANISM: Homo Sapiens

<400> SEQUENCE: 360
tacaagtcat ccttcct                                                    17

<210> SEQ ID NO 361
<211> LENGTH: 17
<212> TYPE: DNA
<213> ORGANISM: Homo Sapiens

<400> SEQUENCE: 361
tacaagtcgt ccttcct                                                    17

<210> SEQ ID NO 362
<211> LENGTH: 17
<212> TYPE: DNA
<213> ORGANISM: Homo Sapiens

<400> SEQUENCE: 362
atacctccct cagacaa                                                    17

<210> SEQ ID NO 363
<211> LENGTH: 17
<212> TYPE: DNA
<213> ORGANISM: Homo Sapiens

<400> SEQUENCE: 363
atacctcctc agacaag                                                    17

<210> SEQ ID NO 364
<211> LENGTH: 17
<212> TYPE: DNA
<213> ORGANISM: Homo Sapiens

<400> SEQUENCE: 364
aaacaaacaa acaaacc                                                    17

<210> SEQ ID NO 365
<211> LENGTH: 17
<212> TYPE: DNA
<213> ORGANISM: Homo Sapiens

<400> SEQUENCE: 365
aaacaaacca acaaacc                                                    17

<210> SEQ ID NO 366
<211> LENGTH: 17
<212> TYPE: DNA
<213> ORGANISM: Homo Sapiens

<400> SEQUENCE: 366
gtgcgccacc atgacca                                                    17

<210> SEQ ID NO 367
<211> LENGTH: 17
<212> TYPE: DNA
<213> ORGANISM: Homo Sapiens

<400> SEQUENCE: 367
```
gtgcgccatc atgacca  17

<210> SEQ ID NO 368
<211> LENGTH: 17
<212> TYPE: DNA
<213> ORGANISM: Homo Sapiens

<400> SEQUENCE: 368
ggctttccca ttagtgg  17

<210> SEQ ID NO 369
<211> LENGTH: 17
<212> TYPE: DNA
<213> ORGANISM: Homo Sapiens

<400> SEQUENCE: 369
ggctttccta ttagtgg  17

<210> SEQ ID NO 370
<211> LENGTH: 17
<212> TYPE: DNA
<213> ORGANISM: Homo Sapiens

<400> SEQUENCE: 370
ccctcacctc tctctca  17

<210> SEQ ID NO 371
<211> LENGTH: 17
<212> TYPE: DNA
<213> ORGANISM: Homo Sapiens

<400> SEQUENCE: 371
ccctcacccc tctctca  17

<210> SEQ ID NO 372
<211> LENGTH: 17
<212> TYPE: DNA
<213> ORGANISM: Homo Sapiens

<400> SEQUENCE: 372
aatctctcgc gttcatt  17

<210> SEQ ID NO 373
<211> LENGTH: 17
<212> TYPE: DNA
<213> ORGANISM: Homo Sapiens

<400> SEQUENCE: 373
aatctctcac gttcatt  17

<210> SEQ ID NO 374
<211> LENGTH: 17
<212> TYPE: DNA
<213> ORGANISM: Homo Sapiens

<400> SEQUENCE: 374
aatgataccg atcctta  17

<210> SEQ ID NO 375
<211> LENGTH: 17
<212> TYPE: DNA
<213> ORGANISM: Homo Sapiens

<400> SEQUENCE: 375

```
aatgatacag atcctta                                                17

<210> SEQ ID NO 376
<211> LENGTH: 17
<212> TYPE: DNA
<213> ORGANISM: Homo Sapiens

<400> SEQUENCE: 376
ataaaactgc attcgtg                                                17

<210> SEQ ID NO 377
<211> LENGTH: 17
<212> TYPE: DNA
<213> ORGANISM: Homo Sapiens

<400> SEQUENCE: 377
ataaaactac attcgtg                                                17

<210> SEQ ID NO 378
<211> LENGTH: 18
<212> TYPE: DNA
<213> ORGANISM: Homo Sapiens

<400> SEQUENCE: 378
agttccagga cagccagg                                               18

<210> SEQ ID NO 379
<211> LENGTH: 17
<212> TYPE: DNA
<213> ORGANISM: Homo Sapiens

<400> SEQUENCE: 379
atatctccga ctttgaa                                                17

<210> SEQ ID NO 380
<211> LENGTH: 17
<212> TYPE: DNA
<213> ORGANISM: Homo Sapiens

<400> SEQUENCE: 380
atatctccaa ctttgaa                                                17

<210> SEQ ID NO 381
<211> LENGTH: 17
<212> TYPE: DNA
<213> ORGANISM: Homo Sapiens

<400> SEQUENCE: 381
tggccctgca gagtctg                                                17

<210> SEQ ID NO 382
<211> LENGTH: 17
<212> TYPE: DNA
<213> ORGANISM: Homo Sapiens

<400> SEQUENCE: 382
tggctctgca gagctgg                                                17

<210> SEQ ID NO 383
<211> LENGTH: 17
<212> TYPE: DNA
<213> ORGANISM: Homo Sapiens
```

-continued

```
<400> SEQUENCE: 383
caatggatca aagatgc                                                    17

<210> SEQ ID NO 384
<211> LENGTH: 17
<212> TYPE: DNA
<213> ORGANISM: Homo Sapiens

<400> SEQUENCE: 384
atggatcaac aaagatg                                                    17

<210> SEQ ID NO 385
<211> LENGTH: 17
<212> TYPE: DNA
<213> ORGANISM: Homo Sapiens

<400> SEQUENCE: 385
gctgcctcaa ggtataa                                                    17

<210> SEQ ID NO 386
<211> LENGTH: 17
<212> TYPE: DNA
<213> ORGANISM: Homo Sapiens

<400> SEQUENCE: 386
ctgcctctta aggtata                                                    17

<210> SEQ ID NO 387
<211> LENGTH: 17
<212> TYPE: DNA
<213> ORGANISM: Homo Sapiens

<400> SEQUENCE: 387
acctatggct cctcatc                                                    17

<210> SEQ ID NO 388
<211> LENGTH: 17
<212> TYPE: DNA
<213> ORGANISM: Homo Sapiens

<400> SEQUENCE: 388
acctatggtt cctcatc                                                    17

<210> SEQ ID NO 389
<211> LENGTH: 17
<212> TYPE: DNA
<213> ORGANISM: Homo Sapiens

<400> SEQUENCE: 389
tcttctcccc tgcttta                                                    17

<210> SEQ ID NO 390
<211> LENGTH: 17
<212> TYPE: DNA
<213> ORGANISM: Homo Sapiens

<400> SEQUENCE: 390
tcttctcact gctttag                                                    17

<210> SEQ ID NO 391
<211> LENGTH: 17
<212> TYPE: DNA
<213> ORGANISM: Homo Sapiens
```

-continued

```
<400> SEQUENCE: 391
ccgcataaaa agctgag                                                17

<210> SEQ ID NO 392
<211> LENGTH: 17
<212> TYPE: DNA
<213> ORGANISM: Homo Sapiens

<400> SEQUENCE: 392
ccgccataaa agctgag                                                17

<210> SEQ ID NO 393
<211> LENGTH: 17
<212> TYPE: DNA
<213> ORGANISM: Homo Sapiens

<400> SEQUENCE: 393
agaatatagg gttttttt                                               17

<210> SEQ ID NO 394
<211> LENGTH: 17
<212> TYPE: DNA
<213> ORGANISM: Homo Sapiens

<400> SEQUENCE: 394
tagaatacag ttttttt                                                17

<210> SEQ ID NO 395
<211> LENGTH: 17
<212> TYPE: DNA
<213> ORGANISM: Homo Sapiens

<400> SEQUENCE: 395
agagttgctg tgcaggg                                                17

<210> SEQ ID NO 396
<211> LENGTH: 17
<212> TYPE: DNA
<213> ORGANISM: Homo Sapiens

<400> SEQUENCE: 396
agagttgccg tgcaggg                                                17

<210> SEQ ID NO 397
<211> LENGTH: 17
<212> TYPE: DNA
<213> ORGANISM: Homo Sapiens

<400> SEQUENCE: 397
agagttgcag tgcaggg                                                17

<210> SEQ ID NO 398
<211> LENGTH: 17
<212> TYPE: DNA
<213> ORGANISM: Homo Sapiens

<400> SEQUENCE: 398
taagcagtgt tcttggc                                                17

<210> SEQ ID NO 399
<211> LENGTH: 17
<212> TYPE: DNA
```

```
<213> ORGANISM: Homo Sapiens

<400> SEQUENCE: 399
taagcagtat tcttggc                                              17

<210> SEQ ID NO 400
<211> LENGTH: 17
<212> TYPE: DNA
<213> ORGANISM: Homo Sapiens

<400> SEQUENCE: 400
tcttctcccc tgcttta                                              17

<210> SEQ ID NO 401
<211> LENGTH: 17
<212> TYPE: DNA
<213> ORGANISM: Homo Sapiens

<400> SEQUENCE: 401
tcttctcact gctttag                                              17

<210> SEQ ID NO 402
<211> LENGTH: 17
<212> TYPE: DNA
<213> ORGANISM: Homo Sapiens

<400> SEQUENCE: 402 tttttttta ttattga                                               17

<210> SEQ ID NO 403
<211> LENGTH: 17
<212> TYPE: DNA
<213> ORGANISM: Homo Sapiens

<400> SEQUENCE: 403 tttttttat tattgaa                                               17

<210> SEQ ID NO 404
<211> LENGTH: 17
<212> TYPE: DNA
<213> ORGANISM: Homo Sapiens

<400> SEQUENCE: 404
tgtggtacgc acatctg                                              17

<210> SEQ ID NO 405
<211> LENGTH: 17
<212> TYPE: DNA
<213> ORGANISM: Homo Sapiens

<400> SEQUENCE: 405
tgtggtacac acatctg                                              17

<210> SEQ ID NO 406
<211> LENGTH: 17
<212> TYPE: DNA
<213> ORGANISM: Homo Sapiens

<400> SEQUENCE: 406
agactcttag acttctg                                              17

<210> SEQ ID NO 407
<211> LENGTH: 17
```

```
<212> TYPE: DNA
<213> ORGANISM: Homo Sapiens

<400> SEQUENCE: 407
agactcttag gcttctg                                                        17

<210> SEQ ID NO 408
<211> LENGTH: 17
<212> TYPE: DNA
<213> ORGANISM: Homo Sapiens

<400> SEQUENCE: 408
agactcataa gcttctg                                                        17

<210> SEQ ID NO 409
<211> LENGTH: 17
<212> TYPE: DNA
<213> ORGANISM: Homo Sapiens

<400> SEQUENCE: 409
agactcttag gcttctg                                                        17

<210> SEQ ID NO 410
<211> LENGTH: 17
<212> TYPE: DNA
<213> ORGANISM: Homo Sapiens

<400> SEQUENCE: 410
cacgtacccg aacgtga                                                        17

<210> SEQ ID NO 411
<211> LENGTH: 17
<212> TYPE: DNA
<213> ORGANISM: Homo Sapiens

<400> SEQUENCE: 411
cacgtacctg aacgtga                                                        17

<210> SEQ ID NO 412
<211> LENGTH: 17
<212> TYPE: DNA
<213> ORGANISM: Homo Sapiens

<400> SEQUENCE: 412
attacggttt gtcgtca                                                        17

<210> SEQ ID NO 413
<211> LENGTH: 17
<212> TYPE: DNA
<213> ORGANISM: Homo Sapiens

<400> SEQUENCE: 413
attacggttg gtcgtca                                                        17

<210> SEQ ID NO 414
<211> LENGTH: 17
<212> TYPE: DNA
<213> ORGANISM: Homo Sapiens

<400> SEQUENCE: 414
ccaagatacg aaaccag                                                        17

<210> SEQ ID NO 415
```

```
<211> LENGTH: 17
<212> TYPE: DNA
<213> ORGANISM: Homo Sapiens

<400> SEQUENCE: 415
ccaagatatg aaaccag                                                    17

<210> SEQ ID NO 416
<211> LENGTH: 17
<212> TYPE: DNA
<213> ORGANISM: Homo Sapiens

<400> SEQUENCE: 416
tgcaatgacc agcaacc                                                    17

<210> SEQ ID NO 417
<211> LENGTH: 17
<212> TYPE: DNA
<213> ORGANISM: Homo Sapiens

<400> SEQUENCE: 417
tgcaacgacc agcaacc                                                    17

<210> SEQ ID NO 418
<211> LENGTH: 17
<212> TYPE: DNA
<213> ORGANISM: Homo Sapiens

<400> SEQUENCE: 418
tgtaacgacc aacaact                                                    17

<210> SEQ ID NO 419
<211> LENGTH: 17
<212> TYPE: DNA
<213> ORGANISM: Homo Sapiens

<400> SEQUENCE: 419 tctaaggga aagatgg                                                     17

<210> SEQ ID NO 420
<211> LENGTH: 17
<212> TYPE: DNA
<213> ORGANISM: Homo Sapiens

<400> SEQUENCE: 420 tctaaggaa agatgga                                                     17

<210> SEQ ID NO 421
<211> LENGTH: 17
<212> TYPE: DNA
<213> ORGANISM: Homo Sapiens

<400> SEQUENCE: 421
ctggactcat acataca                                                    17

<210> SEQ ID NO 422
<211> LENGTH: 17
<212> TYPE: DNA
<213> ORGANISM: Homo Sapiens

<400> SEQUENCE: 422
ctggactcgt acataca                                                    17
```

-continued

```
<210> SEQ ID NO 423
<211> LENGTH: 17
<212> TYPE: DNA
<213> ORGANISM: Homo Sapiens

<400> SEQUENCE: 423
agtttggtcc cctggac                                                    17

<210> SEQ ID NO 424
<211> LENGTH: 17
<212> TYPE: DNA
<213> ORGANISM: Homo Sapiens

<400> SEQUENCE: 424
agtttggttt cctggac                                                    17

<210> SEQ ID NO 425
<211> LENGTH: 17
<212> TYPE: DNA
<213> ORGANISM: Homo Sapiens

<400> SEQUENCE: 425
tatagcttca tgtaaaa                                                    17

<210> SEQ ID NO 426
<211> LENGTH: 17
<212> TYPE: DNA
<213> ORGANISM: Homo Sapiens

<400> SEQUENCE: 426
tatagcttta tgtaaaa                                                    17

<210> SEQ ID NO 427
<211> LENGTH: 17
<212> TYPE: DNA
<213> ORGANISM: Homo Sapiens

<400> SEQUENCE: 427
ttttttttat tattgaa                                                    17

<210> SEQ ID NO 428
<211> LENGTH: 17
<212> TYPE: DNA
<213> ORGANISM: Homo Sapiens

<400> SEQUENCE: 428 tttttttta ttattga                                                     17

<210> SEQ ID NO 429
<211> LENGTH: 17
<212> TYPE: DNA
<213> ORGANISM: Homo Sapiens

<400> SEQUENCE: 429
actcattgcc aatttaa                                                    17

<210> SEQ ID NO 430
<211> LENGTH: 17
<212> TYPE: DNA
<213> ORGANISM: Homo Sapiens

<400> SEQUENCE: 430
actcattcag aatttaa                                                    17
```

-continued

<210> SEQ ID NO 431
<211> LENGTH: 17
<212> TYPE: DNA
<213> ORGANISM: Homo Sapiens

<400> SEQUENCE: 431
atgcgtaatg ggggcta                                              17

<210> SEQ ID NO 432
<211> LENGTH: 17
<212> TYPE: DNA
<213> ORGANISM: Homo Sapiens

<400> SEQUENCE: 432
atgcgtaacg ggggcta                                              17

<210> SEQ ID NO 433
<211> LENGTH: 17
<212> TYPE: DNA
<213> ORGANISM: Homo Sapiens

<400> SEQUENCE: 433
ataattgctc ttttaaa                                              17

<210> SEQ ID NO 434
<211> LENGTH: 17
<212> TYPE: DNA
<213> ORGANISM: Homo Sapiens

<400> SEQUENCE: 434
gtaattgctc ttttaaa                                              17

<210> SEQ ID NO 435
<211> LENGTH: 17
<212> TYPE: DNA
<213> ORGANISM: Homo Sapiens

<400> SEQUENCE: 435
tctgattagt gatggat                                              17

<210> SEQ ID NO 436
<211> LENGTH: 17
<212> TYPE: DNA
<213> ORGANISM: Homo Sapiens

<400> SEQUENCE: 436
tctgattatg atggatt                                              17

<210> SEQ ID NO 437
<211> LENGTH: 17
<212> TYPE: DNA
<213> ORGANISM: Homo Sapiens

<400> SEQUENCE: 437
agcagagtgt ctcgtaa                                              17

<210> SEQ ID NO 438
<211> LENGTH: 17
<212> TYPE: DNA
<213> ORGANISM: Homo Sapiens

<400> SEQUENCE: 438
agcagagtat ctcgtaa                                              17

<210> SEQ ID NO 439
<211> LENGTH: 17
<212> TYPE: DNA
<213> ORGANISM: Homo Sapiens

<400> SEQUENCE: 439
gctggcagat atcggta                                              17

<210> SEQ ID NO 440
<211> LENGTH: 17
<212> TYPE: DNA
<213> ORGANISM: Homo Sapiens

<400> SEQUENCE: 440
gctggcaggt atcggta                                              17

<210> SEQ ID NO 441
<211> LENGTH: 17
<212> TYPE: DNA
<213> ORGANISM: Homo Sapiens

<400> SEQUENCE: 441
aactgcaatg accagca                                              17

<210> SEQ ID NO 442
<211> LENGTH: 17
<212> TYPE: DNA
<213> ORGANISM: Homo Sapiens

<400> SEQUENCE: 442
aactgcaacg accagca                                              17

<210> SEQ ID NO 443
<211> LENGTH: 17
<212> TYPE: DNA
<213> ORGANISM: Homo Sapiens

<400> SEQUENCE: 443
gctggtcatt gcagttt                                              17

<210> SEQ ID NO 444
<211> LENGTH: 17
<212> TYPE: DNA
<213> ORGANISM: Homo Sapiens

<400> SEQUENCE: 444
gttggtcgtt acagttt                                              17

<210> SEQ ID NO 445
<211> LENGTH: 17
<212> TYPE: DNA
<213> ORGANISM: Homo Sapiens

<400> SEQUENCE: 445
gctggtcgtt gcagttt                                              17

<210> SEQ ID NO 446
<211> LENGTH: 17
<212> TYPE: DNA
<213> ORGANISM: Homo Sapiens

<400> SEQUENCE: 446

-continued

```
gctggcagat atcggta                                      17

<210> SEQ ID NO 447
<211> LENGTH: 17
<212> TYPE: DNA
<213> ORGANISM: Homo Sapiens

<400> SEQUENCE: 447
gctggcaggt atcggta                                      17

<210> SEQ ID NO 448
<211> LENGTH: 17
<212> TYPE: DNA
<213> ORGANISM: Homo Sapiens

<400> SEQUENCE: 448
atagaaagtc caccgtc                                      17

<210> SEQ ID NO 449
<211> LENGTH: 17
<212> TYPE: DNA
<213> ORGANISM: Homo Sapiens

<400> SEQUENCE: 449
atagaaagcc caccgtc                                      17

<210> SEQ ID NO 450
<211> LENGTH: 17
<212> TYPE: DNA
<213> ORGANISM: Homo Sapiens

<400> SEQUENCE: 450
ttagtgaccg tgtaaac                                      17

<210> SEQ ID NO 451
<211> LENGTH: 17
<212> TYPE: DNA
<213> ORGANISM: Homo Sapiens

<400> SEQUENCE: 451
ttagtgactg tgtaaac                                      17

<210> SEQ ID NO 452
<211> LENGTH: 17
<212> TYPE: DNA
<213> ORGANISM: Homo Sapiens

<400> SEQUENCE: 452
ggggaggagc tttgttc                                      17

<210> SEQ ID NO 453
<211> LENGTH: 17
<212> TYPE: DNA
<213> ORGANISM: Homo Sapiens

<400> SEQUENCE: 453
ggggaggatc tttgttc                                      17

<210> SEQ ID NO 454
<211> LENGTH: 17
<212> TYPE: DNA
<213> ORGANISM: Homo Sapiens

<400> SEQUENCE: 454
```
ggcctggaca caaaagc                17

<210> SEQ ID NO 455
<211> LENGTH: 17
<212> TYPE: DNA
<213> ORGANISM: Homo Sapiens

<400> SEQUENCE: 455
ggcctggaaa caaaagc                17

<210> SEQ ID NO 456
<211> LENGTH: 17
<212> TYPE: DNA
<213> ORGANISM: Homo Sapiens

<400> SEQUENCE: 456 ccctttcta gtattgt                 17

<210> SEQ ID NO 457
<211> LENGTH: 17
<212> TYPE: DNA
<213> ORGANISM: Homo Sapiens

<400> SEQUENCE: 457 ccctttcca gtattgt                 17

<210> SEQ ID NO 458
<211> LENGTH: 17
<212> TYPE: DNA
<213> ORGANISM: Homo Sapiens

<400> SEQUENCE: 458
gaattggttt taggaat                17

<210> SEQ ID NO 459
<211> LENGTH: 17
<212> TYPE: DNA
<213> ORGANISM: Homo Sapiens

<400> SEQUENCE: 459
gaattggtat taggaat                17

<210> SEQ ID NO 460
<211> LENGTH: 17
<212> TYPE: DNA
<213> ORGANISM: Homo Sapiens

<400> SEQUENCE: 460
acccagcttt ccatggt                17

<210> SEQ ID NO 461
<211> LENGTH: 17
<212> TYPE: DNA
<213> ORGANISM: Homo Sapiens

<400> SEQUENCE: 461
acccagctct ccatggt                17

<210> SEQ ID NO 462
<211> LENGTH: 17
<212> TYPE: DNA
<213> ORGANISM: Homo Sapiens

```
<400> SEQUENCE: 462
tcacgttcgg gtacgtg                                                       17

<210> SEQ ID NO 463
<211> LENGTH: 17
<212> TYPE: DNA
<213> ORGANISM: Homo Sapiens

<400> SEQUENCE: 463
tcacgttcag gtacgtg                                                       17

<210> SEQ ID NO 464
<211> LENGTH: 17
<212> TYPE: DNA
<213> ORGANISM: Homo Sapiens

<400> SEQUENCE: 464
tgccttccgg ttggcaa                                                       17

<210> SEQ ID NO 465
<211> LENGTH: 17
<212> TYPE: DNA
<213> ORGANISM: Homo Sapiens

<400> SEQUENCE: 465
tgccttccag ttggcaa                                                       17

<210> SEQ ID NO 466
<211> LENGTH: 17
<212> TYPE: DNA
<213> ORGANISM: Homo Sapiens

<400> SEQUENCE: 466
ttttatcata caattgc                                                       17

<210> SEQ ID NO 467
<211> LENGTH: 17
<212> TYPE: DNA
<213> ORGANISM: Homo Sapiens

<400> SEQUENCE: 467
ttttatcaga caattgc                                                       17

<210> SEQ ID NO 468
<211> LENGTH: 17
<212> TYPE: DNA
<213> ORGANISM: Homo Sapiens

<400> SEQUENCE: 468
atcttctctt ctttgag                                                       17

<210> SEQ ID NO 469
<211> LENGTH: 17
<212> TYPE: DNA
<213> ORGANISM: Homo Sapiens

<400> SEQUENCE: 469
atcttctcct ctttgag                                                       17

<210> SEQ ID NO 470
<211> LENGTH: 17
<212> TYPE: DNA
<213> ORGANISM: Homo Sapiens
```

-continued

<400> SEQUENCE: 470
cagtcctctg ctttctc                      17

<210> SEQ ID NO 471
<211> LENGTH: 17
<212> TYPE: DNA
<213> ORGANISM: Homo Sapiens

<400> SEQUENCE: 471
cagtcctcag ctttctc                      17

<210> SEQ ID NO 472
<211> LENGTH: 17
<212> TYPE: DNA
<213> ORGANISM: Homo Sapiens

<400> SEQUENCE: 472
ccaagatacg aaaccag                      17

<210> SEQ ID NO 473
<211> LENGTH: 17
<212> TYPE: DNA
<213> ORGANISM: Homo Sapiens

<400> SEQUENCE: 473
ccaagatatg aaaccag                      17

<210> SEQ ID NO 474
<211> LENGTH: 17
<212> TYPE: DNA
<213> ORGANISM: Homo Sapiens

<400> SEQUENCE: 474
ggtattcaag ggttact                      17

<210> SEQ ID NO 475
<211> LENGTH: 17
<212> TYPE: DNA
<213> ORGANISM: Homo Sapiens

<400> SEQUENCE: 475
ggtattcagg gttactg                      17

<210> SEQ ID NO 476
<211> LENGTH: 17
<212> TYPE: DNA
<213> ORGANISM: Homo Sapiens

<400> SEQUENCE: 476
acctatggct cctcatc                      17

<210> SEQ ID NO 477
<211> LENGTH: 17
<212> TYPE: DNA
<213> ORGANISM: Homo Sapiens

<400> SEQUENCE: 477
acctatggtt cctcatc                      17

<210> SEQ ID NO 478
<211> LENGTH: 17
<212> TYPE: DNA

```
<213> ORGANISM: Homo Sapiens

<400> SEQUENCE: 478
ttttatcata caattgc                                              17

<210> SEQ ID NO 479
<211> LENGTH: 17
<212> TYPE: DNA
<213> ORGANISM: Homo Sapiens

<400> SEQUENCE: 479
ttttatcaga caattgc                                              17

<210> SEQ ID NO 480
<211> LENGTH: 17
<212> TYPE: DNA
<213> ORGANISM: Homo Sapiens

<400> SEQUENCE: 480
aaccagggct taagtct                                              17

<210> SEQ ID NO 481
<211> LENGTH: 17
<212> TYPE: DNA
<213> ORGANISM: Homo Sapiens

<400> SEQUENCE: 481
aaccagggat taagtct                                              17

<210> SEQ ID NO 482
<211> LENGTH: 17
<212> TYPE: DNA
<213> ORGANISM: Homo Sapiens

<400> SEQUENCE: 482
cagaaaaaca gatatac                                              17

<210> SEQ ID NO 483
<211> LENGTH: 17
<212> TYPE: DNA
<213> ORGANISM: Homo Sapiens

<400> SEQUENCE: 483
cagaaaaaga gatatac                                              17

<210> SEQ ID NO 484
<211> LENGTH: 17
<212> TYPE: DNA
<213> ORGANISM: Homo Sapiens

<400> SEQUENCE: 484
tctgagcgtg agtgctg                                              17

<210> SEQ ID NO 485
<211> LENGTH: 17
<212> TYPE: DNA
<213> ORGANISM: Homo Sapiens

<400> SEQUENCE: 485
tctgagcgcg agtgctg                                              17

<210> SEQ ID NO 486
<211> LENGTH: 17
```

-continued

```
<212> TYPE: DNA
<213> ORGANISM: Homo Sapiens

<400> SEQUENCE: 486
acctcagaag cggaggt                                              17

<210> SEQ ID NO 487
<211> LENGTH: 17
<212> TYPE: DNA
<213> ORGANISM: Homo Sapiens

<400> SEQUENCE: 487
acctcggaag gggaggt                                              17

<210> SEQ ID NO 488
<211> LENGTH: 17
<212> TYPE: DNA
<213> ORGANISM: Homo Sapiens

<400> SEQUENCE: 488
acctcggaag cggaggt                                              17

<210> SEQ ID NO 489
<211> LENGTH: 17
<212> TYPE: DNA
<213> ORGANISM: Homo Sapiens

<400> SEQUENCE: 489
taactcgatc gctatca                                              17

<210> SEQ ID NO 490
<211> LENGTH: 17
<212> TYPE: DNA
<213> ORGANISM: Homo Sapiens

<400> SEQUENCE: 490
taactcgctt gctatca                                              17

<210> SEQ ID NO 491
<211> LENGTH: 17
<212> TYPE: DNA
<213> ORGANISM: Homo Sapiens

<400> SEQUENCE: 491
taactcgctc gctatca                                              17

<210> SEQ ID NO 492
<211> LENGTH: 17
<212> TYPE: DNA
<213> ORGANISM: Homo Sapiens

<400> SEQUENCE: 492
gaatttctca acttctt                                              17

<210> SEQ ID NO 493
<211> LENGTH: 17
<212> TYPE: DNA
<213> ORGANISM: Homo Sapiens

<400> SEQUENCE: 493
gaatttctga acttctt                                              17

<210> SEQ ID NO 494
```

```
<211> LENGTH: 17
<212> TYPE: DNA
<213> ORGANISM: Homo Sapiens

<400> SEQUENCE: 494 cagggtccc caatttg                                                   17

<210> SEQ ID NO 495
<211> LENGTH: 17
<212> TYPE: DNA
<213> ORGANISM: Homo Sapiens

<400> SEQUENCE: 495 cagggtctc caatttg                                                   17

<210> SEQ ID NO 496
<211> LENGTH: 17
<212> TYPE: DNA
<213> ORGANISM: Homo Sapiens

<400> SEQUENCE: 496
ttttgctgtg caggcta                                                  17

<210> SEQ ID NO 497
<211> LENGTH: 17
<212> TYPE: DNA
<213> ORGANISM: Homo Sapiens

<400> SEQUENCE: 497
ttttactgtg ccaggct                                                  17

<210> SEQ ID NO 498
<211> LENGTH: 17
<212> TYPE: DNA
<213> ORGANISM: Homo Sapiens

<400> SEQUENCE: 498
gacagccctg tctcaaa                                                  17

<210> SEQ ID NO 499
<211> LENGTH: 17
<212> TYPE: DNA
<213> ORGANISM: Homo Sapiens

<400> SEQUENCE: 499
agagaaaccc tgtctca                                                  17

<210> SEQ ID NO 500
<211> LENGTH: 17
<212> TYPE: DNA
<213> ORGANISM: Homo Sapiens

<400> SEQUENCE: 500
gcaccggtct gagcagt                                                  17

<210> SEQ ID NO 501
<211> LENGTH: 17
<212> TYPE: DNA
<213> ORGANISM: Homo Sapiens

<400> SEQUENCE: 501
gcaccggttt gagcagt                                                  17
```

<210> SEQ ID NO 502
<211> LENGTH: 17
<212> TYPE: DNA
<213> ORGANISM: Homo Sapiens

<400> SEQUENCE: 502
ccgtgcccct gaacaat                                                    17

<210> SEQ ID NO 503
<211> LENGTH: 17
<212> TYPE: DNA
<213> ORGANISM: Homo Sapiens

<400> SEQUENCE: 503
ccgtgccctt gaacaat                                                    17

<210> SEQ ID NO 504
<211> LENGTH: 17
<212> TYPE: DNA
<213> ORGANISM: Homo Sapiens

<400> SEQUENCE: 504
tcacgttcgg gtacgtg                                                    17

<210> SEQ ID NO 505
<211> LENGTH: 17
<212> TYPE: DNA
<213> ORGANISM: Homo Sapiens

<400> SEQUENCE: 505
tcacgttcag gtacgtg                                                    17

<210> SEQ ID NO 506
<211> LENGTH: 17
<212> TYPE: DNA
<213> ORGANISM: Homo Sapiens

<400> SEQUENCE: 506
tgattcgctg ggactct                                                    17

<210> SEQ ID NO 507
<211> LENGTH: 17
<212> TYPE: DNA
<213> ORGANISM: Homo Sapiens

<400> SEQUENCE: 507
tgattcgccg ggactct                                                    17

<210> SEQ ID NO 508
<211> LENGTH: 17
<212> TYPE: DNA
<213> ORGANISM: Homo Sapiens

<400> SEQUENCE: 508
ttgatatccg aggcctt                                                    17

<210> SEQ ID NO 509
<211> LENGTH: 17
<212> TYPE: DNA
<213> ORGANISM: Homo Sapiens

<400> SEQUENCE: 509
ttgatatctg aggcctt                                                    17

```
<210> SEQ ID NO 510
<211> LENGTH: 17
<212> TYPE: DNA
<213> ORGANISM: Homo Sapiens

<400> SEQUENCE: 510
tccctgggcc aagcata                                                  17

<210> SEQ ID NO 511
<211> LENGTH: 17
<212> TYPE: DNA
<213> ORGANISM: Homo Sapiens

<400> SEQUENCE: 511
tccctgggtc aagcata                                                  17

<210> SEQ ID NO 512
<211> LENGTH: 17
<212> TYPE: DNA
<213> ORGANISM: Homo Sapiens

<400> SEQUENCE: 512
ttatggctga ggatcac                                                  17

<210> SEQ ID NO 513
<211> LENGTH: 17
<212> TYPE: DNA
<213> ORGANISM: Homo Sapiens

<400> SEQUENCE: 513
ttatggctgc ggatcat                                                  17

<210> SEQ ID NO 514
<211> LENGTH: 17
<212> TYPE: DNA
<213> ORGANISM: Homo Sapiens

<400> SEQUENCE: 514
ttatggcagg ggatcac                                                  17

<210> SEQ ID NO 515
<211> LENGTH: 17
<212> TYPE: DNA
<213> ORGANISM: Homo Sapiens

<400> SEQUENCE: 515
ctctctgcgc tgaagca                                                  17

<210> SEQ ID NO 516
<211> LENGTH: 17
<212> TYPE: DNA
<213> ORGANISM: Homo Sapiens

<400> SEQUENCE: 516
ctctctgctc tgaagca                                                  17

<210> SEQ ID NO 517
<211> LENGTH: 17
<212> TYPE: DNA
<213> ORGANISM: Homo Sapiens

<400> SEQUENCE: 517
agatacagag atgtgtt                                                  17
```

<210> SEQ ID NO 518
<211> LENGTH: 17
<212> TYPE: DNA
<213> ORGANISM: Homo Sapiens

<400> SEQUENCE: 518
agatactgag gtgtgtt                                                17

<210> SEQ ID NO 519
<211> LENGTH: 17
<212> TYPE: DNA
<213> ORGANISM: Homo Sapiens

<400> SEQUENCE: 519
cgacatctgg cagatgt                                                17

<210> SEQ ID NO 520
<211> LENGTH: 17
<212> TYPE: DNA
<213> ORGANISM: Homo Sapiens

<400> SEQUENCE: 520
cgacatctag cagatgt                                                17

<210> SEQ ID NO 521
<211> LENGTH: 17
<212> TYPE: DNA
<213> ORGANISM: Homo Sapiens

<400> SEQUENCE: 521
gtcacaaata gtatttc                                                17

<210> SEQ ID NO 522
<211> LENGTH: 17
<212> TYPE: DNA
<213> ORGANISM: Homo Sapiens

<400> SEQUENCE: 522
gtcacaaaga gtatttc                                                17

<210> SEQ ID NO 523
<211> LENGTH: 17
<212> TYPE: DNA
<213> ORGANISM: Homo Sapiens

<400> SEQUENCE: 523
aaggtgtgtg cgtgtgt                                                17

<210> SEQ ID NO 524
<211> LENGTH: 17
<212> TYPE: DNA
<213> ORGANISM: Homo Sapiens

<400> SEQUENCE: 524
aaggtgtgcg cgtgtgt                                                17

<210> SEQ ID NO 525
<211> LENGTH: 17
<212> TYPE: DNA
<213> ORGANISM: Homo Sapiens

<400> SEQUENCE: 525

-continued agtcttttt ttcctga                          17

<210> SEQ ID NO 526
<211> LENGTH: 19
<212> TYPE: DNA
<213> ORGANISM: Homo Sapiens

<400> SEQUENCE: 526 tagtctttttt tttcctgaa                      19

<210> SEQ ID NO 527
<211> LENGTH: 17
<212> TYPE: DNA
<213> ORGANISM: Homo Sapiens

<400> SEQUENCE: 527
caggctgtgg gaggctt                         17

<210> SEQ ID NO 528
<211> LENGTH: 17
<212> TYPE: DNA
<213> ORGANISM: Homo Sapiens

<400> SEQUENCE: 528
caggctgcgg aaggctt                         17

<210> SEQ ID NO 529
<211> LENGTH: 17
<212> TYPE: DNA
<213> ORGANISM: Homo Sapiens

<400> SEQUENCE: 529
ctgtaagtca ttcaata                         17

<210> SEQ ID NO 530
<211> LENGTH: 17
<212> TYPE: DNA
<213> ORGANISM: Homo Sapiens

<400> SEQUENCE: 530
ctgtaagtaa ttcaata                         17

<210> SEQ ID NO 531
<211> LENGTH: 17
<212> TYPE: DNA
<213> ORGANISM: Homo Sapiens

<400> SEQUENCE: 531 cagggtccc caatttg                          17

<210> SEQ ID NO 532
<211> LENGTH: 17
<212> TYPE: DNA
<213> ORGANISM: Homo Sapiens

<400> SEQUENCE: 532 cagggtctc caatttg                          17

<210> SEQ ID NO 533
<211> LENGTH: 17
<212> TYPE: DNA
<213> ORGANISM: Homo Sapiens

<400> SEQUENCE: 533

-continued gactcatggc cgccttg                                                17

<210> SEQ ID NO 534
<211> LENGTH: 17
<212> TYPE: DNA
<213> ORGANISM: Homo Sapiens

<400> SEQUENCE: 534
gactcattgc cgcctgg                                                17

<210> SEQ ID NO 535
<211> LENGTH: 17
<212> TYPE: DNA
<213> ORGANISM: Homo Sapiens

<400> SEQUENCE: 535
gactcctggc cgcctgg                                                17

<210> SEQ ID NO 536
<211> LENGTH: 17
<212> TYPE: DNA
<213> ORGANISM: Homo Sapiens

<400> SEQUENCE: 536
gactcctggc tgcctgg                                                17

<210> SEQ ID NO 537
<211> LENGTH: 17
<212> TYPE: DNA
<213> ORGANISM: Homo Sapiens

<400> SEQUENCE: 537
gactcctggc cgcctgg                                                17

<210> SEQ ID NO 538
<211> LENGTH: 17
<212> TYPE: DNA
<213> ORGANISM: Homo Sapiens

<400> SEQUENCE: 538
acaggggagg aaggaag                                                17

<210> SEQ ID NO 539
<211> LENGTH: 17
<212> TYPE: DNA
<213> ORGANISM: Homo Sapiens

<400> SEQUENCE: 539
acaggggaag gaaggaa                                                17

<210> SEQ ID NO 540
<211> LENGTH: 17
<212> TYPE: DNA
<213> ORGANISM: Homo Sapiens

<400> SEQUENCE: 540
ttgatataga ttgattc                                                17

<210> SEQ ID NO 541
<211> LENGTH: 17
<212> TYPE: DNA
<213> ORGANISM: Homo Sapiens

```
<400> SEQUENCE: 541
ttgatatata ttgattc                                                17

<210> SEQ ID NO 542
<211> LENGTH: 17
<212> TYPE: DNA
<213> ORGANISM: Homo Sapiens

<400> SEQUENCE: 542
atagaacagc aaagtaa                                                17

<210> SEQ ID NO 543
<211> LENGTH: 17
<212> TYPE: DNA
<213> ORGANISM: Homo Sapiens

<400> SEQUENCE: 543
atagaacaac aaagtaa                                                17

<210> SEQ ID NO 544
<211> LENGTH: 17
<212> TYPE: DNA
<213> ORGANISM: Homo Sapiens

<400> SEQUENCE: 544
aacaagcatc tatggat                                                17

<210> SEQ ID NO 545
<211> LENGTH: 17
<212> TYPE: DNA
<213> ORGANISM: Homo Sapiens

<400> SEQUENCE: 545
aacaagcacc tatggat                                                17

<210> SEQ ID NO 546
<211> LENGTH: 17
<212> TYPE: DNA
<213> ORGANISM: Homo Sapiens

<400> SEQUENCE: 546
gagcaggtta agcgatg                                                17

<210> SEQ ID NO 547
<211> LENGTH: 17
<212> TYPE: DNA
<213> ORGANISM: Homo Sapiens

<400> SEQUENCE: 547
gagcaggtga agcgatg                                                17

<210> SEQ ID NO 548
<211> LENGTH: 17
<212> TYPE: DNA
<213> ORGANISM: Homo Sapiens

<400> SEQUENCE: 548
ggcttccagc ttgattc                                                17

<210> SEQ ID NO 549
<211> LENGTH: 17
<212> TYPE: DNA
<213> ORGANISM: Homo Sapiens
```

```
<400> SEQUENCE: 549
ggcttccaac ttgattc                                                17

<210> SEQ ID NO 550
<211> LENGTH: 17
<212> TYPE: DNA
<213> ORGANISM: Homo Sapiens

<400> SEQUENCE: 550
agatagggat gaatccc                                                17

<210> SEQ ID NO 551
<211> LENGTH: 17
<212> TYPE: DNA
<213> ORGANISM: Homo Sapiens

<400> SEQUENCE: 551 agatagggt gaatccc                                                 17

<210> SEQ ID NO 552
<211> LENGTH: 17
<212> TYPE: DNA
<213> ORGANISM: Homo Sapiens

<400> SEQUENCE: 552
tcattcaccg tttattg                                                17

<210> SEQ ID NO 553
<211> LENGTH: 17
<212> TYPE: DNA
<213> ORGANISM: Homo Sapiens

<400> SEQUENCE: 553
tcattcactg tttattg                                                17

<210> SEQ ID NO 554
<211> LENGTH: 17
<212> TYPE: DNA
<213> ORGANISM: Homo Sapiens

<400> SEQUENCE: 554
ctgacatact gcttagg                                                17

<210> SEQ ID NO 555
<211> LENGTH: 17
<212> TYPE: DNA
<213> ORGANISM: Homo Sapiens

<400> SEQUENCE: 555
ctgacatatt gcttagg                                                17

<210> SEQ ID NO 556
<211> LENGTH: 17
<212> TYPE: DNA
<213> ORGANISM: Homo Sapiens

<400> SEQUENCE: 556
ctaggaaagc ctaaatt                                                17

<210> SEQ ID NO 557
<211> LENGTH: 17
<212> TYPE: DNA
```

```
<213> ORGANISM: Homo Sapiens

<400> SEQUENCE: 557
ctaggaaaac ctaaatt                                              17

<210> SEQ ID NO 558
<211> LENGTH: 17
<212> TYPE: DNA
<213> ORGANISM: Homo Sapiens

<400> SEQUENCE: 558
atgtcaggat tttaaga                                              17

<210> SEQ ID NO 559
<211> LENGTH: 17
<212> TYPE: DNA
<213> ORGANISM: Homo Sapiens

<400> SEQUENCE: 559
atgtcagggt tttaaga                                              17

<210> SEQ ID NO 560
<211> LENGTH: 17
<212> TYPE: DNA
<213> ORGANISM: Homo Sapiens

<400> SEQUENCE: 560
ggtttccaat tggaaag                                              17

<210> SEQ ID NO 561
<211> LENGTH: 17
<212> TYPE: DNA
<213> ORGANISM: Homo Sapiens

<400> SEQUENCE: 561
ggtttccagt tggaaag                                              17

<210> SEQ ID NO 562
<211> LENGTH: 17
<212> TYPE: DNA
<213> ORGANISM: Homo Sapiens

<400> SEQUENCE: 562
cgaggagtgc aaagcga                                              17

<210> SEQ ID NO 563
<211> LENGTH: 17
<212> TYPE: DNA
<213> ORGANISM: Homo Sapiens

<400> SEQUENCE: 563
cgaggagtcc aaagcga                                              17

<210> SEQ ID NO 564
<211> LENGTH: 17
<212> TYPE: DNA
<213> ORGANISM: Homo Sapiens

<400> SEQUENCE: 564
tgtgtgtgtg tctgtct                                              17

<210> SEQ ID NO 565
<211> LENGTH: 17
```

```
<212> TYPE: DNA
<213> ORGANISM: Homo Sapiens

<400> SEQUENCE: 565
tgtgtgtgcg tctgtct                                              17

<210> SEQ ID NO 566
<211> LENGTH: 17
<212> TYPE: DNA
<213> ORGANISM: Homo Sapiens

<400> SEQUENCE: 566
gcaagatgca gctgcat                                              17

<210> SEQ ID NO 567
<211> LENGTH: 17
<212> TYPE: DNA
<213> ORGANISM: Homo Sapiens

<400> SEQUENCE: 567
gcaagatgta gctgcat                                              17

<210> SEQ ID NO 568
<211> LENGTH: 17
<212> TYPE: DNA
<213> ORGANISM: Homo Sapiens

<400> SEQUENCE: 568
gctggggcta ttctgta                                              17

<210> SEQ ID NO 569
<211> LENGTH: 17
<212> TYPE: DNA
<213> ORGANISM: Homo Sapiens

<400> SEQUENCE: 569
gctggggcca ttctgta                                              17

<210> SEQ ID NO 570
<211> LENGTH: 17
<212> TYPE: DNA
<213> ORGANISM: Homo Sapiens

<400> SEQUENCE: 570
caataacgga cctgcct                                              17

<210> SEQ ID NO 571
<211> LENGTH: 17
<212> TYPE: DNA
<213> ORGANISM: Homo Sapiens

<400> SEQUENCE: 571
caataacgaa cctgcct                                              17

<210> SEQ ID NO 572
<211> LENGTH: 17
<212> TYPE: DNA
<213> ORGANISM: Homo Sapiens

<400> SEQUENCE: 572
tagcctctct acatagg                                              17

<210> SEQ ID NO 573
```

-continued

```
<211> LENGTH: 17
<212> TYPE: DNA
<213> ORGANISM: Homo Sapiens

<400> SEQUENCE: 573
tagcctctgt acatagg                                                    17

<210> SEQ ID NO 574
<211> LENGTH: 17
<212> TYPE: DNA
<213> ORGANISM: Homo Sapiens

<400> SEQUENCE: 574
catctatagg ttcactt                                                    17

<210> SEQ ID NO 575
<211> LENGTH: 17
<212> TYPE: DNA
<213> ORGANISM: Homo Sapiens

<400> SEQUENCE: 575
catctatatg ttcactt                                                    17

<210> SEQ ID NO 576
<211> LENGTH: 17
<212> TYPE: DNA
<213> ORGANISM: Homo Sapiens

<400> SEQUENCE: 576
gccaacaaca ttgagag                                                    17

<210> SEQ ID NO 577
<211> LENGTH: 17
<212> TYPE: DNA
<213> ORGANISM: Homo Sapiens

<400> SEQUENCE: 577
gccaacaaga ttgagag                                                    17

<210> SEQ ID NO 578
<211> LENGTH: 17
<212> TYPE: DNA
<213> ORGANISM: Homo Sapiens

<400> SEQUENCE: 578
gggtcgtgcg tccccct                                                    17

<210> SEQ ID NO 579
<211> LENGTH: 17
<212> TYPE: DNA
<213> ORGANISM: Homo Sapiens

<400> SEQUENCE: 579
gggtcgtgtg tccccct                                                    17

<210> SEQ ID NO 580
<211> LENGTH: 17
<212> TYPE: DNA
<213> ORGANISM: Homo Sapiens

<400> SEQUENCE: 580
attgtctcac atttctt                                                    17
```

```
<210> SEQ ID NO 581
<211> LENGTH: 17
<212> TYPE: DNA
<213> ORGANISM: Homo Sapiens

<400> SEQUENCE: 581
attgtctcgc atttctt                                                    17

<210> SEQ ID NO 582
<211> LENGTH: 17
<212> TYPE: DNA
<213> ORGANISM: Homo Sapiens

<400> SEQUENCE: 582
ggtgtggtcg cagaagg                                                    17

<210> SEQ ID NO 583
<211> LENGTH: 17
<212> TYPE: DNA
<213> ORGANISM: Homo Sapiens

<400> SEQUENCE: 583
ggtgtggttg cagaagg                                                    17

<210> SEQ ID NO 584
<211> LENGTH: 17
<212> TYPE: DNA
<213> ORGANISM: Homo Sapiens

<400> SEQUENCE: 584
tcattgccac acttgaa                                                    17

<210> SEQ ID NO 585
<211> LENGTH: 17
<212> TYPE: DNA
<213> ORGANISM: Homo Sapiens

<400> SEQUENCE: 585
tcattgccgc acttgaa                                                    17

<210> SEQ ID NO 586
<211> LENGTH: 17
<212> TYPE: DNA
<213> ORGANISM: Homo Sapiens

<400> SEQUENCE: 586
atctgtctac aatgatc                                                    17

<210> SEQ ID NO 587
<211> LENGTH: 17
<212> TYPE: DNA
<213> ORGANISM: Homo Sapiens

<400> SEQUENCE: 587
atctgtctgc aatgatc                                                    17

<210> SEQ ID NO 588
<211> LENGTH: 17
<212> TYPE: DNA
<213> ORGANISM: Homo Sapiens

<400> SEQUENCE: 588
ggctgggcac agtggct                                                    17
```

<210> SEQ ID NO 589
<211> LENGTH: 17
<212> TYPE: DNA
<213> ORGANISM: Homo Sapiens

<400> SEQUENCE: 589
ggctgggcgc agtggct                                                17

<210> SEQ ID NO 590
<211> LENGTH: 17
<212> TYPE: DNA
<213> ORGANISM: Homo Sapiens

<400> SEQUENCE: 590
cagcctggag aacaagt                                                17

<210> SEQ ID NO 591
<211> LENGTH: 17
<212> TYPE: DNA
<213> ORGANISM: Homo Sapiens

<400> SEQUENCE: 591
cagcctggcg aacaagt                                                17

<210> SEQ ID NO 592
<211> LENGTH: 17
<212> TYPE: DNA
<213> ORGANISM: Homo Sapiens

<400> SEQUENCE: 592
tttgacaccc ggaagct                                                17

<210> SEQ ID NO 593
<211> LENGTH: 17
<212> TYPE: DNA
<213> ORGANISM: Homo Sapiens

<400> SEQUENCE: 593
tttgacactc ggaagct                                                17

<210> SEQ ID NO 594
<211> LENGTH: 17
<212> TYPE: DNA
<213> ORGANISM: Homo Sapiens

<400> SEQUENCE: 594
ctgcctttca tactgcc                                                17

<210> SEQ ID NO 595
<211> LENGTH: 17
<212> TYPE: DNA
<213> ORGANISM: Homo Sapiens

<400> SEQUENCE: 595
ctgcctttta tactgcc                                                17

<210> SEQ ID NO 596
<211> LENGTH: 17
<212> TYPE: DNA
<213> ORGANISM: Homo Sapiens

<400> SEQUENCE: 596
acaatagacg ttccccg                                                17

-continued

<210> SEQ ID NO 597
<211> LENGTH: 17
<212> TYPE: DNA
<213> ORGANISM: Homo Sapiens

<400> SEQUENCE: 597
acaatagatg ttccccg                                                17

<210> SEQ ID NO 598
<211> LENGTH: 17
<212> TYPE: DNA
<213> ORGANISM: Homo Sapiens

<400> SEQUENCE: 598
ggtgtttgat ttgtact                                                17

<210> SEQ ID NO 599
<211> LENGTH: 17
<212> TYPE: DNA
<213> ORGANISM: Homo Sapiens

<400> SEQUENCE: 599
ggtgtttgct ttgtact                                                17

<210> SEQ ID NO 600
<211> LENGTH: 17
<212> TYPE: DNA
<213> ORGANISM: Homo Sapiens

<400> SEQUENCE: 600
tccaactcaa aaaatgt                                                17

<210> SEQ ID NO 601
<211> LENGTH: 17
<212> TYPE: DNA
<213> ORGANISM: Homo Sapiens

<400> SEQUENCE: 601
tccaactcta aaaatgt                                                17

<210> SEQ ID NO 602
<211> LENGTH: 17
<212> TYPE: DNA
<213> ORGANISM: Homo Sapiens

<400> SEQUENCE: 602
gggccgctca cagtcca                                                17

<210> SEQ ID NO 603
<211> LENGTH: 17
<212> TYPE: DNA
<213> ORGANISM: Homo Sapiens

<400> SEQUENCE: 603
gggccgctta cagtcca                                                17

<210> SEQ ID NO 604
<211> LENGTH: 17
<212> TYPE: DNA
<213> ORGANISM: Homo Sapiens

<400> SEQUENCE: 604

-continued gcatggctcg tgggttt 17

<210> SEQ ID NO 605
<211> LENGTH: 17
<212> TYPE: DNA
<213> ORGANISM: Homo Sapiens

<400> SEQUENCE: 605
gcatggcttg tgggttt 17

<210> SEQ ID NO 606
<211> LENGTH: 17
<212> TYPE: DNA
<213> ORGANISM: Homo Sapiens

<400> SEQUENCE: 606
gttgggaagt ggagcgg 17

<210> SEQ ID NO 607
<211> LENGTH: 17
<212> TYPE: DNA
<213> ORGANISM: Homo Sapiens

<400> SEQUENCE: 607
gttgggaatt ggagcgg 17

<210> SEQ ID NO 608
<211> LENGTH: 17
<212> TYPE: DNA
<213> ORGANISM: Homo Sapiens

<400> SEQUENCE: 608
aagggatgag gatgtga 17

<210> SEQ ID NO 609
<211> LENGTH: 17
<212> TYPE: DNA
<213> ORGANISM: Homo Sapiens

<400> SEQUENCE: 609
aagggatggg gatgtga 17

<210> SEQ ID NO 610
<211> LENGTH: 17
<212> TYPE: DNA
<213> ORGANISM: Homo Sapiens

<400> SEQUENCE: 610
tcctcgagag ctttgct 17

<210> SEQ ID NO 611
<211> LENGTH: 17
<212> TYPE: DNA
<213> ORGANISM: Homo Sapiens

<400> SEQUENCE: 611
tcctcgaggg ctttgct 17

<210> SEQ ID NO 612
<211> LENGTH: 17
<212> TYPE: DNA
<213> ORGANISM: Homo Sapiens

<400> SEQUENCE: 612
tgacaatgcg tgcccaa                                                    17

<210> SEQ ID NO 613
<211> LENGTH: 17
<212> TYPE: DNA
<213> ORGANISM: Homo Sapiens

<400> SEQUENCE: 613
tgacaatgtg tgcccaa                                                    17

<210> SEQ ID NO 614
<211> LENGTH: 17
<212> TYPE: DNA
<213> ORGANISM: Homo Sapiens

<400> SEQUENCE: 614
tccatgtcat agatttc                                                    17

<210> SEQ ID NO 615
<211> LENGTH: 17
<212> TYPE: DNA
<213> ORGANISM: Homo Sapiens

<400> SEQUENCE: 615
tccatgtcgt agatttc                                                    17

<210> SEQ ID NO 616
<211> LENGTH: 17
<212> TYPE: DNA
<213> ORGANISM: Homo Sapiens

<400> SEQUENCE: 616
tggaggacag tggaggg                                                    17

<210> SEQ ID NO 617
<211> LENGTH: 17
<212> TYPE: DNA
<213> ORGANISM: Homo Sapiens

<400> SEQUENCE: 617
tggaggactg tggaggg                                                    17

<210> SEQ ID NO 618
<211> LENGTH: 17
<212> TYPE: DNA
<213> ORGANISM: Homo Sapiens

<400> SEQUENCE: 618
acccatttcc tgaaaat                                                    17

<210> SEQ ID NO 619
<211> LENGTH: 17
<212> TYPE: DNA
<213> ORGANISM: Homo Sapiens

<400> SEQUENCE: 619
acccattttc tgaaaat                                                    17

<210> SEQ ID NO 620
<211> LENGTH: 17
<212> TYPE: DNA
<213> ORGANISM: Homo Sapiens

```
<400> SEQUENCE: 620
ctgagttcgg cactgct                                              17

<210> SEQ ID NO 621
<211> LENGTH: 17
<212> TYPE: DNA
<213> ORGANISM: Homo Sapiens

<400> SEQUENCE: 621
ctgagttctg cactgct                                              17

<210> SEQ ID NO 622
<211> LENGTH: 17
<212> TYPE: DNA
<213> ORGANISM: Homo Sapiens

<400> SEQUENCE: 622
accagtttgg ctcaaag                                              17

<210> SEQ ID NO 623
<211> LENGTH: 17
<212> TYPE: DNA
<213> ORGANISM: Homo Sapiens

<400> SEQUENCE: 623
accagttttg ctcaaag                                              17

<210> SEQ ID NO 624
<211> LENGTH: 17
<212> TYPE: DNA
<213> ORGANISM: Homo Sapiens

<400> SEQUENCE: 624
ccaatcagaa cgtgcag                                              17

<210> SEQ ID NO 625
<211> LENGTH: 17
<212> TYPE: DNA
<213> ORGANISM: Homo Sapiens

<400> SEQUENCE: 625
ccaatcagag cgtgcag                                              17

<210> SEQ ID NO 626
<211> LENGTH: 17
<212> TYPE: DNA
<213> ORGANISM: Homo Sapiens

<400> SEQUENCE: 626
acccacacag acactgc                                              17

<210> SEQ ID NO 627
<211> LENGTH: 17
<212> TYPE: DNA
<213> ORGANISM: Homo Sapiens

<400> SEQUENCE: 627
acccacactg acactgc                                              17

<210> SEQ ID NO 628
<211> LENGTH: 17
<212> TYPE: DNA
<213> ORGANISM: Homo Sapiens
```

```
<400> SEQUENCE: 628
ggacaaagcg ctggtgt                                                  17

<210> SEQ ID NO 629
<211> LENGTH: 17
<212> TYPE: DNA
<213> ORGANISM: Homo Sapiens

<400> SEQUENCE: 629
ggacaaagtg ctggtgt                                                  17

<210> SEQ ID NO 630
<211> LENGTH: 17
<212> TYPE: DNA
<213> ORGANISM: Homo Sapiens

<400> SEQUENCE: 630
agctggtccc cctmccc                                                  17

<210> SEQ ID NO 631
<211> LENGTH: 17
<212> TYPE: DNA
<213> ORGANISM: Homo Sapiens

<400> SEQUENCE: 631
agctggtctc cctmccc                                                  17

<210> SEQ ID NO 632
<211> LENGTH: 17
<212> TYPE: DNA
<213> ORGANISM: Homo Sapiens

<400> SEQUENCE: 632
ggtgtagtaa gcacagc                                                  17

<210> SEQ ID NO 633
<211> LENGTH: 17
<212> TYPE: DNA
<213> ORGANISM: Homo Sapiens

<400> SEQUENCE: 633
ggtgtagtca gcacagc                                                  17

<210> SEQ ID NO 634
<211> LENGTH: 17
<212> TYPE: DNA
<213> ORGANISM: Homo Sapiens

<400> SEQUENCE: 634
agcgaacacg ggggaaa                                                  17

<210> SEQ ID NO 635
<211> LENGTH: 17
<212> TYPE: DNA
<213> ORGANISM: Homo Sapiens

<400> SEQUENCE: 635
agcgaacatg ggggaaa                                                  17

<210> SEQ ID NO 636
<211> LENGTH: 17
<212> TYPE: DNA
```

<213> ORGANISM: Homo Sapiens

<400> SEQUENCE: 636
gtgacagcac caaactt                                                    17

<210> SEQ ID NO 637
<211> LENGTH: 17
<212> TYPE: DNA
<213> ORGANISM: Homo Sapiens

<400> SEQUENCE: 637
gtgacagcgc caaactt                                                    17

<210> SEQ ID NO 638
<211> LENGTH: 17
<212> TYPE: DNA
<213> ORGANISM: Homo Sapiens

<400> SEQUENCE: 638
gtctgttgct gttattt                                                    17

<210> SEQ ID NO 639
<211> LENGTH: 17
<212> TYPE: DNA
<213> ORGANISM: Homo Sapiens

<400> SEQUENCE: 639
gtctgttgtt gttattt                                                    17

<210> SEQ ID NO 640
<211> LENGTH: 17
<212> TYPE: DNA
<213> ORGANISM: Homo Sapiens

<400> SEQUENCE: 640
accagcatag cccagag                                                    17

<210> SEQ ID NO 641
<211> LENGTH: 17
<212> TYPE: DNA
<213> ORGANISM: Homo Sapiens

<400> SEQUENCE: 641
accagcatgg cccagag                                                    17

<210> SEQ ID NO 642
<211> LENGTH: 17
<212> TYPE: DNA
<213> ORGANISM: Homo Sapiens

<400> SEQUENCE: 642
cgtaggagac aagacct                                                    17

<210> SEQ ID NO 643
<211> LENGTH: 17
<212> TYPE: DNA
<213> ORGANISM: Homo Sapiens

<400> SEQUENCE: 643
cgtaggaggc aagacct                                                    17

<210> SEQ ID NO 644
<211> LENGTH: 17

```
<212> TYPE: DNA
<213> ORGANISM: Homo Sapiens

<400> SEQUENCE: 644
ctctgctgaa tctccca                                                    17

<210> SEQ ID NO 645
<211> LENGTH: 17
<212> TYPE: DNA
<213> ORGANISM: Homo Sapiens

<400> SEQUENCE: 645
ctctgctgga tctccca                                                    17

<210> SEQ ID NO 646
<211> LENGTH: 17
<212> TYPE: DNA
<213> ORGANISM: Homo Sapiens

<400> SEQUENCE: 646
aagcaaagac tgattca                                                    17

<210> SEQ ID NO 647
<211> LENGTH: 17
<212> TYPE: DNA
<213> ORGANISM: Homo Sapiens

<400> SEQUENCE: 647
aagcaaagtc tgattca                                                    17

<210> SEQ ID NO 648
<211> LENGTH: 17
<212> TYPE: DNA
<213> ORGANISM: Homo Sapiens

<400> SEQUENCE: 648
aggcagctag agggaga                                                    17

<210> SEQ ID NO 649
<211> LENGTH: 17
<212> TYPE: DNA
<213> ORGANISM: Homo Sapiens

<400> SEQUENCE: 649
aggcagctcg agggaga                                                    17

<210> SEQ ID NO 650
<211> LENGTH: 17
<212> TYPE: DNA
<213> ORGANISM: Homo Sapiens

<400> SEQUENCE: 650
ttccattccg ttcaatt                                                    17

<210> SEQ ID NO 651
<211> LENGTH: 17
<212> TYPE: DNA
<213> ORGANISM: Homo Sapiens

<400> SEQUENCE: 651
ttccattctg ttcaatt                                                    17

<210> SEQ ID NO 652
```

-continued

```
<211> LENGTH: 17
<212> TYPE: DNA
<213> ORGANISM: Homo Sapiens

<400> SEQUENCE: 652
tattgttact gattttg                                                    17

<210> SEQ ID NO 653
<211> LENGTH: 17
<212> TYPE: DNA
<213> ORGANISM: Homo Sapiens

<400> SEQUENCE: 653
tattgttatt gattttg                                                    17

<210> SEQ ID NO 654
<211> LENGTH: 17
<212> TYPE: DNA
<213> ORGANISM: Homo Sapiens

<400> SEQUENCE: 654
gagctttcag aggctga                                                    17

<210> SEQ ID NO 655
<211> LENGTH: 17
<212> TYPE: DNA
<213> ORGANISM: Homo Sapiens

<400> SEQUENCE: 655
gagctttcgg aggctga                                                    17

<210> SEQ ID NO 656
<211> LENGTH: 17
<212> TYPE: DNA
<213> ORGANISM: Homo Sapiens

<400> SEQUENCE: 656
gggggaagat atggagt                                                    17

<210> SEQ ID NO 657
<211> LENGTH: 17
<212> TYPE: DNA
<213> ORGANISM: Homo Sapiens

<400> SEQUENCE: 657
gggggaaggt atggagt                                                    17

<210> SEQ ID NO 658
<211> LENGTH: 17
<212> TYPE: DNA
<213> ORGANISM: Homo Sapiens

<400> SEQUENCE: 658
catggcctcg tgggttt                                                    17

<210> SEQ ID NO 659
<211> LENGTH: 17
<212> TYPE: DNA
<213> ORGANISM: Homo Sapiens

<400> SEQUENCE: 659
catggccttg tgggttt                                                    17
```

-continued

<210> SEQ ID NO 660
<211> LENGTH: 17
<212> TYPE: DNA
<213> ORGANISM: Homo Sapiens

<400> SEQUENCE: 660
gggkagggag accagct                                                    17

<210> SEQ ID NO 661
<211> LENGTH: 17
<212> TYPE: DNA
<213> ORGANISM: Homo Sapiens

<400> SEQUENCE: 661
gggkaggggg accagct                                                    17

<210> SEQ ID NO 662
<211> LENGTH: 17
<212> TYPE: DNA
<213> ORGANISM: Homo Sapiens

<400> SEQUENCE: 662
gcagtgtcag tgtgggt                                                    17

<210> SEQ ID NO 663
<211> LENGTH: 17
<212> TYPE: DNA
<213> ORGANISM: Homo Sapiens

<400> SEQUENCE: 663
gcagtgtctg tgtgggt                                                    17

<210> SEQ ID NO 664
<211> LENGTH: 17
<212> TYPE: DNA
<213> ORGANISM: Homo Sapiens

<400> SEQUENCE: 664
acaccagcac tttgatc                                                    17

<210> SEQ ID NO 665
<211> LENGTH: 17
<212> TYPE: DNA
<213> ORGANISM: Homo Sapiens

<400> SEQUENCE: 665
acaccagcgc tttgatc                                                    17

<210> SEQ ID NO 666
<211> LENGTH: 17
<212> TYPE: DNA
<213> ORGANISM: Homo Sapiens

<400> SEQUENCE: 666
ccttctgcaa ccacacc                                                    17

<210> SEQ ID NO 667
<211> LENGTH: 17
<212> TYPE: DNA
<213> ORGANISM: Homo Sapiens

<400> SEQUENCE: 667
ccttctgcga ccacacc                                                    17

```
<210> SEQ ID NO 668
<211> LENGTH: 17
<212> TYPE: DNA
<213> ORGANISM: Homo Sapiens

<400> SEQUENCE: 668
aaattcgcag gagccga                                               17

<210> SEQ ID NO 669
<211> LENGTH: 17
<212> TYPE: DNA
<213> ORGANISM: Homo Sapiens

<400> SEQUENCE: 669
aaattcgcgg gagccga                                               17

<210> SEQ ID NO 670
<211> LENGTH: 17
<212> TYPE: DNA
<213> ORGANISM: Homo Sapiens

<400> SEQUENCE: 670
aggtctagac gctcacc                                               17

<210> SEQ ID NO 671
<211> LENGTH: 17
<212> TYPE: DNA
<213> ORGANISM: Homo Sapiens

<400> SEQUENCE: 671
aggtctaggc gctcacc                                               17

<210> SEQ ID NO 672
<211> LENGTH: 17
<212> TYPE: DNA
<213> ORGANISM: Homo Sapiens

<400> SEQUENCE: 672
ggaggaacac ttcaaac                                               17

<210> SEQ ID NO 673
<211> LENGTH: 17
<212> TYPE: DNA
<213> ORGANISM: Homo Sapiens

<400> SEQUENCE: 673
ggaggaacgc ttcaaac                                               17

<210> SEQ ID NO 674
<211> LENGTH: 17
<212> TYPE: DNA
<213> ORGANISM: Homo Sapiens

<400> SEQUENCE: 674
tttgtgctat accttga                                               17

<210> SEQ ID NO 675
<211> LENGTH: 17
<212> TYPE: DNA
<213> ORGANISM: Homo Sapiens

<400> SEQUENCE: 675
tttgtgctgt accttga                                               17
```

<210> SEQ ID NO 676
<211> LENGTH: 17
<212> TYPE: DNA
<213> ORGANISM: Homo Sapiens

<400> SEQUENCE: 676
atgatgcaca caccctg                                                17

<210> SEQ ID NO 677
<211> LENGTH: 17
<212> TYPE: DNA
<213> ORGANISM: Homo Sapiens

<400> SEQUENCE: 677
atgatgcata caccctg                                                17

<210> SEQ ID NO 678
<211> LENGTH: 17
<212> TYPE: DNA
<213> ORGANISM: Homo Sapiens

<400> SEQUENCE: 678
tattgctccg cctcctc                                                17

<210> SEQ ID NO 679
<211> LENGTH: 17
<212> TYPE: DNA
<213> ORGANISM: Homo Sapiens

<400> SEQUENCE: 679
tattgctctg cctcctc                                                17

<210> SEQ ID NO 680
<211> LENGTH: 17
<212> TYPE: DNA
<213> ORGANISM: Homo Sapiens

<400> SEQUENCE: 680
ctcagagact gtgtgcc                                                17

<210> SEQ ID NO 681
<211> LENGTH: 17
<212> TYPE: DNA
<213> ORGANISM: Homo Sapiens

<400> SEQUENCE: 681
ctcagagagt gtgtgcc                                                17

<210> SEQ ID NO 682
<211> LENGTH: 17
<212> TYPE: DNA
<213> ORGANISM: Homo Sapiens

<400> SEQUENCE: 682
atcttctgcg tcactca                                                17

<210> SEQ ID NO 683
<211> LENGTH: 17
<212> TYPE: DNA
<213> ORGANISM: Homo Sapiens

<400> SEQUENCE: 683
atcttctgtg tcactca 17

<210> SEQ ID NO 684
<211> LENGTH: 17
<212> TYPE: DNA
<213> ORGANISM: Homo Sapiens

<400> SEQUENCE: 684
cagcatctag taaccac 17

<210> SEQ ID NO 685
<211> LENGTH: 17
<212> TYPE: DNA
<213> ORGANISM: Homo Sapiens

<400> SEQUENCE: 685
cagcatctgg taaccac 17

<210> SEQ ID NO 686
<211> LENGTH: 17
<212> TYPE: DNA
<213> ORGANISM: Homo Sapiens

<400> SEQUENCE: 686
attagtgcca aatacat 17

<210> SEQ ID NO 687
<211> LENGTH: 17
<212> TYPE: DNA
<213> ORGANISM: Homo Sapiens

<400> SEQUENCE: 687
attagtgcta aatacat 17

<210> SEQ ID NO 688
<211> LENGTH: 17
<212> TYPE: DNA
<213> ORGANISM: Homo Sapiens

<400> SEQUENCE: 688
tgctccacag cagccgt 17

<210> SEQ ID NO 689
<211> LENGTH: 17
<212> TYPE: DNA
<213> ORGANISM: Homo Sapiens

<400> SEQUENCE: 689
tgctccactg cagccgt 17

<210> SEQ ID NO 690
<211> LENGTH: 17
<212> TYPE: DNA
<213> ORGANISM: Homo Sapiens

<400> SEQUENCE: 690 tagggagaa tctgttt 17

<210> SEQ ID NO 691
<211> LENGTH: 17
<212> TYPE: DNA

-continued

```
<213> ORGANISM: Homo Sapiens

<400> SEQUENCE: 691
taggggagca tctgttt                                                    17
```

METHODS AND PRODUCTS RELATED TO GENOTYPING AND DNA ANALYSIS

RELATED APPLICATIONS

This application claims benefit of U.S. Provisional Application No. 60/101,757, filed Sep. 25, 1998, the entire contents of which is hereby incorporated by reference.

GOVERNMENT SUPPORT

The present invention was supported in part by a grant from the United States National Institutes of Health under contract/grant number 5-R01-HG00299-18; the National Cancer Institute of Canada under contract/grant #009645;007477; National Research Foundation DHHS, NIH, NCI, 5 F32 CA73118-03 and NIH Predoctoring Grant T32 GM07287. The U.S. Government may retain certain rights in the invention.

FIELD OF THE INVENTION

The present invention relates to methods and products associated with genotyping. In particular, the invention relates to methods of detecting single nucleotide polymorphisms and reduced complexity genomes for use in genotyping methods as well as to various methods of genotyping, fingerprinting, and genomic analysis. The invention also relates to products and kits, such as panels of single nucleotide polymorphism allele specific oligonucleotides, reduced complexity genomes, and databases for use in the methods of the invention.

BACKGROUND OF THE INVENTION

Genomic DNA varies significantly from individual to individual, except in identical siblings. Many human diseases arise from genomic variations. The genetic diversity amongst humans and other life forms explains the heritable variations observed in disease susceptibility. Diseases arising from such genetic variations include Huntington's disease, cystic fibrosis, Duchenne muscular dystrophy, and certain forms of breast cancer. Each of these diseases is associated with a single gene mutation. Diseases such as multiple sclerosis, diabetes, Parkinson's, Alzheimer's disease, and hypertension are much more complex. These diseases may be due to polygenic (multiple gene influences) or multifactorial (multiple gene and environmental influences) causes. Many of the variations in the genome do not result in a disease trait. However, as described above, a single mutation can result in a disease trait. The ability to scan the human genome to identify the location of genes which underlie or are associated with the pathology of such diseases is an enormously powerful tool in medicine and human biology.

Several types of sequence variations, including insertions and deletions, differences in the number of repeated sequences, and single base pair differences result in genomic diversity. Single base pair differences, referred to as single nucleotide polymorphisms (SNPs) are the most frequent type of variation in the human genome (occurring at approximately 1 in $10^3$ bases). A SNP is a genomic position at which at least two or more alternative nucleotide alleles occur at a relatively high frequency (greater than 1%) in a population. SNPs are well-suited for studying sequence variation because they are relatively stable (i.e., exhibit low mutation rates) and because single nucleotide variations can be responsible for inherited traits.

Polymorphisms identified using microsatellite-based analysis, for example, have been used for a variety of purposes. Use of genetic linkage strategies to identify the locations of single Mendelian factors has been successful in many cases (Benomar et al. (1995), *Nat. Genet.*, 10:84–8; Blanton et al. (1991), *Genomics*, 11:857–69). Identification of chromosomal locations of tumor suppressor genes has generally been accomplished by studying loss of heterozygosity in human tumors (Cavenee et al. (1983), *Nature*, 305:779–784; Collins et al. (1996), *Proc. Natl. Acad Sci. USA*, 93:14771–14775; Koufos et al. (1984), *Nature*, 309:170–172; and Legius et al. (1993), *Nat. Genet.*, 3:122–126). Additionally, use of genetic markers to infer the chromosomal locations of genes contributing to complex traits, such as type I diabetes (Davis et al. (1994), *Nature*, 371:130–136; Todd et al. (1995), *Proc. Natl. Acad. Sci. USA*, 92:8560–8565), has become a focus of research in human genetics.

Although substantial progress has been made in identifying the genetic basis of many human diseases, current methodologies used to develop this information are limited by prohibitive costs and the extensive amount of work required to obtain genotype information from large sample populations. These limitations make identification of complex gene mutations contributing to disorders such as diabetes extremely difficult. Techniques for scanning the human genome to identify the locations of genes involved in disease processes began in the early 1980s with the use of restriction fragment length polymorphism (RFLP) analysis (Botstein et al. (1980), *Am. J. Hum. Genet.*, 32:314–31; Nakamura et al. (1987), *Science*, 235:1616–22). RFLP analysis involves southern blotting and other techniques. Southern blotting is both expensive and time-consuming when performed on large numbers of samples, such as those required to identify a complex genotype associated with a particular phenotype. Some of these problems were avoided with the development of polymerase chain reaction (PCR) based microsatellite marker analysis. Microsatellite markers are simple sequence length polymorphisms (SSLPs) consisting of di-, tri-, and tetra-nucleotide repeats.

Other types of genomic analysis are based on use of markers which hybridize with hypervariable regions of DNA having multiallelic variation and high heterozygosity. The variable regions which are useful for fingerprinting genomic DNA are tandem repeats of a short sequence referred to as a mini satellite. Polymorphism is due to allelic differences in the number of repeats, which can arise as a result of mitotic or meiotic unequal exchanges or by DNA slippage during replication.

The most commonly used method for genotyping involves Weber markers, which are abundant interspersed repetitive DNA sequences, generally of the form $(dC-dA)_n$ $(dG-dT)_n$. Weber markers exhibit length polymorphisms and are therefore useful for identifying individuals in paternity and forensic testing, as well as for mapping genes involved in genetic diseases. In the Weber method of genotyping, generally 400 Weber or microsatellite markers are used to scan each genome using PCR. Using these methods, if 5,000 individual genomes are scanned, 2 million PCR reactions are performed (5,000 genomes×400 markers). The number of PCR reactions may be reduced by multiplexing, in which, for instance, four different sets of primer are reacted simultaneously in a single PCR, thus reducing the total number of PCRs for the example provided to 500,000. The 500,000 PCR mixtures are separated by polyacrylamide gel electrophoresis (PAGE). If the samples are run on a 96-lane gel, 5,200 gels must be run to analyze all 500,000 PCR reaction mixtures. PCR products can be identified by their position on the gels, and the differences in length of the products can be determined by analyzing the gels. One problem with this type of analysis is that "stuttering" tends to occur, causing a smeared result and making the data difficult to interpret and score.

More recent advances in genotyping are based on automated technologies utilizing DNA chips, such as the Affymetrix HuSNP Chip™ analysis system. The HuSNP Chip™ is a disposable array of DNA molecules on a chip (400,000 per half inch square slide). The single stranded DNA molecules bound to the slide are present in an ordered array of molecules having known sequences, some of which are complementary to one allele of a SNP-containing portion of a genome. If the same 5,000 individual genome study described above is performed using the Affymetrix HuSNP Chip™ analysis system, approximately 5,000 gene chips having 1,000 or more SNPs per chip would be required. Prior to the chip scan, the genomic DNA samples would be amplified by PCR in a similar manner to conventional microsatellite genotyping. The gene chip method is also expensive and time-intensive.

SUMMARY OF THE INVENTION

The present invention relates to methods and products for identifying points of genetic diversity in genomes of a broad spectrum of species. In particular, the invention relates to a high throughput method of genotyping of SNPs in a genome (e.g. a human genome) using reduced complexity genomes (RCGs) and, in some exemplary embodiments, using SNP allele specific oligonucleotides (SNP-ASO) and specific hybridization reactions performed, for example, on a surface. The method of genotyping, in some aspects of the invention, is accomplished by scanning a RCG for the presence or absence of a SNP allele. Using this method, tens of thousands of genomes from one species may be simultaneously assayed for the presence or absence of each allele of a SNP. The methods can be automated, and the results can be recorded using a microarray scanner or other detection/recordation devices.

The invention encompasses several improvements over prior art methods. For instance, a genome-wide scan of thousands of individuals can be carried out at a fraction of the cost and time required by many prior art genotyping methods.

The invention, in one aspect, is a method for detecting the presence of a SNP allele in a genomic sample. The method, in one aspect, includes preparing a RCG from a genomic sample and analyzing the RCG for the presence of the SNP allele. In some aspects, the analysis is performed using a hybridization reaction involving a SNP allele specific oligonucleotide (SNP-ASO) which is complementary to a given allele of the SNP and the RCG. If the allele of the SNP is present in the genomic sample, then the SNP-ASO hybridizes with the RCG.

In some aspects, the method is a method for determining a genotype of a genome, whereby the genotype is identified by the presence or absence of alleles of the SNP in the RCG. In other aspects, the method is a method for characterizing a tumor, wherein the RCG is isolated from a genome obtained from a tumor of a subject and wherein the tumor is characterized by the presence or absence of an allele of the SNP in the RCG.

In other aspects, the method is a method for determining allelic frequency for a SNP, and further comprises determining the number of arbitrarily selected genomes from a population which include each allele of the SNP in order to determine the allelic frequency of the SNP in the population.

In some embodiments, the hybridization reaction is performed on a surface and the RCG or the SNP-ASO is immobilized on the surface. In yet other embodiments, the SNP-ASO is hybridized with a plurality of RCGs in individual reactions.

In other aspects, the method includes performing a hybridization reaction involving a RCG and a surface having a SNP-ASO immobilized thereon, repeating the hybridization with a plurality of RCGs from the plurality of genomes, and determining the genotype based on whether the SNP-ASO hybridizes with at least some of the RCGs.

The RCG may be a PCR-derived RCG or a native RCG. In some embodiments, the RCG is prepared by performing degenerate oligonucleotide priming-PCR (DOP-PCR) using a degenerate oligonucleotide primer having a tag-$(N)_x$-TARGET nucleotide sequence, wherein the TARGET nucleotide sequence includes at least 7 TARGET nucleotides and wherein x is an integer from 0 to 9, and wherein N is any nucleotide. In various embodiments, the TARGET nucleotide sequence includes 8, 9, 10, 11, or 12 nucleotide residues. In other embodiments, x is an integer from 3 to 9 (e.g. 6, 7, 8, or 9). Preferably, the method of genotyping is performed to determine genotypes more than one locus. In other embodiments, the RCG is prepared by performing DOP-PCR using a degenerate oligonucleotide primer having a tag-$(N)_x$-TARGET nucleotide sequence, wherein the TARGET nucleotide sequence includes fewer than 7 TARGET nucleotide residues and wherein x is an integer from 0 to 9, and wherein N is any nucleotide residue.

The methods can be performed on a support. Preferably, the support is a solid support such as a glass slide, a membrane such as a nitrocellulose membrane, etc.

In yet other embodiments, the RCG is prepared by interspersed repeat sequence-PCR (IRS-PCR), arbitrarily primed-PCR (AP-PCR), adapter-PCR, or multiple primed DOP-PCR.

In a preferred embodiment, the methods are useful for determining a genotype associated with or linked to a specific phenotype, and the distinct isolated genomes or RCGs are associated with a common phenotype.

The SNP-ASO used according to the methods of the invention are polynucleotides including one allele of two possible nucleotides at the polymorphic site. In one embodiment, the SNP-ASO is composed of from about 10 to 50 nucleotides. In a preferred embodiment, the SNP-ASO is composed of from about 10 to 25 nucleotides.

According to one embodiment, the SNP-ASO is labeled. The methods can, optionally, also include addition of an excess of non-labeled SNP-ASO in which the polymorphic nucleotide residue corresponds to a different allele of the SNP and which is added during the hybridization step. Additionally, a parallel reaction may be performed wherein the labeling of the two SNP-ASOs is reversed. The label on the SNP-ASO in one embodiment is a radioactive isotope. In this embodiment, the labeled hybridized products on the surface may be exposed to an X-ray film to produce a signal on the film which corresponds to the radioactively labeled hybridization products. In another embodiment, the SNP-ASO is labeled with a fluorescent molecule. In this embodiment, the labeled hybridized products on the surface may be exposed to an automated fluorescence reader to generate an output signal which corresponds to the fluorescently labeled hybridization products.

According to one embodiment, the RCG is labeled. The label on the RCG in one embodiment is a radioactive isotope. In this embodiment, the labeled hybridized products on the surface may be exposed to an X-ray film to produce a signal on the film which corresponds to the radioactively labeled hybridization products. In another embodiment, the RCG is labeled with a fluorescent molecule. In this embodiment, the labeled hybridized products on the surface may be exposed to an automated fluorescence reader to generate an output signal which corresponds to the fluorescently labeled hybridization products.

In one embodiment, a plurality of different SNP-ASOs are attached to the surface. In another embodiment, the plurality includes at least 500 different SNP-ASOs. In yet another embodiment, the plurality includes at least 1000.

In another embodiment, a plurality of SNP-ASOs are labeled with fluorescent molecules, each SNP-ASO being labeled with a spectrally distinct fluorescent molecule. In various embodiments, the number of spectrally distinct fluorescent molecules is two, three, four, five, six, seven, or eight.

In yet another embodiment, the plurality of RCGs are labeled with fluorescent molecules, each RCG being labeled with a spectrally distinct fluorescent molecule. All of the RCGs having a spectrally distinct fluorescent molecule can be hybridized with a single support. In various embodiments the number of spectrally distinct fluorescent molecules is two, three, four, five, six, seven, or eight.

According to other aspects, the invention encompasses methods for characterizing a tumor by assessing the loss of heterozygosity, determining allelic frequency for a SNP, generating a genomic pattern for an individual genome, and generating a genomic classification code for a genome.

In one aspect, the method for characterizing a tumor includes isolating genomic DNA from tumor samples obtained from a plurality of subjects, preparing a plurality of RCGs from the genomic DNA, performing a hybridization reaction involving a SNP-ASO and the plurality of RCGs (e.g. immobilized on a surface), and identifying the presence of a SNP allele in the genomic DNA based on whether the SNP-ASO hybridizes with at least some of the RCGs in order to characterize the tumor. One or more of the RCGs or one or more of the SNP-ASOs can be immobilized on a surface.

In another aspect, the invention is a method generating a genomic pattern for an individual genome. The method, in one aspect, includes preparing a plurality of RCGs, analyzing the RCGs for the presence of one or more SNP alleles, and identifying a genomic pattern of SNPs for each RCG by determining the presence or absence therein of SNP alleles. In some embodiments, the analysis involves performing a hybridization reaction involving a panel of SNP-ASOs (e.g. ones which are each complementary to one allele of a SNP), and the plurality of RCGs. The genomic pattern can be identified by determining the presence or absence of a SNP allele for each RCG by detecting whether the SNP-ASOs hybridize with the RCGs. In one embodiment, a plurality of SNP-ASOs are hybridized with the support, and each SNP-ASO of the panel is hybridized with a different support than the other SNP-ASO.

In some embodiments, the genomic pattern is a genomic classification code which is generated from the pattern of SNP alleles for each RCG. In other embodiments, the genomic classification code is also generated from the allelic frequency of the SNPs. In yet other embodiments, the genomic pattern is a visual pattern. The genomic pattern may be in physical or electronic form.

In another aspect, the invention includes is a method for generating a genomic pattern for an individual genome. The method includes identifying a genomic pattern of SNP alleles for each RCG by determining the presence or absence therein of selected SNP alleles.

A method for generating a genomic classification code for a genome is provided in another aspect of the invention. The method includes preparing a RCG, analyzing the RCG for the presence of one or more SNP alleles (e.g. ones of known allelic frequency), identifying a genomic pattern of SNP alleles for the RCG by determining the presence or absence therein of SNP alleles, and generating a genomic classification code for the RCG based on the presence or absence (and, optionally, the allelic frequency) of the SNP alleles. In some embodiments, the analysis involves performing a hybridization reaction involving the RCG and a panel of SNP-ASOs (e.g. corresponding to SNP alleles of known allelic frequency), each of which is complementary to one allele of a SNP. The genomic pattern is identified based on whether each SNP-ASO hybridizes with the RCG.

The method for determining allelic frequency for a SNP, in another aspect, includes preparing a plurality of RCGs from distinct isolated genomes, performing a hybridization reaction involving one RCG and a surface having a SNP-ASO immobilized thereon, repeating the hybridization with each of the plurality of RCGs, and determining the number of RCGs which include each allele of the SNP in order to determine the allelic frequency of the SNP. In other embodiments the RCGs are immobilized on the surface.

In another aspect, the method for generating a genomic pattern for an individual genome includes preparing a plurality of RCGs, performing a hybridization reaction involving a RCG and a surface having a SNP-ASO immobilized thereon, repeating the hybridization step with each of the plurality of RCGs, and identifying a genomic pattern of SNPs for each RCG by determining the presence therein of SNPs based on whether each SNP-ASO hybridizes with each RCG.

The method for generating a genomic classification code for a genome, in another aspect, includes preparing a RCG, performing a hybridization reaction involving the RCG and a panel of SNP-ASOs (e.g. immobilized on a surface), identifying a genomic pattern of SNPs for the RCG by determining the presence therein of SNPs based on whether each SNP-ASO hybridizes with the RCG, and generating a genomic classification code for the RCG based on the identities of the SNPs which hybridize with the RCG, the identities of the SNPs which do not hybridize with the RCG, and, optionally, also based on the allelic frequency of the SNPs.

In one embodiment, each SNP-ASO of the panel is immobilized on a separate surface. In another embodiment, more than one SNP-ASO of the panel is being immobilized on the same surface, each SNP-ASO being immobilized on a distinct area of the surface.

In an embodiment, the genomic classification code is encoded as one or more computer-readable signals on a computer-readable medium.

In other aspects of the invention, compositions are provided. According to one aspect, the composition is a plurality of RCGs immobilized on a surface, wherein the RCGs are prepared by a method including the step of performing DOP-PCR using a DOP primer having a tag-$(N)_x$-TARGET nucleotide sequence, wherein the TARGET nucleotide sequence includes at least 7 nucleotide residues, wherein x is an integer from 0 to 9, and wherein N is any nucleotide residue. In various embodiments, the TARGET nucleotide sequence includes 5 8, 9, 10, 11, or 12 nucleotide residues. In other embodiments, x is an integer from 3 to 9 (e.g. 6, 7, 8 or 9).

According to another aspect, the composition is a panel of SNP-ASOs immobilized on a surface, wherein the SNPs are identified by a method including preparing a set of primers from a RCG, performing PCR using the set of primers on a plurality of isolated genomes to yield DNA products, isolating and, optionally, sequencing the DNA products, and identifying a SNP based on the sequences of the PCR products. In one embodiment, the plurality of isolated genomes includes at least four isolated genomes.

According to another aspect of the invention, a kit is provided. The kit includes a container housing a set of PCR primers for reducing the complexity of a genome, and a container housing a set of SNP-ASOs. The SNPs which correspond to the SNP-ASOs of the kit are preferably present within a RCG made using the PCR primers of the kit with a frequency of at least 50%.

In one embodiment, the set of PCR primers are primers for DOP-PCR. Preferably, the degenerate oligonucleotide primer has a tag-$(N)_x$-TARGET nucleotide sequence, wherein the TARGET nucleotide sequence includes at least 7 nucleotide residues wherein x is an integer from 0 to 9, and wherein N is any nucleotide residue. In various embodiments, the TARGET nucleotide sequence includes 8, 9, 10, 11, or 12 nucleotide residues. In other embodiments, x is an integer from 3 to 9 (e.g., 6, 7, 8 or 9).

In yet other embodiments, the RCG is prepared by IRS-PCR, AP-PCR, or adapter-PCR.

The SNP-ASOs of the invention are polynucleotides including one of the alternative nucleotides at a polymorphic nucleotide residue of a SNP. In one embodiment, the SNP-ASO is composed of from about 10 to 50 nucleotide residues. In a preferred embodiment the SNP-ASO is composed of from about 10 to 25 nucleotide residues. In another embodiment, the SNP-ASOs are labeled with a fluorescent molecule.

According to yet another aspect of the invention, a composition is provided. The composition includes a plurality of RCGs immobilized on a surface, wherein the RCGs are composed of a plurality of DNA fragments, each DNA fragment including a tag $(N)_x$-TARGET nucleotide, wherein the TARGET nucleotide sequence is identical in all of the DNA fragments of each RCG, wherein the TARGET nucleotidesequence includes at least 7 nucleotide residues, wherein x is an integer from 0 to 9, and wherein N is any nucleotide residue. In various embodiments, the TARGET nucleotide sequence includes 8, 9, 10, 11, or 12 nucleotide residues. In other embodiments, x is an integer from 3 to 9 (e.g. 6, 7, 8, or 9).

In one aspect, the invention is a method for identifying a SNP. The method includes preparing a set of primers from a RCG, wherein the RCG is composed of a first set of PCR products, PCR-amplifying a plurality of isolated genomes using the set of primers to yield a second set of PCR products, isolating, and optionally, sequencing the PCR products, and identifying a SNP based on the sequences of one or both sets of PCR products. In one embodiment, the plurality of isolated genomes is a pool of genomes. Preferably, the isolated genomes are RCGs. RCGs can be prepared in a variety of ways, but it is preferred, in some aspects, that the RCG is prepared by DOP-PCR.

In one embodiment, the method of preparing the set of primers is performed by at least: preparing a RCG, separating the first set of PCR products into individual PCR products, determining the nucleotide sequence of each end of at least one of the PCR products, and generating primers for use in the subsequent PCR step based on the sequence of the ends of the PCR product(s).

The set of PCR products may be separated by any means known in the art for separating polynucleotides. In a preferred embodiment, the set of PCR products is separated by gel electrophoresis. Preferably, one or more libraries are prepared from segments of the gel containing several PCR products and clones are isolated from the library, each clone including a PCR product from the library. In other embodiments, the set of PCR products is separated by high pressure liquid chromatography or column chromatography.

The RCG used to generate primers or PCR products for identifying SNPs can be prepared by PCR methods. Preferably, the RCG is prepared by performing DOP-PCR using a degenerate oligonucleotide primer having a tag-$(N)_x$-TARGET nucleotide sequence, wherein the TARGET nucleotide sequence includes at least 7 TARGET nucleotide residues wherein x is an integer from 0 to 9, and wherein N is any nucleotide residue. In various embodiments, the TARGET nucleotide sequence includes 8, 9, 10, 11, or 12 nucleotide residues. In other embodiments, x is an integer from 3–9 (e.g. 6, 7, 8, or 9). In other embodiments, the RCG is prepared by performing DOP-PCR using a degenerate oligonucleotide primer having a tag-$(N)_x$-TARGET nucleotide sequence, wherein the TARGET nucleotide sequence includes fewer than 7 TARGET nucleotide residues, wherein x is an integer from 0 to 9, and wherein N is any nucleotide residue.

In yet other embodiments, the RCG is prepared by IRS-PCR, AP-PCR, or adapter-PCR.

In a preferred embodiment of the invention, the set of primers is composed of a plurality of polynucleotides, each polynucleotide including a tag $(N)_x$-TARGET nucleotide sequence, wherein TARGET is the same sequence in each polynucleotide in the set of primers. The sequence of $(N)_x$ is different in each primer within a set of primers. In some embodiments, the set of primers includes at least $4^3$, $4^4$, $4^5$, $4^6$, $4^7$, $4^8$, or $4^9$ different primers in the set.

In another aspect, the invention is a method for generating a RCG using DOP-PCR. The method includes the step of performing degenerate DOP-PCR using a degenerate oligonucleotide primer having an $(N)_x$-TARGET nucleotide sequence, wherein the TARGET nucleotide sequence includes at least 7 TARGET nucleotide residues and wherein x is an integer from 0 to 9, and wherein N is any nucleotide residue. In various embodiments the TARGET nucleotide sequence includes 8, 9, 10, 11, or 12 nucleotide residues. In other embodiments, x is an integer from 3 to 9 (e.g. 6, 7, 8, or 9).

According to one embodiment, the tag includes 6 nucleotide residues. Preferably the RCG is used in a genotyping procedure. In other embodiments, the RCG is analyzed to detect a polymorphism. The analysis step may be performed using mass spectroscopy.

In another aspect the invention is a method for assessing whether a subject is at risk for developing a disease. The method includes the steps of using the methods of the invention identify a plurality of SNPs that occur in at least, for example 10% of genomes obtained from individuals afflicted with the disease and determining whether one or more of those SNPs occurs in the subject. In the method the affected individuals are compared with the unaffected individuals. Important information can be generated from the observation that there is a difference between affected and unaffected individuals alone.

In other aspects the invention is a method for identifying a set of one or more SNPs associated with a disease or disease risk. The method includes the steps of preparing individual RCGs obtained from subjects afflicted with a disease, using the same set of primers to prepare each RCG, and comparing the SNP allele frequency identified in those RCGs with the same genetic SNP allele frequency in normal (i.e., non-afflicted) subjects to identify SNP associated with the disease. In other aspects the invention is a method for identifying a set of SNPs randomly distributed throughout the genome. The set of SNPs is used as a panel of genetic markers to perform a genome-wide scan for linkage analysis.

In an embodiment, a computer-readable medium having computer-readable signals stored thereon is provided. The signals define a data structure that one or more data components. Each data component includes a first data element defining a genomic classification code that identifies a corresponding genome. Each genomic classification code classifies the corresponding genome based one or more single nucleotide polymorphisms of the corresponding genome.

In an optional aspect of this embodiment, the genomic classification code is a unique identifier of the corresponding genome.

In an optional aspect of this embodiment, the genomic classification code is based on a pattern of the single nucleotide polymorphisms of the corresponding genome, where the pattern indicates the presence or absence of each single nucleotide polymorphism.

In another optional aspect of this embodiment, each data component also includes one or more data elements, each data element defining an attributes of the corresponding genome. Each of the embodiments of the invention can encompass various recitations made herein. It is, therefore, anticipated that each of the recitations of the invention involving any one element or combinations of elements can, optionally, be included in each aspect of the invention.

BRIEF DESCRIPTION OF THE SEQUENCES

SEQ. ID. NO. 1 is CAGNNNCTG

SEQ. ID. NO. 2 is TTTTTTTTTCAG

SEQ. ID. NO. 3 is CTT GCA GTG AGC CGA GATC

SEQ. ID. NO. 4 is CTCGAGNNNNNNAAGCGATG

Figure 1:
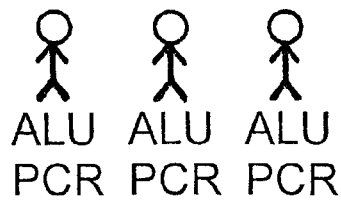
FIG. 1 is a schematic flow chart depicting a method according to the invention for identifying SNPs.
Figure 1:
Figure 1:
Figure 1:
Figure 1:
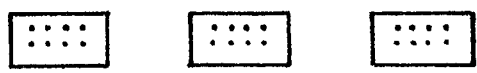
Figure 1:
Figure 1:
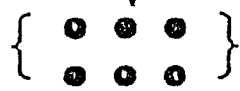

SEQ ID NO. 5–691 are nucleotide sequences containing SNPs.

DETAILED DESCRIPTION OF THE INVENTION

The invention relates in some aspects to genotyping methods involving detection of one or more single nucleotide polymorphisms (SNPs) in a reduced complexity genome (RCG) prepared from the genome of a subject. The invention includes methods of identifying SNPs associated with a disease or with pre-disposition to a disease. The invention further includes methods of screening RCGs prepared from one or more subjects in a population. Such screening can be used, for example, to determine whether the subject is afflicted with, or is likely to become afflicted with, a disorder, to determine allelic frequencies in the population, or to determine degrees of interrelation among subjects in the population. Additional aspects and details of the compositions, kits, and methods of the invention are described in the following sections.

The invention involves several discoveries which have led to new advances in the field of genotyping. The invention is based on the development of high throughput methods for analyzing genomic diversity. The methods combine use of SNPs, methods for reducing the complexity of genomes, and high throughput screening methods. As discussed in the background of the invention, many prior art methods for genotyping are based on use of hypervariable markers such as Weber markers, which predominantly detect differences in numbers of repeats. Use of a high throughput SNP analysis method is advantageous in view of the Weber marker system for several reasons. For instance, the results of a Weber analysis system are displayed in the form of a gel, which is difficult to read and must be scored by a professional. The high throughput SNP analysis method of the invention provides a binary result which indicates the presence or absence of the SNP in the sample genome. Additionally, the method of the invention requires significantly less work and is considerably less expensive to perform. As described in the background of the invention, the Weber system requires the performance of 500,000 PCR reactions and use of 5,200 gels to analyze 5,000 genomes. The same study performed using the methods of the invention could be performed without using gels. Additionally, SNPs are not species-specific and therefore the methods of the invention can be performed on diverse species and are not limited to humans.

It is more tedious to perform inter-species analysis using Weber markers than using the methods of the invention.

Some prior art methods do use SNPs for genotyping but the high throughput method of the invention has advantages over these methods as well. Affymetrix utilizes a HuSNP Chip™ system having an ordered array of SNPs immobilized on a surface for analyzing nucleic acids. This system is, however, prohibitively expensive for performing large studies such as the 5,000 genome study described above.

The invention is useful for identifying polymorphisms within a genome. Another use for the invention involves identification of polymorphisms associated with a plurality of distinct genomes. The distinct genomes may be isolated from populations which are related by some phenotypic characteristic, familial origin, physical proximity, race, class, etc. In other cases, the genomes are selected at random from populations such that they have no relation to one another other than being selected from the same population. In one preferred embodiment, the method is performed to determine the genotype (e.g. SNP content) of subjects having a specific phenotypic characteristic, such as a genetic disease or other trait.

Other uses for the methods of the invention involve identification or characterization of a subject, such as in paternity and maternity testing, immigration and inheritance disputes, breeding tests in animals, zygosity testing in twins, tests for inbreeding in humans and animals, evaluation of transplant suitability, such as with bone marrow transplants, identification of human and animal remains, quality control of cultured cells, and forensic testing such as forensic analysis of semen samples, blood stains, and other biological materials. The methods of the invention may also be used to characterize the genetic makeup of a tumor by testing for loss of heterozygosity or to determine the allelic frequency of a particular SNP. Additionally, the methods may be used to generate a genomic classification code for a genome by identifying the presence or absence of each of a panel of SNPs in the genome and to determine the allelic frequency of the SNPs. Each of these uses is discussed in more detail herein.

The genotyping methods of the invention are based on use of RCGs that can be reproducibly produced. These RCGs are used to identify SNPs, and can be screened individually for the presence or absence of the SNP alleles.

The invention, in some aspects, is based on the finding that the complexity of the genome can be reduced using various PCR and other genome complexity reduction methods and that RCG's made using such methods can be scanned for the presence of SNPs. One problem with using SNP-ASOs to screen a whole genome (i.e. a genome, the complexity of which has not been reduced) is that the signal to noise (S/N) ratio is high due to the high complexity of the genome and relative frequency of occurrence of a particular SNP-specific sequence within the whole genome. When an entire genome of a complex organism is used as the target for allele-specific oligonucleotide hybridization, the target sequence (e.g. about 17 nucleotide residues) to be detected represents only e.g. approximately $10^8$–$10^9$ 1 part in $10^8$ of the DNA sample (e.g. for a NP-ASO about 17 nucleotides). It has been discovered, according to the invention, that the complexity of the genome can be reduced in a reproducible manner and that the resulting RCG is useful for identifying the presence of SNPs in the whole genome and for genotyping methods. Reduction in complexity allows genotyping of multiple SNPs following performance of a single PCR reaction, reducing the number of experimental manipulations that must be performed. The RCG is a reliable representation of a specific subfraction of the whole genome, and can be analyzed as though it were a genome of considerably lower complexity.

RCGs are prepared from isolated genomes. An "isolated genome" as used herein is genomic DNA that is isolated from a subject and may include the entire genomic DNA. For instance, an isolated genome may be a RCG, or it may be an entire genomic DNA sample. Genomic DNA is a population of DNA that comprises the entire genetic component of a species excluding, where applicable, mitochondrial and chloroplast DNA. Of course, the methods of the invention can be used to analyze mitochondrial, chloroplast, etc., DNA as well. Depending on the particular species of the subject, the genomic DNA can vary in complexity. For instance, species which are relatively low on the evolutionary scale, such as bacteria, can have genomic DNA which is significantly less complex than species higher on the evolutionary scale. Bacteria such as $E.$ $coli$ have approximately $2.4 \times 10^9$ grams per mole of haploid genome, and bacterial genomes having a size of less than about 5 million base pairs (5 megabases) are known. Genomes of intermediate complexity, such as those of plants, for instance, rice, have a genome size of approximately 700–1,000 megabases. Genomes of highest complexity, such as maize or humans, have a genome size of approximately $10^9$–$10^{11}$. Humans have approximately $7.4 \times 10^{12}$ grams per mole of haploid genome.

A "subject" as used herein refers to any type of DNA-containing organism, and includes, for example, bacteria, viruses, fungi, animals, including vertebrates and invertebrates, and plants.

A "RCG" as used herein is a reproducible fraction of an isolated genome which is composed of a plurality of DNA fragments. The RCG can be composed of random or non-random segments or arbitrary or non-arbitrary segments. The term "reproducible fraction" refers to a portion of the genome which encompasses less than the entire native genome. If a reproducible fraction is produced twice or more using the same experimental conditions the fractions produced in each repetition include at least 50% of the same sequences. In some embodiments the fractions include at least 70%, 80%, 90%, 95%, 97%, or 99% of the same sequences, depending on how the fractions are produced. For instance, if a RCG is produced by PCR another RCG can be generated under identical experimental conditions having at a minimum greater than 90% of the sequences in the first RCG. Other methods for preparing a RCG such as size selection are still considered to be reproducible but often produce less than 99% of the same sequences.

A "plurality" of elements, as used throughout the application refers to 2 or more of the element. A "DNA fragment" is a polynucleotide sequence obtained from a genome at any point along the genome and encompassing any sequence of nucleotides. The DNA fragments of the invention can be generated according to any one of two types mechanisms, and thus there are two types of RCGs, PCR-generated RCGs and native RCGs.

PCR-generated RCGs are randomly primed. That is, each of the polynucleotide fragments in the PCR-generated RCG all have common sequences at or near the 5' and 3' end of the fragment (When a tag is used in the primer, all of the 5' and 3' ends are identical. When a tag is not used the 5' and 3' ends have a series of N's followed by the TARGET sequence (reading in a 5' to 3' direction). The TARGET sequence is identical in each primer, with the exception of multiple-primed DOP-PCR) but the remaining nucleotides within the fragments do not have any sequence relation to one another. Thus, each polynucleotide fragment in a RCG includes a common 5' and 3' sequence which is determined by the constant region of the primer used to generate the RCG. For instance, if the RCG is generated using DOP-PCR (described in more detail below) each polynucleotide fragment would have near the 5' or 3' end nucleotides that are determined by the "TARGET nucleotide sequence". The TARGET nucleotide sequence is a sequence which is selected arbitrarily but which is constant within a set or subset (e.g. multiple primed DOP-PCR) of primers. Thus, each polynucleotide fragment can have the same nucleotide sequence near the 5' and 3' end arising from the same TARGET nucleotide sequence. In some cases more than one primer can be used to generate the RCG. When more than one primer is used, each member of the RCG would have a 5' and 3' end in common with at least one other member of the RCG and, more preferably, each member of the RCG would have a 5' and 3' end in common with at least 5% of the other members of the RCG. For example, if a RCG is prepared using DOP-PCR with 2 different primers having different TARGET nucleotide sequences, a population containing of four sets of PCR products having common ends could be generated. One set of PCR products could be generated having the TARGET nucleotide sequence of the first primer at or near both the 5' and 3' ends and another set could be generated having the TARGET nucleotide sequence of the second primer at or near both the 5' and 3' ends. Another set of PCR products could be generated having the TARGET nucleotide sequence of the second primer at or near the 5' end and the TARGET nucleotide sequence of the first primer at or near the 3' end. A fourth set of PCR products could be generated having the TARGET nucleotide sequence of the second primer at or near the 3' end and the TARGET nucleotide sequence of the first primer at or near the 5' end. The PCR generated genomes are composed of synthetic DNA fragments.

The DNA fragments of the native RCGs have arbitrary sequences. That is, each of the polynucleotide fragments in the native RCG do not have necessarily any sequence relation to another fragment of the same RCG. These sequences are selected based on other properties, such as size or, secondary characteristics. These sequences are referred to as native RCGs because they are prepared from native nucleic acid preparations rather than being synthesized. Thus they are native-non-synthetic DNA fragments. The fragments of the native RCG may share some sequence relation to one another (e.g. if produced by restriction enzymes). In some embodiments they do not share any sequence relation to one another.

In some preferred embodiments, the RCG includes a plurality of DNA fragments ranging in size from approximately 200 to 2,000 nucleotide residues. In a preferred embodiment, a RCG includes from 95 to 0.05% of the intact native genome. The fraction of the isolated genome which is present in the RCG of the invention represents at most 90% of the isolated genome, and in preferred embodiments, contains less than 50%, 40%, 30%, 20%, 10%, 5%, or 1% of the genome. A RCG preferably includes between 0.05 and 1% of the intact native genome. In a preferred embodiment, the RCG encompasses 10% or less of an intact native genome of a complex organism.

Genomic DNA can be isolated from a tissue sample, a whole organism, or a sample of cells. Additionally, the isolated genomes of the invention are preferably substantially free of proteins that interfere with PCR or hybridization processes, and are also substantially free of proteins that damage DNA, such as nucleases. Preferably, the isolated genomes are also free of non-protein inhibitors of polymerase function (e.g. heavy metals) and non-protein inhibitors of hybridization when the PCR-generated RCGs are formed. Proteins may be removed from the isolated genomes by many methods known in the art. For instance, proteins may be removed using a protease, such as proteinase K or pronase, by using a strong detergent such as sodium dodecyl sulfate (SDS) or sodium lauryl sarcosinate (SLS) to lyse the cells from which the isolated genomes are obtained, or both. Lysed cells may be extracted with phenol and chloroform to produce an aqueous phase containing nucleic acid, including the isolated genomes, which can be precipitated with ethanol.

Several methods can be used to generate PCR-generated RCG including IRS-PCR, AP-PCR, DOP-PCR, multiple primed PCR, and adaptor-PCR. Hybridization conditions for particular PCR methods are selected in the context of the primer type and primer length to produce to yield a set of DNA fragments which is a percentage of the genome, as defined above. PCR methods have been described in many references, see e.g., U.S. Pat. Nos. 5,104,792; 5,106,727; 5,043,272; 5,487,985; 5,597,694; 5,731,171; 5,599,674; and 5,789,168. Basic PCR methods have been described in e.g., Saiki et al., Science, 230: 1350 (1985) and U.S. Pat. Nos. 4,683,195, 4,683,202 (both issued Jul. 18, 1987) and U.S. Pat. No. 4,800,159 (issued Jan. 24, 1989).

The PCR methods described herein are performed according to PCR methods well-known in the art. For instance, U.S. Pat. No. 5,333,675, issued to Mullis et al. describes an apparatus and method for performing automated PCR. In general, performance of a PCR method results in amplification of a selected region of DNA by providing two DNA primers, each of which is complementary to a portion of one strand within the selected region of DNA. The primer is hybridized to a template strand of nucleic acid in the presence of deoxyribonucleotide triphosphates (dATP, dCTP, dGTP, and dTTP) and a chain extender enzyme, such as DNA polymerase. The primers are hybridized with the separated strands, forming DNA molecules that are single stranded except for the region hybridized with the primer, where they are double stranded. The double stranded regions are extended by the action of the chain extender enzyme (e.g. DNA polymerase) to form an extended double stranded molecule between the original two primers. The double stranded DNA molecules are separated to produce single strands which can then be re-hybridized with the primers. The process is repeated for a number of cycles to generate a series of DNA strands having the same nucleotide sequence between and including the primers.

Chain extender enzymes are well known in the art and include, for example, *E. coli* DNA polymerase I, klenow fragment of *E. coli* DNA polymerase I, T4 DNA polymerase, T7 DNA polymerase, recombinant modified T7 DNA polymerase, reverse transcriptase, and other enzymes. Heat stable enzymes are particularly preferred as they are useful in automated thermal cycle equipment. Heat stable polymerases include, for example, DNA polymerases isolated from *bacillus stearothermophilus* (Bio-Rad), *thermus thermophilous* (finzyme, ATCC number 27634), thermus species (ATCC number 31674), *thermus aquaticus* strain TV 11518 (ATCC number 25105), *sulfolobus acidocaldarius*, described by Bukhrashuili et al., Biochem. Biophys. Acta., 1008:102–07 (1909), *thermus filiformus (ATCC number 43280)*, Taq DNA polymerase, commercially available from Perkin-Elmer-Cetus (Norwalk, Conn.), Promega (Madison, Wis.) and Stratagene (La Jolla, Calif.), and AmpliTaq™ DNA polymerase, a recombinant thermus equitus Taq DNA polymerase, available from Perkin-Elmer-Cetus and described in U.S. Pat. No. 4,889,818.

Preferably, the PCR-based RCG generation methods performed according to the invention are automated and performed using thermal cyclers. Many types of thermal cyclers are well-known in the art. For instance, M. J. Research (Watertown, Mass.) provides a thermal cycler having a peltier heat pump to provide precise uniform temperature control in the thermal cyclers; DeltaCycler thermal cyclers from Ericomp (San Diego, Calif.) also are peltier-based and include automatic ramping control, time/temperature extension programming and a choice of tube or microplate configurations. The RoboCycler™ by Stratagene (La Jolla, Calif.) incorporates robotics to produce rapid temperature transitions during cycling and well-to-well uniformity between samples; and a particularly preferred cycler, is the Perkin-Elmer Applied Biosystems (Foster City, Calif.) ABI Prism™ 877 Integrated Thermal cycler, which is operated through a programmable interface that automates liquid handling and thermocycling processes for fluorescent DNA sequencing and PCR reactions. The Perkin-Elmer Applied Biosystems machine is designed specifically for high-throughput genotyping projects and fully automates genotyping steps, including PCR product pooling.

Degenerate oligonucleotide primed-PCR (DOP-PCR) involves use of a single primer set, wherein each primer of the set is typically composed of 3 parts. A DOP-PCR primer as used herein can have the following structure:

5' tag-$(N)_x$-TARGET 3'

The "TARGET" nucleotide sequence includes at least 5 arbitrarily selected nucleotide residues that are the same for each primer of the set. x is an integer from 0 to 9, and N is any nucleotide residue. The value of x is preferably the same for each primer of a DOP-PCR primer sety. In other embodiments, the TARGET nucleotide sequence includes at least 6 or 7 and preferably at least 8, 9, or 10 arbitrarily-selected nucleotides. The tag is optional.

A "TARGET nucleotide" can be used herein is selected arbitrarily. A set of primers is used to generate a particular RCG. Each primer in the set includes the same TARGET nucleotide sequence as the other primers. Of course, sets of primers having different TARGET sequences can be combined.

The "tag", as used herein, is a sequence which is useful for processing the RCG but not necessary. The tag, unlike the other sequences in the primer, does not necessarily hybridize with genomic DNA during the initial round of genomic PCR amplification. In later amplification rounds, the tag hybridizes with PCR, amplified DNA. Thus, the tag does not contribute to the sequence initially recognized by the primer. Since the tag does not participate in the initial hybridization reaction with genomic DNA, but is involved in the primer extension process, the PCR products that are formed (i.e., the reproducible DNA fragments) include the tag sequence. Thus, the end products are DNA fragments that have a sequence identical to a sequence found in the genome except for the tag sequence. The tag is useful because in later rounds of PCR it allows use of a higher annealing temperature than could otherwise be used with shorter oligonucleotides. The arbitrarily selected sequence is positioned at the 3' end of the primer. This sequence, although arbitrarily selected, is the same for each primer in a set of DOP-PCR primers. From 0 to 9 nucleotide residues ("N" in the formula above) are located at the 5'-end of the TARGET sequence in the DOP-PCR primers of the invention. Each of these residues can be independently selected from naturally-occurring or artificial nucleotide residues. By way of example, each "N" residue can be an inosine or methylcytosine residue. In the formula, "x" is an integer that can be from 0 to 9, and is preferably from 3 to 9 (e.g. 3, 4, 5, 6, 7, 8, or 9). Each set of DOP-PCR primers of the invention can thus contain up to $4^x$ unique primers (i.e., 1, 4, 16, 64 . . . , 262144 primers for x=0, 1, 2, 3, . . . , 9). Finally, a base pair tag can be positioned at the 5' end of the primer. This tag can optionally include a restriction enzyme site. In general, inclusion of a tag sequence in the DOP-PCR primers of the invention is preferred, but not necessary.

The initial rounds of DOP-PCR are preferably performed at a low temperature given that the specificity of the reaction will be determined by only the 3' TARGET nucleotide sequence. A slow ramp time during these cycles ensures that the primers do not detach from the template before being extended. Subsequent rounds are carried out at a higher annealing temperature because in the subsequent rounds the 5' end of the DOP-PCR primer (the tag) is able to contribute to the primer annealing. A PCR cycle performed under low stringency hybridization conditions generally is from about 35° C. to about 55° C.

Because DOP-PCR involves a randomly chosen sequence, the resultant PCR products are generated from genome sequences arbitrarily distributed throughout the genome and will generally not be clustered within specific sites of the genome. Additionally, creation of new sets of DOP-PCR-amplified DNA fragments can be easily accomplished by changing the sequence, length, or both, of the primer. RCGs having greater or lesser complexity can be generated by selecting DOP-PCR primers having shorter or longer, respectively, TARGET and $(N)_x$ nucleotide sequences. This approach can also be used with multiple DOP-PCR primers such as in the "multiple-primed DOP-PCR" method (described below). Finally, use of arbitrarily chosen sequences of DOP-PCR is useful in many species because the arbitrarily-selected sequences are not species-specific, as with some forms of PCR which require use of a specific known sequence.

Another method for generating a PCR-generated RCG involves interspersed repeat sequence PCR (IRS-PCR). Mammalian chromosomes include both repeated and unique sequences. Some of the repeated sequences are short interspersed repeated sequences (IRS's) and others are long IRS's. One major family of short IRS's found in humans includes Alu repeat sequences. Amplification using a single Alu primer will occurs whenever two Alu elements lie in inverted orientation to each other on opposite strands. There are believed to be approximately 900,000 Alu repeats in a human haploid genome. Another type of IRS sequence is the L1 element (most common is L1Hs) which is present in $10^4$–$10^5$ copies in a human genome. Because the L1 sequence is expressed less abundantly in the genome than the Alu sequence, fewer amplification products are produced upon amplification using an L1 primer. In IRS-PCR, a primer which has homology to a repetitive sequence present on opposite strands within the genome of the species to be analyzed is used. When two repeat elements having the primer sequence are present in a head-to-head fashion within a limited distance (approximately 2000 nucleotide residues), the inter-repeat sequence can be amplified. The method has the advantage that the complexity of the resulting PCR products can be controlled by how homologous the primer chosen is with the repeat consensus (that is, the more homologous the primer is with the repeat consensus sequence, the more complex the PCR product will be).

In general, an IRS-PCR primer has a sequence wherein at least a portion of the primer is homologous with (e.g. 50%, 75%, 90%, 95% or more identical to) the consensus nucleotide sequence of an IRS of the subject.

In mammalian genomes, small interspersed repeat sequences (SINES) are present in extremely high copy number and are often configured such that a single copy sequence of between 500 nucleotide residues and 1000 nucleotide residues is situated between two repeats which are oriented in a head-to-head or tail-to-tail manner. Genomic DNA sequences having this configuration are substrates for Alu PCR in human DNA and B1 and B2 PCR in the mouse. The precise number of products which are represented in a specific Alu, B1, or B2 PCR reaction depends on the choice of primer used for the reaction. This variation in product complexity is due to the variation in sequence among the large number of representative sequences of the IRS family in each species. A detailed study of this variation was described by Britten (Britten, R. J. (1994), *Proc. Natl. Acad. Sci. USA*, 91:5992–5996). In the Britten study, the sequence variation for each nucleotide residue of the Alu consensus sequence was analyzed for 1574 human Alu sequences. The complexity of Alu PCR products generated by amplification using a given Alu PCR primer can be predicted to a significant extent based on the degree to which the nucleotide sequence of the primer matches consensus nucleotide sequences. As a general rule, Alu PCR products become progressively less complex as the primer sequence diverges from the Alu consensus. Because two hybridized primers are required at each site for which Alu PCR is to be accomplished, it is predictable that linear variation and the number of genomic sites to which a primer may bind will be reflected in the complexity of PCR products, which is roughly proportional to the square of primer binding efficiency. This prediction conforms to experimental results, permitting synthesis of Alu PCR products having a wide range of product complexity values. Therefore, when it is desirable to reduce the number of PCR products obtained using Alu PCR, the primer sequence should be designed to diverge by a predictable amount from the Alu consensus sequence.

Another method for generating a RCG involves arbitrarily primed PCR (AP-PCR). AP-PCR utilizes short oligonucleotides as PCR primers to amplify a discrete subset of portions of a high complexity genome. For AP-PCR, the primer sequence is arbitrary and is selected without knowledge of the sequence of the target nucleic acids to be amplified. The arbitrary primer is generally 50–60% G+C. The AP-PCR method is similar to the DOP-PCR method described above, except that the AP-PCR primer consists of only the arbitrarily-selected nucleotides and not the 5' flanking degenerate residues or the tag (i.e. $N_x$ residue described for the DOP-PCR primers). The genome may be primed using a single arbitrary primer or a combination of two or more arbitrary primers, each having a different, but optionally related, sequence.

AP-PCR is performed under low stringency hybridization conditions, allowing hybridization of the primer with targets with which the primer can exhibit a substantial degree of mismatching. A PCR cycle performed under low stringency hybridization conditions generally is from about 35° C. to about 55° C. Mismatches refer to non complementary nucleotide bases in the primer, relative to the template with which it is hybridized.

AP-PCR methods have been used previously in combination with gel electrophoresis to determine genotypes. AP-PCR products are generationally fractionated on a high resolution polyacrylamide gel, and the presence or absence of specific bands is used to genotype a specific locus. In general, the difference between the presence and absence of a band is a consequence of a single nucleotide DNA sequence difference in one of the primer binding sites for a given single copy sequence.

The product complexity obtained using a given primer or primer set can be determined by several methods. For instance, the product complexity can be determined using PCR amplification of a panel of human yeast artificial chromosome (YAC) DNA samples from a CEPH 1 library. These YACs each carry a human DNA segment approximately 300–400 kilobase pairs in length. Product complexity for each primer set can be inferred by comparing the number of bands produced per YAC when analyzed on agarose gel with an IRS-PCR product of known complexity. Additionally, for products of relatively low complexity, electrophoresis on polyacrylamide gels can establish the product complexity, compared to a standard. Alternatively, an effective way to estimate the complexity of the product is to carry out a reannealing reaction using resistance to S1 nuclease-catalyzed degradation to determine the rate of reannealing of internally labeled, denatured, double-stranded DNA product. Comparison with reannealing rates of standards of known complexity permits accurate estimation of product complexity. Each of these three methods may be used for IRS PCR. The second and third methods are best for AP-PCR and DOP-PCR which, unlike IRS-PCR, will not selectively amplify human DNA from a crude YAC DNA preparation.

The complexity of PCR products generated by AP-PCR can be regulated by selecting the primer sequence length, the number of primers in a primer set, or some combination of these. By choosing the appropriate combination, AP-PCR may also be used to reduce the complexity of a genome for SNP identification and genotyping, as described herein. AP-PCR markers are different from Alu PCR primers, have a different genomic distribution, and can therefore complement an IRS-PCR genome complexity-reducing method. The methods can be used in combination to produce complementary information from genome scans.

One PCR method for preparing RCGs is an adapter-linker amplification PCR method (previously described in e.g., Saunders et al., Nuc. Acids Res., 17 9027 (1990); Johnson, Genomics, 6: 243 (1990) and PCT Application WO90/00434, published Aug. 9, 1990. In this method, genomic DNA is digested using a restriction enzyme, and a set of linkers is ligated onto the ends of the resulting DNA fragments. PCR amplification of genomic DNA is accomplished using a primer which can bind with the adapter linker sequence. Two possible variations of this procedure which can be used to limit genome complexity are (a) to use a restriction enzyme which produces a set of fragments which vary in length such that only a subset (e.g. those smaller than a PCR-amplifiable length) are amplified; and (b) to digest the genomic DNA using a restriction enzyme that produces an overhang of random nucleotide sequence (e.g., AlwN1 recognizes CAGNNNCTG; SEQ ID NO: 1) and cleaves between NNN and CTG). Adapters are constructed to anneal with only a subset of the products. For example, in the case of AlwN1, adapters having a specific 3 nucleotide residue overhang (corresponding to the random 3 base pair sequence produced by the restriction enzyme digestion) would be used to yield ($4^3$) 64-fold reduction in complexity. Fragments which have an overhang sequence complementary to the adapter overhang are the only ones which are is amplified.

Another method for generating RCGs is based on the development of native RCGs. Several methods can be used to generate native RCGs, including DNA fragment size selection, isolating a fraction of DNA from a sample which has been denatured and reannealed, pH-separation, separation based on secondary structure, etc.

Size selection can be used to generate a RCG by separating polynucleotides in a genome into different fractions wherein each fraction contains polynucleotides of an approximately equal size. One or more fractions can be selected and used as the RCG. The number of fractions selected will depend on the method used to fragment the genome and to fractionate the pieces of the genome, as well as the total number of fractions. In order to increase the complexity of the RCG, more fractions are selected. One method of generating a RCG involves fragmenting a genome into arbitrarily size pieces and separating the pieces on a gel (or by HPLC or another size fractionation method). A portion of the gel is excised, and DNA fragments contained in the portion are isolated. Typically, restriction enzymes can be used to produce DNA fragments in a reproducible manner.

Separation based on secondary structure can be accomplished in a manner similar to size selection. Different fractions of a genome having secondary structure can be separated on a gel. One or more fractions are excised from the gel, and DNA fragments are isolated therefrom.

Another method for creating a native RCG involves isolating a fraction of DNA from a sample which has been denatured and reannealed. A genomic DNA sample is denatured, and denatured nucleic acid molecules are allowed to reanneal under selected conditions. Some conditions allow more of the DNA to be reannealed than other conditions. These conditions are well known to those of ordinary skill in the art. Either the reannealed or the remaining denatured fractions can be isolated. It is desirable to select the smaller of these two fractions in order to generate RCG. The reannealing conditions used in the particular reaction determine which fraction is the smaller fraction. Variations of this method can also be used to generate RCGs. For instance, once a portion of the fraction is allowed to reanneal, the double stranded DNA may be removed (e.g., using column chromatography), the remaining DNA can then be allowed to partially reanneal, and the reannealed fraction can be isolated and used. This variation is particularly useful for removing repetitive elements of the DNA, which rapidly reanneal.

The amount of isolated genome used in the method of preparing RCGs will vary, depending on the complexity of the initial isolated genome. Genomes of low complexity, such as bacterial genomes having a size of less than about 5 million base pairs (5 megabases), usually are used in an amount from approximately 10 picograms to about 250 nanograms. A more preferred range is from 30 picograms to about 7.5 nanograms, and even more preferably, about 1 nanogram. Genomes of intermediate complexity, such as plants (for instance, rice, having a genome size of approximately 700–1,000 megabases) can be used in a range of from approximately 0.5 nanograms to 250 nanograms. More preferably, the amount is between 1 nanogram and 50 nanograms. Genomes of highest complexity (such as maize or humans, having a genome size of approximately 3,000 megabases) can be used in an amount from approximately 1 nanogram to 250 nanograms (e.g. for PCR).

In addition to the DOP-PCR methods described above, PCR-generated RCGs can be prepared using DOP-PCR involving multiple primers, which is referred to herein as "multiple-primed-DOP-PCW". Multiple-primed-DOP-PCR involves the use of at least two primers which are arranged similarly to the single primers discussed above and are typically composed of 3 parts. A multiple-primed-DOP-PCR primer as used herein has the following structure:

tag-$(N)_x$-TARGET$_2$

The TARGET$_2$ nucleotide sequence includes at least 5, and preferably at least 6, TARGET nucleotide residues, x is an integer from 0–9, and N is any nucleotide residue.

The sequence chosen arbitrarily and positioned at the 3' end of the primer can be manipulated in multiple-primed-DOP-PCR to produce a different end product than for DOP-PCR because use of two or more sets of primers adds another level of diversity, thus producing a RCG or amplified genome, depending on the primers chosen. Each of the at least two sets of primers of multiple-primed-DOP-PCR has a different TARGET sequence. Similar to the single primer of DOP-PCR a set of primers is generated for each of the at least two primers and, every primer within a single set has the same TARGET sequence as the other primers of the set. This TARGET sequence is flanked at its 5' end by 0 to 9 nucleotide residues ("N"s). The set of N's will differ from primer to primer within a set of primers. A set of primers may include up to $4^x$ different primers, each primer having a unique $(N)_x$ sequence. Finally a tag can be positioned at the 5' end.

In other aspects of the invention, methods for identifying SNPs can be performed using RNA genomes rather than RCGs. RNA genomes differ from RCGs in that they are generated from RNA rather than from DNA. An RNA genome can be, for instance, a cDNA preparation made by reverse transcription of RNA obtained from cells of a subject (e.g. human ovarian carcinoma cells). Thus, an RNA genome can be composed of DNA sequences, as long as the DNA is derived from RNA. RNA can also be used directly.

The genotyping and other methods of the invention can also be performed using a RNA genotyping method. This method involves use of RNA, rather than DNA, as the source of nucleic acid for genotyping. In this embodiment, RNA is reverse transcribed (e.g. using a reverse transcriptase) to produce cDNA for use as an RNA genome. The RNA method has at least one advantage over DNA-based methods. SNPs in coding regions (cSNPs) are more likely to be directly involved in detectable phenotypes and are thus more likely to be informative with regard to how such phenotypes can be affected. Furthermore, since this method can require only a reverse transcription step, it is amenable to high-throughput analysis. In a preferred embodiment, a reverse transcriptase primer which only binds a subset of RNA species (e.g. a dT primer having a 3-base anchor, e.g. TTTTTTTTTT CAG; SEQ ID NO: 2) is used to further reduce RNA genome complexity (48-fold using the dt-3base anchor primer). In the RNA-genotyping method of the invention the RNA/cDNA sample can be attached to a surface and hybridized with a SNP-ASO.

In another aspect, the invention includes a method for identifying a SNP. Genomic fragments which include SNPs can be prepared according to the invention by preparing a set of primers from a RCG (e.g., a RCG is composed of a set of PCR products), performing PCR using the set of primers to amplify a plurality of isolated genomes to produce DNA products, and identifying SNPs included in the DNA products. The presence of a SNP in the DNA product can be identified using methods such as direct sequencing, i.e. using dideoxy chain termination or Maxam Gilbert (see e.g., Sambrook et al, "Molecular Cloning: A Laboratory Manual," Cold Spring Harbor Laboratory, 1989, New York; or Zyskind et al., Recombinant DNA Laboratory Manual, Acad. Press, 1988), denaturing gradient gel electrophoresis to identify different sequence dependent melting properties and electrophoretic migration of SNPs containing DNA fragments (see e.g., Erlich, ed., PCR Technology, Principles and applications for DNA Amplification, Freeman and Co., NY, 1992), and conformation analysis to differentiate sequences based on differences in electrophoretic migration patterns of single stranded DNA products (see e.g., Orita et al., Proc. Nat. Acad. Sci. 86, 2766–2770, 1989). In preferred embodiments, the SNPs are identified based on the sequences of the polymerase chain reaction products identified using sequencing methods.

A "single nucleotide polymorphism" or "SNP" as used herein is a single base pair (i.e., a pair of complementary nucleotide residues on opposite genomic strands) within a DNA region wherein the identities of the paired nucleotide residues vary from individual to individual. At the variable base pair in the SNP, two or more alternative base pairings occur at a relatively high frequency (greater than 1%) in a subject, (e.g. human) population.

A "polymorphic region" is a region or segment of DNA the nucleotide sequence of which varies from individual to individual. The two DNA strands which are complementary to one another except at the variable position are referred to as alleles. A polymorphism is allelic because some members of a species have one allele and other members have a variant allele and some have both. When only one variant sequence exists, a polymorphism is referred to as a diallelic polymorphism. There are three possible genotypes in a diallelic polymorphic DNA in a diploid organism. These three genotypes arise because it is possible that a diploid individual's DNA may be homozygous for one allele, homozygous for the other allele, or heterozygous (i.e. having one copy of each allele). When other mutations are present, it is possible to have triallelic or higher order polymorphisms. These multiple mutation polymorphisms produce more complicated genotypes.

SNPs are well-suited for studying sequence variation because they are relatively stable (i.e. they exhibit low mutation rates) and because it appears that SNPs can be responsible for inherited traits. These properties make SNPs particularly useful as genetic markers for identifying disease-associated genes. SNPs are also useful for such purposes as linkage studies in families, determining linkage disequilibrium in isolated populations, performing association analysis of patients and controls, and loss of heterozygosity studies in tumors.

An exemplary method for identifying SNPs is presented in the Examples below. Briefly, DOP-PCR is performed using genomic DNA obtained from an individual. The products are separated on an agarose gel. The products are separated by approximate length into approximately 8 segments having sizes of about 400–1000 base pairs, and libraries are made from each of the segments. This approach prevents domination of the library by one or two abundant products. Plasmid DNA is isolated from individual colonies containing portions of the library. Inserts are isolated and the ends of the inserts are sequenced using vector primers. A new set of primers is then synthesized based on these insert sequences to allow PCR to be performed using RCG obtained from one or more individuals or from a pool of individuals. The DNA products generated by the PCR are sequenced and inspected for the presence of two nucleotide residues at one location, an indication that a polymorphism exists at that position within one of the alleles.

A "primer" as used herein is a polynucleotide which hybridizes with a target nucleic acid with which it is complementary and which is capable of acting as an initiator of nucleic acid synthesis under conditions for primer extension. Primer extension conditions include hybridization between the primer and template, the presence of free nucleotides, a chain extender enzyme, e.g., DNA polymerase, and appropriate temperature and pH.

In preferred embodiments, a set of primers is prepared by at least the following steps: preparing a RCG, composed of a set of PCR products, separating the set of PCR products into individual PCR products, determining the sequence of each end of at least one of the PCR products, and generating the set of primers for use in the subsequent PCR step based on the sequence of the ends of the insert(s).

A "set of PCR products", as used herein, is a plurality of synthetic polynucleotide sequences, each polynucleotide sequence being different from one another except for a stretch of nucleotides in the 5' and 3' regions of the polynucleotides which are identical in each polynucleotide. These regions correspond to the primers used to generate the RCG and the sequence in these regions varies depending on what primer is used. When a DOP PCR primer is used, the sequence that varies in each primer preferably has a sequence $N_x$, wherein x is 5–12 and N is any nucleotide. A set of DNA products is different from a "set of PCR products" as used herein and refers to DNA generated by PCR using specific primers which amplify a specific locus.

Once the sequence of a primer is known, the primer may be purified from a nucleic acid preparation which includes, it or it may be prepared synthetically. For instance, nucleic acid fragments may be isolated from nucleic acid sequences in genomes, plasmids, or other vectors by site-specific cleavage, etc. Alternatively, the primers may be prepared by de novo chemical synthesis, such as by using phosphotriester or phosphodiester synethetic methods, such as those described in U.S. Pat. No. 4,356,270; Itakura et al. (1989), Ann. Rev. Biochem., 53:323–56; and Brown et al. (1979), Meth. Enzymol., 68:109. Primers may also be prepared using recombinant technology, such as that described in Sambrook, "Molecular Cloning: A Laboratory Manual," Cold Spring Harbor Laboratory, p. 390–401 (1982).

The term "nucleotide residue" refers to a single monomeric unit of a nucleic acid such as DNA or RNA. The term "base pair" refers to two nucleotide residues which are complementary to one another and are capable of hydrogen bonding with one another. Traditional base pairs are between G:C and T:A. The letters G, C, T, U and A refer to (deoxy)guanosine, (deoxy)cytidine, (deoxy)thymidine, uridine, and (deoxy)adenosine, respectively. The term "nucleic acids" as used herein refers to a class of molecules including single stranded and double stranded deoxyribonucleic acid (DNA), ribonucleic acid (RNA), and polynucleotides. Nucleic acids within the scope of the invention include naturally occurring and synthetic nucleic acids, nucleic acid analogs, modified nucleic acids, nucleic acids containing modified nucleotides, modified nucleic acid analogs, and mixtures of any of these.

SNPs identified or detected in the genotyping methods described herein can also be identified by other methods known in the art. Many methods have been described for identifying SNPs. (see e.g. WO95/12607, Bostein, et al., Am. J. Hum. Genet,. 32:314–331 (1980), etc.). In some embodiments, it is preferred that SNPs be identified using the same method that will subsequently be used for genotype analysis.

As discussed briefly above, the SNPs and RCGs of the invention are useful for a variety of purposes. For instance, SNPs and RCGs are useful for performing genotyping analysis; for identification of a subject, such as in paternity or maternity testing, in immigration and inheritance disputes, in breeding tests in animals, in zygosity testing in twins, in tests for inbreeding in humans and animals; in evaluation of transplant suitability such as with bone marrow transplants; in identification of human and animal remains; in quality control of cultured cells; in forensic testing such as forensic analysis of semen samples, blood stains, and other biological materials; in characterization of the genetic makeup of a tumor by testing for loss of heterozygosity; in determining the allelic frequency of a particular SNP; and in generating a genomic classification code for a genome by identifying the presence or absence of each of a panel of SNPs in the genome of a subject and optionally determining the allelic frequency of the SNPs.

A preferred use of the invention is in a high throughput method of genotyping. "Genotyping" is the process of identifying the presence or absence of specific genomic sequences within genomic DNA. Distinct genomes may be isolated from individuals of populations which are related by some phenotypic characteristic, by familial origin, by physical proximity, by race, by class, etc. in order to identify polymorphisms (e.g. ones associated with a plurality of distinct genomes) which are correlated with the phenotype family, location, race, class, etc. Alternatively, distinct genomes may be isolated at random from populations such that they have no relation to one another other than their origin in the population. Identification of polymorphisms in such genomes indicates the presence or absence of the polymorphisms in the population as a whole, but not necessarily correlated with a particular phenotype.

Although genotyping is often used to identify a polymorphism associated with a particular phenotypic trait, this correlation is not necessary. Genotyping only requires that a polymorphism, which may or may not reside in a coding region, is present. When genotyping is used to identify a phenotypic characteristic, it is presumed that the polymorphism affects the phenotypic trait being characterized. A phenotype may be desirable, detrimental, or, in some cases, neutral.

Polymorphisms identified according to the methods of the invention can contribute to a phenotype. Some polymorphisms occur within a protein coding sequence and thus can affect the protein structure, thereby causing or contributing to an observed phenotype. Other polymorphisms occur outside of the protein coding sequence but affect the expression of the gene. Still other polymorphisms merely occur near genes of interest and are useful as markers of that gene. A single polymorphism can cause or contribute to more than one phenotypic characteristic and, likewise, a single phenotypic characteristic may be due to more than one polymorphism. In general multiple polymorphisms occurring within a gene correlate with the same phenotype. Additionally, whether an individual is heterozygous or homozygous for a particular polymorphism can affect the presence or absence of a particular phenotypic trait.

Phenotypic correlation is performed by identifying an experimental population of subjects exhibiting a phenotypic characteristic and a control population which do not exhibit that phenotypic characteristic. Polymorphisms which occur within the experimental population of subjects sharing a phenotypic characteristic and which do not occur in the control population are said to be polymorphisms which are correlated with a phenotypic trait. Once a polymorphism has been identified as being correlated with a phenotypic trait, genomes of subjects which have potential to develop a phenotypic trait or characteristic can be screened to determine occurrence or non-occurrence of the polymorphism in the subjects' genomes in order to establish whether those subjects are likely to eventually develop the phenotypic characteristic. These types of analyses are generally carried out on subjects at risk of developing a particular disorder such as Huntington's disease or breast cancer.

A phenotypic trait encompasses any type of genetic disease, condition, or characteristic, the presence or absence of which can be positively determined in a subject. Phenotypic traits that are genetic diseases or conditions include multifactorial diseases of which a component may be genetic (e.g. owing to occurrence in the subject of a SNP), and predisposition to such diseases. These diseases include such as, but not limited to, asthma, cancer, autoimmune diseases, inflammation, blindness, ulcers, heart or cardiovascular diseases, nervous system disorders, and susceptibility to infection by pathogenic microorganisms or viruses. Autoimmune diseases include, but are not limited to, rheumatoid arthritis, multiple sclerosis, diabetes, systemic lupus, erythematosus and Grave's disease. Cancers include, but are not limited to, cancers of the bladder, brain, breast, colon, esophagus, kidney, hematopoietic system eg. leukemia, liver, lung, oral cavity, ovary, pancreas, prostate, skin, stomach, and uterus. A phenotypic characteristic includes any attribute of a subject other than a disease or disorder, the presence or absence of which can be detected. Such characteristics can, in some instances, be associated with occurrence of a SNP in a subject which exhibits the characteristic. Examples of characteristics include, but are not limited to, susceptibility to drug or other therapeutic treatments, appearance, height, color (e.g. of flowering plants), strength, speed (e.g. of race horses), hair color, etc. Many examples of phenotypic traits associated with genetic variation have been described, see e.g., U.S. Pat. No. 5,908,978 (which identifies association of disease resistance in certain species of plants associated with genetic variations) and U.S. Pat. No. 5,942,392 (which describes genetic markers associated with development of Alzheimer's disease).

Identification of associations between genetic variations (e.g. occurrence of SNPs) and phenotypic traits is useful for many purposes. For example, identification of a correlation between the presence of a SNP allele in a subject and the ultimate development by the subject of a disease is particularly useful for administering early treatments, or instituting lifestyle changes (e.g., reducing cholesterol or fatty foods in order to avoid cardiovascular disease in subjects having a greater-than-normal predisposition to such disease), or closely monitoring a patient for development of cancer or other disease. It may also be useful in prenatal screening to identify whether a fetus is afflicted with or is predisposed to develop a serious disease. Additionally, this type of information is useful for screening animals or plants bred for the purpose of enhancing or exhibiting of desired characteristics.

One method for determining a genotype associated with a plurality of genomes is screening for the presence or absence of a SNP in a plurality of RCGs. For example, such screening may be performed using a hybridization reaction including a SNP-ASO and the RCGs. Either the SNP-ASO or the RCGs can, optionally be immobilized on a surface. The genotype is determined based on whether the SNP-ASO hybridizes with at least some of the RCGs. Other methods for determining a genotype involve methods which are not based on hybridization, including, but not limited to, mass spectrometric methods. Methods for performing mass spectrometry using nucleic acid samples have been described. See e.g., U.S. Pat. No. 5,885,775. The components of the RCG can be analyzed by mass spectrometry to identify the presence or absence of a SNP allele in the RCG.

A "SNP-ASO", as used herein, is an oligonucleotide which includes one of two alternative nucleotides at a polymorphic site within its nucleotide sequence. In some embodiments, it is preferred that the oligonucleotide include only a single mismatched nucleotide residue namely the polymorphic residue, relative to an allele of a SNP. In other cases, however, the oligonucleotide may contain additional nucleotide mismatches such as neutral bases or may include nucleotide analogs. This is described in more detail below. In preferred embodiments, the SNP-ASO is composed from about 10 to 50 nucleotide residues. In more preferred embodiments, it is composed of from about 10 to 25 nucleotide residues.

Oligonucleotides may be purchased from commercial sources such as Genosys, Inc., Houston, Texas or, alternatively, may be synthesized de novo on an Applied Biosystems 381A DNA synthesizer or equivalent type of machine.

The oligonucleotides may be labeled by any method known in the art. One preferred method is end-labeling, which can be performed as described in Maniatis et al., "Molecular Cloning: A Laboratory Manual", Cold Spring Harbor Laboratories, Cold Spring Harbor, N.Y. (1982).

It is possible that in organisms having a relatively non-complex genome, only a minimal complexity reduction step is necessary, and the genomic DNA may be directly analyzed or minimally reduced. This is particularly useful for screening tissue isolates to detect the presence of a bacterium or to identify the bacteria. Additionally, it is possible that, upon development of certain technical advances (e.g., more stringent hybridization, more sensitive detection equipment), even complex genomes may not need an extensive complexity reduction step.

Figure 4:
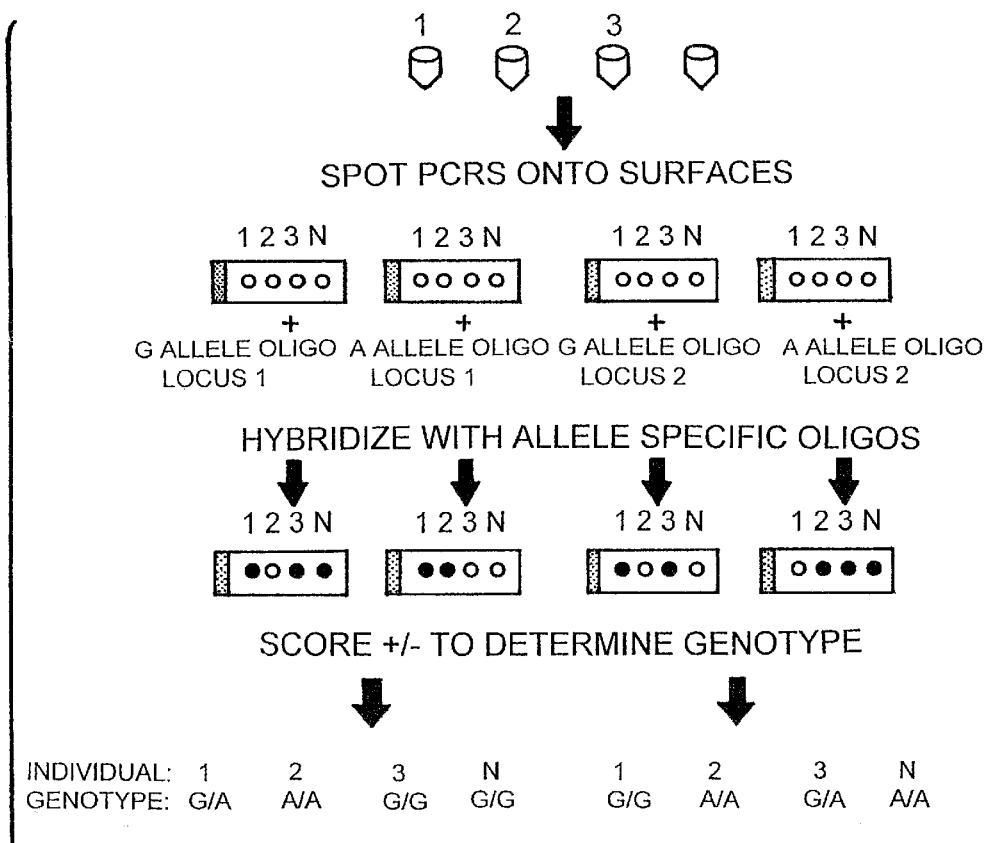
FIG. 4 is a schematic flow chart depicting a method according to the invention for detecting SNPs.

Preferably, automated genotyping is performed. In general, genomic DNA of a well-characterized set of subjects, such as the CEPH families, is processed using PCR with appropriate primers to produce RCGs. The DNA is spotted onto one or more surfaces (e.g., multiple glass slides) for genotyping. This process can be performed using a microarray spotting apparatus which can spot more than 1,000 samples within a square centimeter area, or more than 10,000 samples on a typical microscope slide. Each slide is hybridized with a fluorescently tagged allele-specific SNP oligonucleotide under TMAC conditions analogous to those described below. The genotype of each individual can be determined by detecting the presence or absence of a signal for a selected set of SNP-ASOs. A schematic of the method is shown in FIG. 4.

Once the complexity of genomic DNA obtained from an individual has been reduced, the resulting genomic DNA fragments can be attached to a solid support in order to be analyzed by hybridization. The RCG fragments may be attached to the slide by any method for attaching DNA to a surface. Methods for immobilizing nucleic acids have been described extensively, e.g., in U.S. Pat. Nos. 5,679,524; 5,610,287; 5,919,626; and 5,445,934. For instance, DNA fragments may be spotted onto poly-L-lysine-coated glass slides, and then crosslinked by UV irradiation. A second, more preferred method, which has been developed, involves including a 5' amino group on each of the DNA fragments of the RCG. The DNA fragments are spotted onto silane-coated slides in the presence of NaOH in order to covalently attach the fragments to the slide. This method is advantageous because a covalent bond is formed between the fragments and the surface. Another method for accomplishing DNA fragment immobilization is to spot the RCG fragments onto a nylon membrane. Other methods of binding DNA to surfaces are possible and are well known to those of ordinary skill in the art. For instance, attachment to amino-alkyl-coated slides can be used. More detailed methods are described in the Examples below.

The surface to which the oligonucleotide arrays are conjugated is preferably a rigid or semi-rigid support which may, optionally, have appropriate light absorbing or transmitting characteristics for use with commercially available detection equipment. Substrates which are commonly used and which have appropriate light absorbing or transmitting characteristics include, but are not limited to, glass, Si, Ge, GaAs, GaP, $SiO_2$, $SiN_4$, modified silicon, and polymers such as (poly)tetrafluoroethylene, (poly)vinylidenedifluoride, polystyrene, polycarbonate, or combinations thereof. Additionally, the surface of the support may be non-coated or coated with a variety of materials. Coatings include, but are not limited to, polymers, plastics, resins, polysaccharides, silica or silica-based materials, carbon, metals, inorganic glasses, and membranes.

In one embodiment the SNP-ASOs are hybridized under standard hybridization conditions with RCGs covalently conjugated to a surface. Briefly, SNP-ASOs are labeled at their 5' ends. A hybridization mixture containing the SNP-ASOs and, optionally, an isostabilizing agent, denaturing agent, or renaturation accelerant is brought into contact with an array of RCGs immobilized on the surface and the mixture and the surface are incubated under appropriate hybridization conditions. The SNP-ASOs which do not hybridize are removed by washing the array with a wash mixture (such as a hybridization buffer) to leave only hybridized SNP-ASOs attached to the surface. After washing, detection of the label (e.g., a fluorescent molecule) is performed. For example, an image of the surface can be captured (e.g., using a fluorescence microscope equipped with a CCD camera and automated stage capabilities, phosphoimager, etc.). The label may also, or instead, be detailed using a microarray scanner (e.g. one made by Genetic Microsystems). A microarray scanner provides image analysis which can be converted to a binary (i.e. +/−) signal for each sample using, for example, any of several available software applications (e.g., NIH image, ScanAnalyze, etc.) in a data format. The high signal/noise ratio for this analysis allows determination of data in this mode to be straightforward and easily automated. These data, once exported, can be manipulated to generate a format which can be directly analyzed by human genetics applications (such as CRI-MAP and LINKAGE via software). Additionally, the methods may utilize two or more fluorescent dyes which can be spectrally differentiated to reduce the number of samples to be analyzed. For instance, if four fluorescent dyes having spectral distinctions (e.g., ABI Prism dyes 6-FAM, HEX, NED, ROX) are used. Then four hybridization reactions can be carried out under a single hybridization condition. In other embodiments discussed in more detail below, the SNP-ASOs are conjugated to a surface and hybridized with RCGs.

Conditions for optimal hybridization are described below in the Examples. In general, the SNP-ASO is present in a hybridization mixture at a concentration of from about 0.005 nanomoles per liter SNP-ASO hybridization mixture to about 50 nM SNP-ASO per ml hybridization mixture. More preferably, the concentration is from 0.5 nanomoles per liter to 1 nanomole per liter. A preferred concentration for radioactivity is 0.66 nanomoles per liter. The mixture preferably also includes a hybridization optimizing agent in order to improve signal discrimination between genomic sequences which are identically complementary to the SNP-ASO and those which contain a single mismatched nucleotide (as well as any neutral base etc. substitutions). Isostabilizing agents are compounds such as betaines and lower tetraalkyl ammonium salts which reduce the sequence dependence of DNA thermal melting transitions. These types of compounds also increase discrimination between matched and mismatched SNPs/genomes. A denaturing agent may also be included in the hybridization mixture. A denaturing agent is a composition that lowers the melting temperature of double stranded nucleic acid molecules, generally by reducing hydrogen bonding between bases or preventing hydration of nucleic acid molecules. Denaturing agents are well-known in the art and include, for example, DMSO, formaldehyde, glycerol, urea, formamide, and chaotropic salts. The hybridization conditions in general are those used commonly in the art, such as those described in Sambrook et al., "Molecular Cloning: A Laboratory Manual", (1989), 2nd Ed., Cold Spring Harbor, N.Y.; Berger and Kimmel, "Guide to Molecular Cloning Techniques", *Methods in Enzymology*, (1987), Volume 152, Academic Press, Inc., San Diego, Calif.; and Young and Davis, (1983), *PNAS* (USA) 80:1194.

In general, incubation temperatures for hybridization of nucleic acids range from about 20° C. to 75° C. For probes 17 nucleotides residues and longer, a preferred temperature range for hybridization is from about 50° C. to 54° C. The hybridization temperature for longer probes is preferably from about 55° C. to 65° C. and for shorter probes is less than 52° C. Rehybridization may be performed in a variety of time frames. Preferably, hybridization of SNP and RCGs performed for at least 30 minutes.

Preferably, either or both of the SNP-ASO and the RCG are labeled. The label may be added directly to the SNP-ASO or the RCG during synthesis of the oligonucleotide or during generation of RCG fragments. For instance, a PCR reaction performed using labeled primers or labeled nucleotides will produce a labeled product. Labeled nucleotides (e.g., fluorescein-labeled CTP) are commercially available. Methods for attaching labels to nucleic acids are well known to those of ordinary skill in the art and, in addition to the PCR method, include, for example, nick translation and end-labeling.

Labels suitable for use in the methods of the present invention include any type of label detectable by standard means, including spectroscopic, photochemical, biochemical, electrical, optical, or chemical methods. Preferred types of labels include fluorescent labels such as fluorescein. A fluorescent label is a compound comprising at least one fluorophore. Commercially available fluorescent labels include, for example, fluorescein phosphoramidites such as fluoreprime (Pharmacia, Piscataway, N.J.), fluoredite (Millipore, Bedford, Mass.), FAM (ABI, Foster City, Calif.), rhodamine, polymethadine dye derivative, phosphores, Texas red, green fluorescent protein, CY3, and CY5. Polynucleotides can be labeled with one or more spectrally distinct fluorescent labels. "Spectrally distinct" fluorescent labels are labels which can be distinguished from one another based on one or more of their characteristic absorption spectra, emission spectra, fluorescent lifetimes, or the like. Spectrally distinct fluorescent labels have the advantage that they may be used in combination ("multiplexed").

Radionuclides such as $^3$H, $^{125}$I, $^{35}$S, $^{14}$C, or $^{32}$P are also useful labels according to the methods of the invention. A plurality of radioactively distinguishable radionuclides can be used. Such radionuclides can be distinguished, for example, based on the type of radiation (e.g. α, β, or δ radiation) emitted by the radionuclides. The $^{32}$P signal can be detected using a phosphoimager, which currently has a resolution of approximately 50 microns. Other known techniques, such as chemiluminescence or colorimetric (enzymatic color reaction), can also be used.

By using spectrally distinct fluorescent probes , it is possible to analyze more than one locus a single hybridization mixture. The term "multiplexing" refers to the use of a set of distinct fluorescent labels in a single assay. Such fluorescent labels have been described extensively in the art, such as the fluorescent labels described in PCT Published Patent Application WO98/31834.

Fluorescent primers are a preferred method of labeling polynucleotides. The fluorescent tag is stable for more than a year. Radioactively labeled primers are stable for a shorter period. In addition, fluorescent primers may be used in combination if they are spectrally distinct, as discussed above. This allows multiple hybridizations to be detected in a single hybridization mixture. As a result, the total number of reactions needed for a genome-wide scan is reduced. For example, for analysis of 1000 loci, 2000 hybridizations are needed (1000 loci×2 polymorphisms/loci). The use of 4 fluorescently-labeled oligonucleotides will cut this number 4-fold and thus only 500 hybridizations will be needed.

In order to determine the genotype of an individual at a SNP locus, it is desirable to employ SNP allele-specific oligonucleotide hybridization. Preferably, two hybridization mixtures are prepared for each locus (or they can be performed together). The first hybridization mixture contains a labeled (e.g., radioactive or fluorescent) SNP-ASO (typically 17–21 nucleotide residues in length centered around the polymorphic residue). To increase specificity, a 20–50 fold excess of non-labeled oligonucleotides corresponding to another allele (referred to herein as a "complementary SNP-ASO") is included in the hybridization mixture. Use of the non-labeled complementary SNP-ASO can be avoided by using SNP-ASO containing a neutral base as described below. In the second hybridization mixture, the SNP-ASO that was labeled in the first mixture is not labeled, and the non-labeled SNP-ASO is labeled instead. Hybridization is performed in the presence of a hybridization buffer. The melting temperature of oligonucleotides can be determined empirically for each experiment. The pair of 2 oligonucleotides corresponding to different alleles of the same SNP (the SNP-ASOs and the complementary SNP-ASO) are referred to herein as a pair of allele-specific oligonucleotides (ASOs). Further experimental details regarding selecting and making SNP-ASOs are provided in the Examples section below.

In addition to the method described above, several other methods of allele specific hybridization may be used for hybridizing SNP-ASOs with RCGs. One method is to increase discrimination of SNPs in DNA hybridization by means of artificial mismatches. Artificial mismatches are inserted into oligonucleotide probes using a neutral base such as the base analog 3-nitropyrrole. A significant enhancement of discrimination is generally obtained, with a strong dependence of the enhancement on the spacing between mismatches.

In general, the methods described above are based on conjugation of genomic DNA fragments (i.e. a RCG) to a solid support. Hybridization analysis can also be performed with the SNP-ASO conjugated to the support (e.g. in an array). The oligonucleotide array is hybridized with one or more RCGs. Attaching of the SNP-ASOs or RCGs onto the support may be performed by any method known in the art. Many methods for attaching oligonucleotides to surfaces in arrays have been described, see, e.g. PCT Published Patent Application WO97/29212, U.S. Pat. Nos. 4,588,682; 5,667, 976; and 5,760,130. Other methods include, for example, using arrays of metal pins. Additionally, RCGs may be attached to the surface by the methods disclosed in the Examples below.

An "array" as used herein is a set of molecules arranged in a specific order with respect to a surface. Preferably the array is composed of polynucleotides (e.g. either SNP-ASOs or RCGs) attached to the surface. Oligonucleotide arrays can be used to screen nucleic acid samples for a target nucleic acid, which can be labeled with a detectable marker. A fluorescent signal resulting from hybridization between a target nucleic acid and a substrate-bound oligonucleotide provides information relating to the identity of the target nucleic acid by reference to the location of the oligonucleotide in the array on the substrate. Such a hybridization assay can generate thousands of signals which exhibit different signal strengths. These signals correspond to particular oligonucleotides of the array. Different signal strengths will arise based on the amount of labeled target nucleic acid hybridized with an oligonucleotide of the array. This amount, in turn, can be influenced by the proportion of AT-rich regions and GC-rich regions within the oligonucleotide (which determines thermal stability). The relative amounts of hybridized target nucleic acid can also be influenced by, for example, the number of different probes arrayed on the substrate, the length of the target nucleic acid, and the degree of hybridization between mismatched residues. Oligonucleotide arrays, in some embodiments, have a density of at least 500 features per square centimeter, but in practice can have much lower densities. A feature, as used herein, is an area of a substrate on which oligonucleotides having a single sequence are immobilized.

The oligonucleotide arrays of the invention may be produced by any method known in the art. Many such arrays are commercially available, and many methods have been described for producing them. One preferred method for producing arrays includes spatially directed oligonucleotide synthesis. Spatially directed oligonucleotide may be performed using light-directed oligonucleotide synthesis, microlithography, application by ink jet, microchannel deposition to specific location, and sequestration with physical barriers. Each of these methods is well-known in the art and has been described extensively. For instance, the light-directed oligonucleotide synthesis method has been disclosed in U.S. Pat. Nos. 5,143,854; 5,489,678; and 5,571,639; and PCT applications having publication numbers WO90/15070; WO92/10092; and WO94/12305. This technique involves modification of the surface of the solid support with linkers and photolabile protecting groups using a photolithographic mask to produce reactive (e.g. hydroxyl) groups in the illuminated regions. A 3'-O-phosphoramide-activated deoxynucleocide having a 5'-hydroxyl protected group is supplied to the surface such that coupling occurs at sites that were exposed to light. The substrate is rinsed, and the surface is illuminated with a second mask, and another activated deoxynucleotide is presented to the surface. The cycle is repeated until the desired set of products is obtained. After the cycle is finished, the nucleotides can be capped. Another method involves mechanically protecting portions of the surface and selectively deprotecting/coupling materials to the is exposed portions of the surface, such as the method described in U.S. Pat. No. 5,384,261. The mechanical means is generally referred to as a mask. Other methods for array preparation are described in PCT Published Patent Applications WO97/39151, WO98/20967, and WO98/10858, which describe an automated apparatus for the chemical synthesis of molecular arrays, U.S. Pat. No. 5,143,854, Fodor et al., *Science* (1991), 251:767–777 and Kozal et al., *Nature Medicine*, v. 2, p. 753–759 (1996).

Hybridizing a SNP-ASO with an array of RCGs (or hybridizing a RCG with an array of SNP ASO) is followed by detection of hybridization. Part of the genotyping methods described herein is to determine if a positive or negative signal exists for each hybridization for an individual and then based on this information, determine the genotype for the corresponding SNP locus. This step is relatively straightforward, but varies depending on the method of detection. Essentially, all of the detection methods described here (fluorescent, radioactive, etc.) can be reduced to a digital image file, e.g. using a microarray reader or phosphoimager. Presently, there are several software products which will overlay a grid on an image and determine the signal strength value for each element of the grid. These values can be imported into a computer program, such as the Microsoft Corporation spreadsheet program designated Microsoft Excel™, with which simple analysis can be performed to assign each signal a manipulable value (e.g. 1 or 0 or + or −). Once this is accomplished, an individual's genotype can be described in terms of the pattern of hybridization of RCG fragments obtained from the individual with selected SNP ASO corresponding to disease-associated SNPs.

The array having labeled SNP-ASOs (or labeled RCGs) hybridized thereto can be analyzed using automated equipment. Automated equipment for analyzing arrays can include an excitation radiation source which emits radiation at a first wavelength, an optical detector, and a stage for securing the surface supporting the array. The excitation source emits excitation radiation which is focused on at least one area of the array and which induces emission from fluorescent labels. The signal is preferably in the form of radiation having a different wavelength than the excitation radiation. Emitted radiation is collected by a detector, which generates a signal proportional to the amount of radiation sensed thereon. The array may then be moved so that a different area can be exposed to the radiation source to produce a signal. Once each area of the array has been scanned, a two-dimensional image of the array is obtained. Preferably, the movement of the array is accomplished using automated equipment, such as a multi-axis translation stage, such as one which moves the array at a constant velocity. In alternative embodiments, the array may remain stationary, and devices may be employed to cause scanning of the light over the stationary array.

One type of detection method includes a CCD imaging system, e.g. when the nucleic acids are labeled with fluorescent probes. Other detectors are well known to those of skill in the art and also, or alternatively, be used. CCD imaging systems for use with array detection have been described. For instance, a photodiode detector may be placed on the opposite side of the array from the excitation source. Alternatively, a CCD camera may be used in place of the photodiode detector to image the array. One advantage of using these systems is rapid read time. In general, an entire 50×50 centimeter array can be read in about 30 seconds or less using standard equipment. If more powerful equipment and efficient dyes are used, the read time may be reduced to less than 5 seconds.

Once the data is obtained, e.g. as a two-dimensional image, a computer can be used to transform the data into a displayed image which varies in color depending on the intensity of light emission at a particular location. Any type of commercial software which can perform this type of data analysis can be used. In general, the data analysis involves the steps of determining the intensity of the fluorescence emitted as a function of the position on the substrate, removing the outliers, and calculating the relative binding affinity. One or more of the presence, absence, and intensity of signal corresponding to a label is used to assess the presence or absence of an SNP corresponding to the label in the RCG. The presence and absence of one or more SNP's in a RCG can be used to assign a genotype to the individual. For example, the following depicts the genotype analysis of 3 individuals at a given locus at which an A/G polymorphism occurs:

| Individual | SNP 1 Allele "A" | SNP 1 Allele "G" | Genotype |
|---|---|---|---|
| Larry | + | − | A/A |
| Moe | − | + | G/G |
| Curly | + | + | A/G |

As mentioned above, SNP analysis can be used to determine whether an individual has or will develop a particular phenotypic trait and whether the presence or absence of a specific allele correlates with a particular phenotypic trait. In order to determine which SNPs are related to a particular phenotypic trait, genomic samples are isolated from a group of individuals which exhibit the particular phenotypic trait, and the samples are analyzed for the presence of common SNPs. The genomic sample obtained from each individual is used to prepare a RCG. These RCGs are screened using panels of SNPs in a high throughput method of the invention to determine whether the presence or absence of a particular allele is associated with the phenotype. In some cases, it may be possible to predict the likelihood that a particular subject will exhibit the related phenotype. If a particular polymorphic allele is present in 30% of individuals who develop Alzheimer's disease, then an individual having that allele has a higher likelihood of developing Alzheimer's disease. The likelihood can also depend on several factors such as whether individuals not afflicted with Alzheimer's disease have this allele and whether other factors are associated with the development of Alzheimer's disease. This type of analysis can be useful for determining a probability that a particular phenotype will be exhibited. In order to increase the predictive ability of this type of analysis, multiple SNPs associated with a particular phenotype can be analyzed. Although values can be calculated, it is enough to identify that a difference exists.

It is also possible to identify SNPs which segregate with a particular disease. Multiple polymorphic sites may be detected and examined to identify a physical linkage between them or between a marker (SNP) and a phenotype. Both of these are useful for mapping a genetic locus linked to or associated with a phenotypic trait to a chromosomal position and thereby revealing one or more genes associated with the phenotypic trait. If two polymorphic sites segregate randomly, then they are either on separate chromosomes or are distant enough, with respect to one another on the same chromosome that they do not co-segregate. If two sites co-segregate with significant frequency, then they are linked to one another on the same chromosome. These types of linkage analyses are useful for developing genetic maps. See e.g., Lander et al., PNAS (USA) 83, 7353–7357 (1986), Lander et al., Genetics 121, 185–199 (1989). The invention is also useful for identifying polymorphic sites which do not segregate, i.e., when one sibling has a chromosomal region that includes a polymorphic site and another sibling does not have that region.

Linkage analysis is often performed on family members which exhibit high rates of a particular phenotype or on patients suffering from a particular disease. Biological samples are isolated from each subject exhibiting a phenotypic trait, as well as from subjects which do not exhibit the phenotypic trait. These samples are each used to generate individual RCGs and the presence or absence of polymorphic markers is determined using panels of SNPs. The data can be analyzed to determine whether the various SNPs are associated with the phenotypic trait and whether or not any SNPs segregate with the phenotypic trait.

Methods for analyzing linkage data have been described in many references, including Thompson & Thompson, Genetics in Medicine (5th edition), W.B. Saunders Co., Philadelphia, 1991; and Strachan, "Mapping the Human Genome" in the Human Genome (Bios Scientific Publishers Ltd., Oxford) chapter 4, and summarized in PCT published patent application WO98/18967 by Affymetrix, Inc. Linkage analysis involving by calculating log of the odds values (LOD values) reveals the likelihood of linkage between a marker and a genetic locus at a recombination fraction, compared to the value when the marker and genetic locus are not linked. The recombination fraction indicates the likelihood that markers are linked. Computer programs and mathematical tables have been developed for calculating LOD scores of different recombination fraction values and determining the recombination fraction based on a particular LOD score, respectively. See e.g., Lathrop, PNAS, USA 81, 3443–3446 (1984); Smith et al., Mathematical Tables for Research Workers in Human Genetics (Churchill, London, 1961); Smith, Ann. Hum. Genet. 32, 127–1500 (1968). Use of LOD values for genetic mapping of phenotypic traits is described in PCT published patent application WO98/18967 by Affymetrix, Inc. In general, a positive LOD score value indicates that two genetic loci are linked and a LOD score of +3 or greater is strong evidence that two loci are linked. A negative value suggests that the linkage is less likely.

The methods of the invention are also useful for assessing loss of heterozygosity in a tumor. Loss of heterozygosity in a tumor is useful for determining the status of the tumor, such as whether the tumor is an aggressive, metastatic tumor. The method is generally performed by isolating genomic DNA from tumor sample obtained from a plurality of subjects having tumors of the same type, as well as from normal (i.e., non-cancerous) tissue obtained from the same subjects. These genomic DNA samples are used to generate RCGs which can be hybridized with a SNP-ASO, for example using the surface array technology described herein. The absence of a SNP allele in the RCG generated from the tumor compared to the RCG generated from normal tissue indicates whether loss of heterozygosity has occurred. If a SNP allele is associated with a metastatic state of a cancer, the absence of the SNP allele can be compared to its presence or absence in a non-metastatic tumor sample or a normal tissue sample. A database of SNPs which occur in normal and tumor tissues can be generated and an occurrence of SNPs in a patient's sample can be compared with the database for diagnostic or prognostic purposes.

It is useful to be able to differentiate non-metastatic primary tumors from metastatic tumors, because metastasis is a major cause of treatment failure in cancer patients. If metastasis can be detected early, it can be treated aggressively in order to slow the progression of the disease. Metastasis is a complex process involving detachment of cells from a primary tumor, movement of the cells through the circulation, and eventual colonization of tumor cells at local or distant tissue sites. Additionally, it is desirable to be able to detect a predisposition for development of a particular cancer such that monitoring and early treatment may be initiated. Many cancers and tumors are associated with genetic alterations. For instance, an extensive cytogenetic analysis of hematologic malignancies such as lymphomas and leukemias have been described, see e.g., Solomon et al., Science 254, 1153–1160, 1991. Many solid tumors have complex genetic abnormalities requiring more complex analysis.

Solid tumors progress from tumorigenesis through a metastatic stage and into a stage at which several genetic aberrations can occur. e.g., Smith et al., Breast Cancer Res. Terat., 18 Suppl. 1, S5–14, 1991. Genetic aberrations are believed to alter the tumor such that it can progress to the next stage, i.e., by conferring proliferative advantages, the ability to develop drug resistance or enhanced angiogenesis, proteolysis, or metastatic capacity. These genetic aberrations are referred to as "loss of heterozygosity." Loss of heterozygosity can be caused by a deletion or recombination resulting in a genetic mutation which plays a role in tumor progression. Loss of heterozygosity for tumor suppressor genes is believed to play a role in tumor progression. For instance, it is believed that mutations in the retinoblastoma tumor suppressor gene located in chromosome 13q14 causes progression of retinoblastomas, osteosarcomas, small cell lung cancer, and breast cancer. Likewise, the short arm of chromosome 3 has been shown to be associated with cancer such as small cell lung cancer, renal cancer and ovarian cancers. For instance, ulcerative colitis is a disease which is associated with increased risk of cancer presumably involving a multistep progression involving accumulated genetic changes (U.S. Pat. No. 5,814,444). It has been shown that patients afflicted with long duration ulcerative colitis exhibit an increased risk of cancer, and that one early marker is loss of heterozygosity of a region of the distal short arm of chromosome 8. This region is the site of a putative tumor suppressor gene that may also be implicated in prostate and breast cancer. Loss of heterozygosity can easily be detected by performing the methods of the invention routinely on patients afflicted with ulcerative colitis. Similar analyses can be performed using samples obtained from other tumors known or believed to be associated with loss of heterozygosity.

The methods of the invention are particularly advantageous for studying loss of heterozygosity because thousands of tumor samples can be screened at one time. Additionally, the methods can be used to identify new regions of loss that have not previously been identified in tumors.

The methods of the invention are useful for generating a genomic pattern for an individual genome of a subject. The genomic pattern of a genome indicates the presence or absence of polymorphisms, for example, SNPs, within a genome. Genomic DNA is unique to each individual subject (except identical twins). Accordingly, the more polymorphisms that are analyzed for a given genome of a subject, the higher probability of generating a unique genomic pattern for the individual from which the sample was isolated. The genomic pattern can be used for a variety of purposes, such as for identification with respect to forensic analysis or population identification, or paternity or maternity testing. The genomic pattern may also be used for classification purposes as well as to identify patterns of polymorphisms within different populations of subjects.

Genomic patterns may be used for many purposes, including forensic analysis and paternity or maternity testing. The use of genomic information for forensic analysis has been described in many references, see e.g., National Research Council, The Evaluation of Forensic DNA Evidence (EDS Pollard et al., National Academy Press, DC, 1996). Forensic analysis of DNA is based on determination of the presence or absence of alleles of polymorphic regions within a genomic sample. The more polymorphisms that are analyzed, the higher probability of identifying the correct individual from which the sample was isolated.

In an embodiment of the invention, when a biological sample, such as blood or sperm, is found at a crime scene, DNA can be isolated and RCGs can be prepared. This RCG can then be screened with a panel of SNPs to generate a genomic pattern. The genomic pattern can be matched with a genomic pattern produced from a suspect or compared to a database of genomic patterns which has been compiled. Preferably, the SNPs used in the analysis are those in which the frequency of the polymorphic variation (allelic frequency) has been determined, such that a statistical analysis can be used to determine the probability that the sample genome matches the suspect's genome or a genome within the database. The probability that two individuals have the same polymorphic or allelic form at a given genetic site is described in detail in PCT published patent application WO98/18967, the entire contents of which are hereby incorporated by reference. Briefly, this probability defined as P(ID) can be determined by the equation:

$$P(ID)=(x^2)^2+(2xy)^2+(y^2)^2$$

x and y in the equation represent the frequency that an allele A or B will occur in a haploid genome.

The calculation can be extended for more polymorphic forms at a given locus. The predictability increases with the number of polymorphic forms tested. In a locus of n alleles, a binomial expansion is used to calculate P(ID). The probabilities of each locus can be multiplied to provide the cumulative probability of identity and from this the cumulative probability of non-identity for a particular number of loci can be calculated. This value indicates the likelihood that random individuals have the same loci. The same type of quantitative analysis can be used to determine whether a subject is a parent of a particular child. This type of information is useful in paternity testing, animal breeding studies, and identification of babies or children whose identity has been confused, e.g., through adoption or inadequate record keeping in a hospital, or through separation of families by occurrences such as earthquake or war.

The genomic pattern may be used to generate a genomic classification code (GNC). The GNC may be represented by one or more data signals and stored as part of a data structure on a computer-readable medium, for example, a database. The stored GNCs may be used to characterize, classify, or identify the subjects for which the GNCs were generated. Each GNC may be generated by representing the presence or absence of each polymorphism with a computer-readable signal. These signals may then be encoded, for example, by performing a function on the signals.

Accordingly, the GNCs may be used as part of a classification or identification system for subjects such as, for example, humans, plants, or animals. As discussed above, the more polymorphisms that are analyzed for a given genome of a subject, the higher probability of generating a unique genomic pattern for the individual from which the sample was isolated, and consequently, the higher the probability that the GNC uniquely identifies an individual. In such a system, a data structure may include a plurality of entries, for example, data records or table entries, where each entry identifies an individual. Each entry may include the GNC generated for the individual as well as other. The GNC or portions thereof may then be stored in an index data structure, for example, another table. A portion of a GNC may be indexed so that each GNC may be further classified by a portion of its genomic pattern as opposed to only the entire genomic pattern.

The data structures may then be searched to identify an individual who has committed a crime. For example, if a biological sample from the individual (such as blood) is recovered from the crime scene, the GNC of the individual may generated by the methods described herein, and a database of records including GNCs searched until a match is found. Thus, the GNCs may be used to classify individuals within a group such as soldiers in the armed forces, cattle in a herd, or produce within a specific crop. For example, the armed forces may generate a database containing the GNC of each soldier, and the database could be used to identify the soldier if necessary. Likewise, a database could be generated where records and indexes of the database include the GNCs of individual animals within a herd of cattle, so that lost or stolen animals could later be identified and returned to the proper owner.

The code may optionally be converted into a bar code or other human- or machine-readable form. For example, each line of a bar code may indicate the presence of specific polymorphisms or groups of specific polymorphisms for a particular subject.

Additionally, it is useful to be able to identify the genus, species, or other taxonomic classification to which an organism belongs. The methods of the invention can accomplish this in a high throughput manner. Taxonomic identification is useful for determining the presence and identity of a pathogenic organism such as a virus, bacteria, protozoa, or multicellular parasites in a tissue sample. In most hospitals, bacteria and other pathogenic organisms are identified based on morphology, determination of nutritional requirements or fermentation patterns, determination of antibiotic resistance, comparison of isoenzyme patterns, or determination of sensitivity to bacteriophage strains. These types of methods generally require approximately 48 to 72 hours to identify the pathogenic organism. More recently, methods for identifying pathogenic organisms have been focused on genotype analysis, for instance, using RFLPs. RFLP analysis has been performed using hybridization methods (such as southern blots) and PCR assays.

Figure 5:
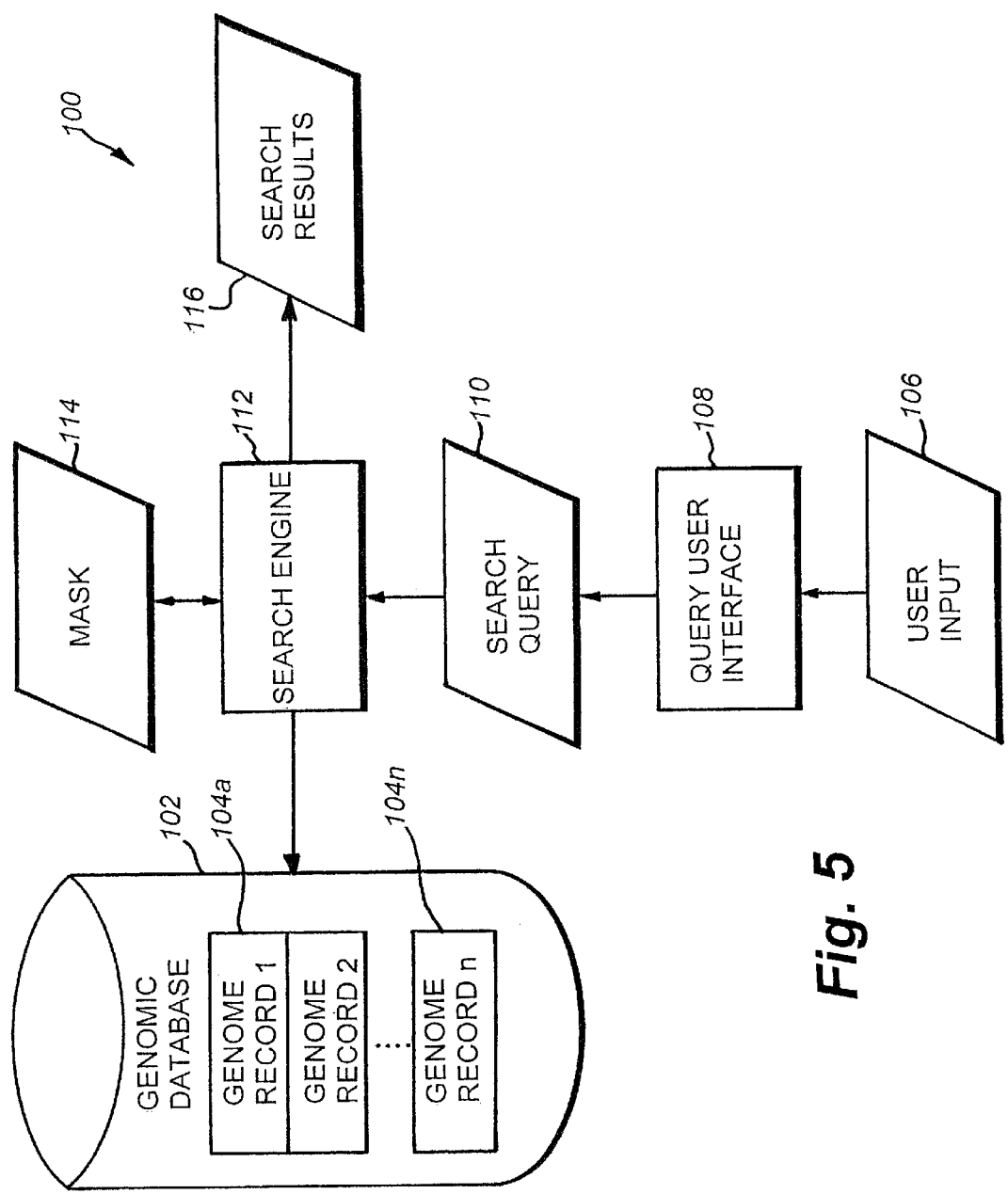
FIG. 5 is a block diagram of a computer system for storing and manipulating genomic information.

The information generated according to the methods of the invention and in particular the GNCs, can be included in a data structure, for example, a database, on computer-readable medium, wherein the information is correlated with other information pertaining to the genomes or the subjects or types of subjects, from which the genomes are obtained. FIG. 5 shows a computer system 100 for storing and manipulating genomic information. The computer system 100 includes a genomic database 102 which includes a plurality of records 104a–n storing information corresponding to a plurality of genomes. Each of the records 104a–n may store genetic information about each genome or an RCG generated therefrom. The genomes for which information is stored in the genomic database 102 may be any kind of genomes from any type of subject. For example, the genomes may represent distinct genomes of individual members of a species, particular classes of the individuals, ie., army, prisoners, etc.

Figure 6A:
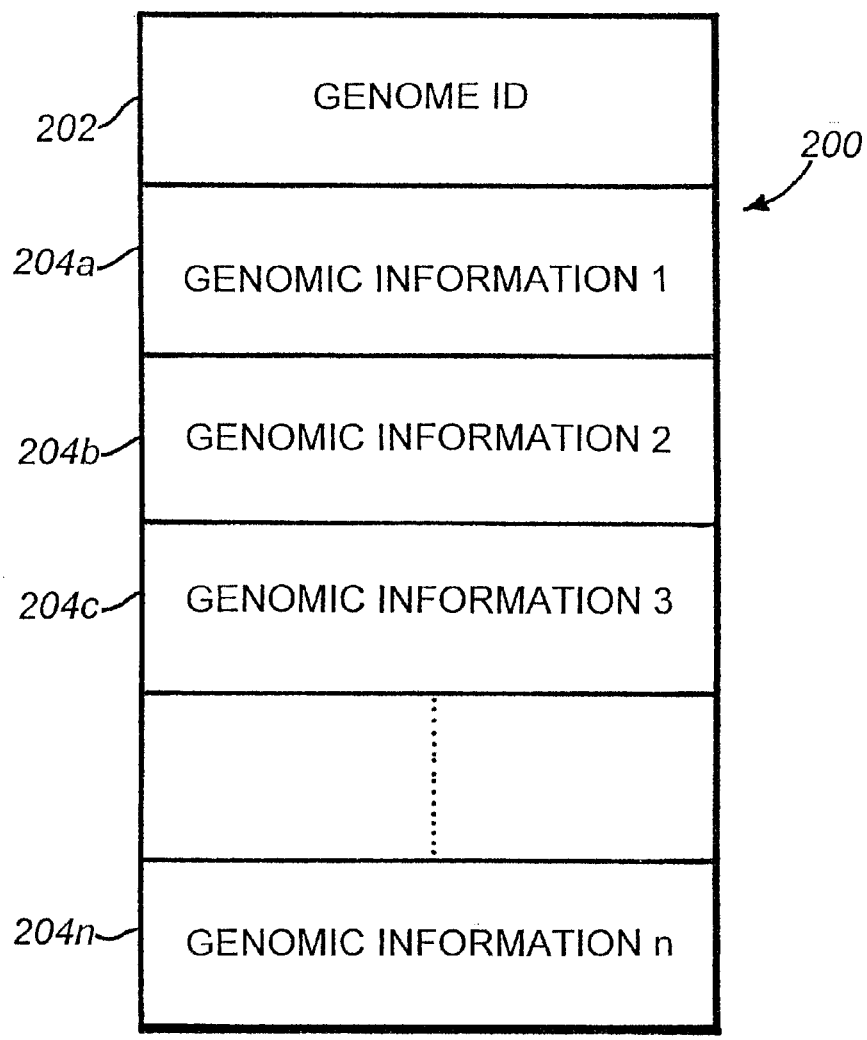
FIG. 6A is an example of a record for storing information about a genome and/or genes or SNPs within the genome.

An example of the format of a record 200 in the genomic database 102 (i.e., one of the records 104a–n) is shown in FIG. 6A. As shown in FIG. 6A, the record 200 includes a genome identifier (Genome ID) 202 that identifies the genome corresponding to the record 200. If enough polymorphisms of the genome were analyzed to generate the spectral pattern (such that the possibility that the GNC uniquely identifies the genome is high), or if a group to which the genome belongs has few enough members, than the GNC of the genome could serve as the Genome ID 202. The record 202 also may include genomic information fields 204a–n. The genomic information may be any information associated with the genome identified by the Genome ID 202 such as, for example, a GNC, a portion of a GNC, the presence or absence of a particular SNP, a genetic attribute (genotype), a physical attribute (phenotype), a name, a taxonomic identifier, a classification of the genome, a description of the individual from which the genome was taken, a disease of the individual, a mutation, a color, etc. Each information field 204a–n may be used as an entry in an index data structure that has a structure similar to record 200. For example, each entry of the index data structure may include an indexed information field as a first data element, and one or more Genome IDs 202 as additional elements, such that all elements that share a common attribute are stored in a common data structure. The format of the record 200 shown in FIG. 6A is merely an example of a format that may be used to represent genomes in the genomic database 102. The amount of information stored for each record 200, the number of records 200, and the number of fields indexed may vary.

Figure 6B:
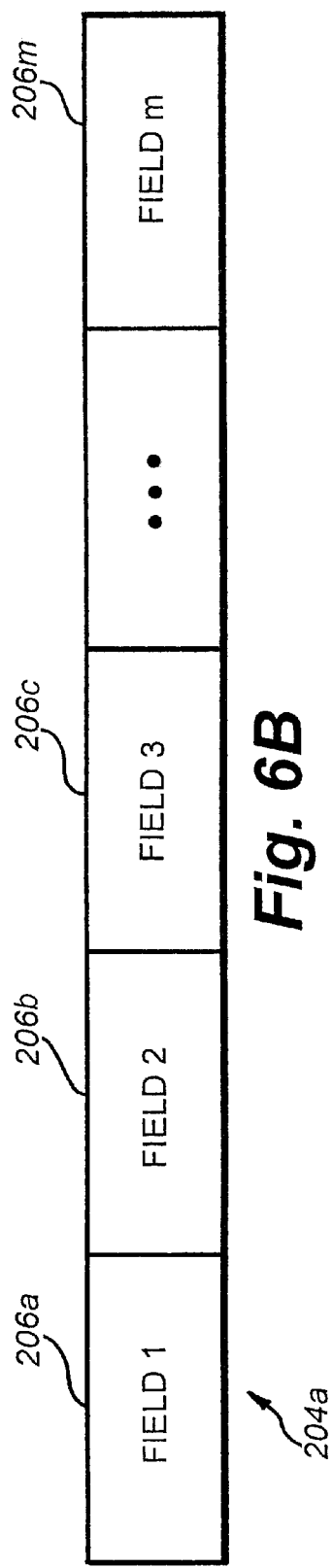
FIG. 6B is an example of a record for storing genomic information.

Further, each information field 204a–n may include one or more fields itself, and each of these fields themselves may include more fields, etc. Referring to FIG. 6B, an embodiment of the information field 204a is shown. The information field 204a includes a plurality of fields 206a–m for storing more information about the information represented by information field 204a. Although the following description refers to the fields 206a–m of the gene ID 204a, such description is equally applicable to information fields 204b–n. For example, if information field 204a represented a GNC of the genome corresponding to the genome ID 202, then each of the fields 206a–m may represent a portion of the GNC, a particular SNP of the genomic pattern from which the GNC was generated, a group of such SNPs, a description of the GNC, a description of a one of the SNPs, etc.

The fields 206a–m of the gene ID 204a may store any kind of value that is capable of being stored in a computer readable medium such as, for example, a binary value, a hexadecimal value, an integral decimal value, or a floating point value.

A user may perform a query on the genomic database 102 to search for genomic information of interest, for example, all genomes having a GNC that matches the GNC of a murder suspect. In another example, it may be known that a biological sample contains a particular sequence. That sequence can be compared with sequences in the database to identify information such as which individual the sample was isolated from, or whether the genetic sequence corresponds to a particular phenotypic trait. For example, the user may search the genomic database 102 for genetic matches to identify an individual, genotypes which correlate with a particular phenotype, genotypes associated with various classes of individuals etc. Referring to FIG. 5, a user may provide user input 106 indicating genomic information for which to search to a query user interface 108. The user input 106 may, for example, indicate an SNP for which to search using a standard character-based notation. The query user interface 108 may, for example, provide a graphical user interface (GUI) which allows the user to select from a list of types of accessible genomic information using an input device such as a keyboard or a mouse.

The query user interface 108 generates a search query 110 based on the user input 106. A search engine 112 receives the search query 110 and generates a mask 114 based on the search query. Example formats of the mask 114 and ways in which the mask 114 may be used to determine whether the genomic information specified by the mask 114 matches genomic information of genomes in the genomic database 102 are described in more detail below with respect to FIG. 7. The search engine 112 determines whether the genomic information specified by the mask 114 matches genomic information of genomes stored in the genomic database 102.

As a result of the search, the search engine 112 generates search results 116 indicating whether the genomic database 102 includes genomes having the genomic information specified by the mask 114. The search results 116 may also indicate which genomes in the genomic database 102 have the genomic information specified by the mask 114.

If, for example, the user input 106 specified a sequence of a gene, a GNC, or an SNP, the search results 116 may indicate which genomes in the genomic database 102 include the specified sequence, GNC, or SNP. If the user input 106 specified particular genetic information concerning a genome (e.g., enough to identify an individual), the search results 116 may indicate which individual genome listed in the genomic database 102 matches the particular information, thus identifying the individual from whom the sample was taken. Similarly, if the user input 106 specified genetic sequences which are not adequate to specifically identify the individual, the search results 116 may still be adequate to identify a class of individuals that have genomes in the genomic database 102 that match the genetic sequence. For example, the search results may indicate that the genomic information of genomes of all caucasian males matches the specified genetic sequence.

Figure 7:
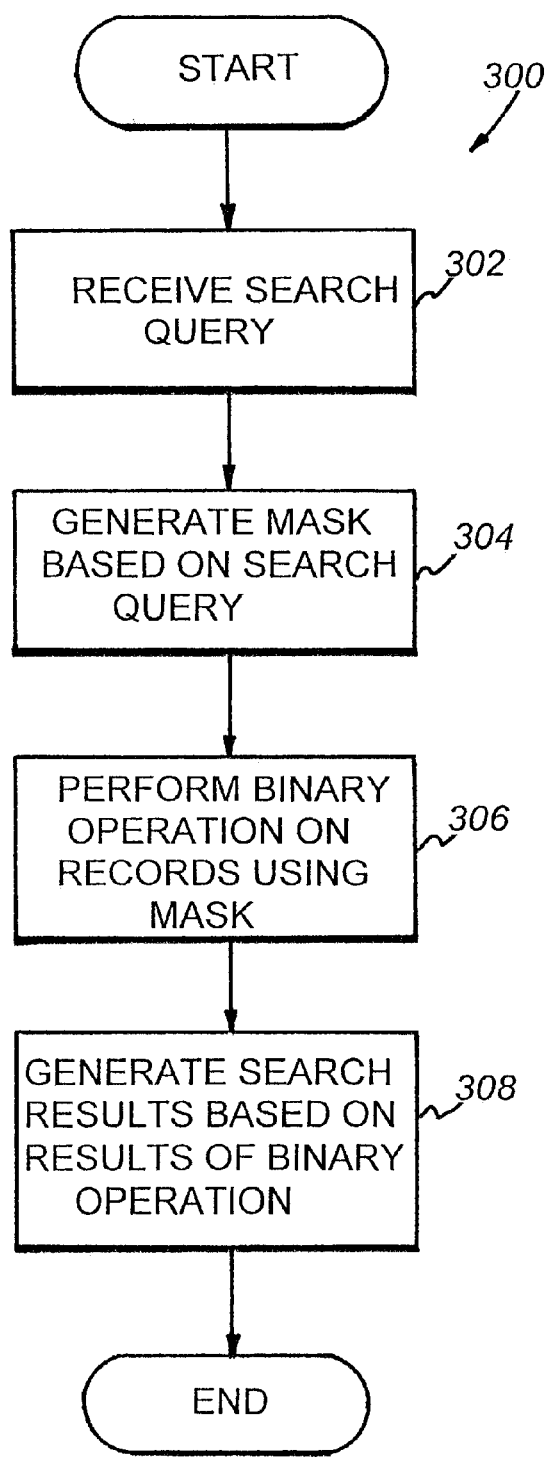
FIG. 7 is a flow chart of a method for determining whether genomic information of a sample genome such as SNPs match that of another genome.

FIG. 7 illustrates a process 300 that may be used by the search engine 112 to generate the search results 116. The search engine 112 receives the search query 110 from the query user interface 108 (step 302). The search engine 112 generates the mask 114 generated based on the search query 110 (step 304). The search engine 112 performs a binary operation on one or more of the records 104*a–n* in the genomic database 102 using the mask 114 (step 306).

The search engine 112 generates the search results 116 based on the results of the binary operation performed in step 306 (step 308).

A computer system for implementing the system 100 of FIG. 5 as a computer program typically includes a main unit connected to both an output device which displays information to a user and an input device which receives input from a user. The main unit generally includes a processor connected to a memory system via an interconnection mechanism. The input device and output device also are connected to the processor and memory system via the interconnection mechanism.

One or more output devices may be connected to the computer system. Example output devices include a cathode ray tube (CRT) display, liquid crystal displays (LCD), printers, communication devices such as a modem, and audio output. One or more input devices may be connected to the computer system. Example input devices include a keyboard, keypad, track ball, mouse, pen and tablet communication device, and data input devices such as sensors. The invention is not limited to the particular input or output devices used in combination with the computer system or to those described herein.

The computer system may be a general purpose computer system which is programmable using a computer programming language, such as for example, C++, Java, or other language, such as a scripting language or assembly language. The computer system may also include specially programmed, special purpose hardware such as, for example, an application-specific integrated circuit (ASIC). In a general purpose computer system, the processor is typically a commercially available processor, of which the series x86, Celeron, and Pentium processors, available from Intel, and similar devices from AMD and Cyrix, the 680X0 series microprocessors available from Motorola, the PowerPC microprocessor from IBM and the Alpha-series processors from Digital Equipment Corporation, are examples.

Many other processors are available. Such a microprocessor executes a program called an operating system, of which Windows NT, Linux, UNIX, DOS, VMS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory, and tape are examples. The disk may be removable such as, for example, a floppy disk or a read/write CD, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk after processing is completed. A variety of mechanisms are known for managing data movement between the disk and the integrated circuit memory element, and the invention is not limited to any particular mechanism. It should also be understood that the invention is not limited to a particular memory system.

The invention is not limited to a particular computer platform, particular processor, or particular high-level programming language. Additionally, the computer system may be a multiprocessor computer system or may include multiple computers connected over a computer network. It should be understood that each module (e.g. 108, 112) in FIG. 5 may be a separate module of a computer program, or may be a separate computer program. Such modules may be operable on separate computers. Data (e.g. 102, 106, 110, 114, and 116) may be stored in a memory system or transmitted between computer systems. The invention is not limited to any particular implementation using software, hardware, firmware, or any combination thereof. The various elements of the system, either individually or in combination, may be implemented as a computer program product tangibly embodied in a machine-readable storage device for execution by a computer processor. Various steps of the process, for example, steps 302, 304, 306, and 308 of FIG. 7, may be performed by a computer processor executing a program tangibly embodied on a computer-readable medium to perform functions by operating on input and generating output. Computer programming languages suitable for implementing such a system include procedural programming languages, object-oriented programming languages, and combinations of the two.

The invention also encompasses compositions. One composition of the invention is a plurality of RCGs immobilized on a surface, where the plurality of RCGs are prepared by DOP-PCR. Another composition is a panel of SNP-ASOs immobilized on a surface, wherein the SNPs are identified by using RCGs as described above.

The invention also includes kits having a container housing a set of PCR primers for reducing the complexity of a genome and a container housing a set of SNP-ASOs, particularly wherein the SNPs are present with a frequency of at least 50 or 55% in a RCG made using the primer set. In some kits, the set of PCR primers are primers for DOP-PCR and preferably the DOP-PCR primer has the tag-(N)$_x$-TARGET structure described herein, i.e., wherein the TARGET includes at least 7 arbitrarily selected nucleotide residues, wherein x is an integer from 3 to 9, and wherein each N is any nucleotide residue and wherein tag is a polynucleotide as described above. In some embodiments the SNPs in the kit are attached to a surface such as a slide.

SNPs identified according to the methods of the invention using the B1 5' rev primer the following:

B1 5' rev ATTAAAGGCGTGCGCCACCATGCC (SEQID #13)

| locus | ASO | Allele | Strain | (SEQ ID #) |
|---|---|---|---|---|
| 1 | tttatgAaggCataaaaa | A | 129/ | 14 |
|  | tttatgGaggCataaaaa | B | B6-DBA | 15 |
|  | tttatgAaggTataaaaa | C | Spre | 16 |
| 2 | ctgggctgTattcattt | A | 129-DBA | 17 |
|  | ctgggctgCattcattt | B | B6 | 18 |
|  | tctGcctccTGagtgct | C | B6-129-DBA | 19 |
|  | tctAcctccCAagtgct | D | Spre | 20 |
| 3 | tagctagaAtcaagctt | A | B6 | 21 |
|  | tagctagaGtcaagctt | B | DBA-Spre | 22 |
| 4 | gctgtgcAACaaatcac | A | 129/ | 23 |
|  | cagctgtgc---aaatcacc | B | B6 | 24 |
| 5 | tttcgtga-tgtttctat | A | 129-Spre | 25 |
|  | tttcgtgaAtgtttcta | B | B6-DBA | 26 |
| 6 | cactgtctAcatcttta | A | B6-129 | 27 |
|  | cactgtctCcatcttta | B | DBA-Spre | 28 |
| 7 | taacattcTtgaagcca | A | 129-DBA-Spre | 29 |
|  | taacattcCtgaagcca | B | B6 | 30 |
| 8 | gcttccaTttcctaagg | A | 129-DBA | 31 |
|  | gcttccaCttcctaagg | B | B6 | 32 |
| 9 | aggaatgGcAataatcc | A | B6-129 | 33 |
|  | aggaatgGcGataatcc | B | DBA | 34 |
|  | aggaatgAcAataatcc | C | Spre | 35 |
|  | ttaaattcGtaaatgga | D | B6-129-DBA | 36 |
|  | ttaaattcAtaaatgga | E | Spre | 37 |
| 10 | taacattcTtgaagcca | A | 129-DBA-Spre | 38 |
|  | taacattcCtgaagcca | B | B6 | 39 |
| 11 | ttcTGtgActccaCttg | A | 129 | 40 |
|  | ttcTGtgActccaTttg | B | B6-DBA | 41 |
|  | ttcCCtgTctccaTttg | C | Spre | 42 |
| 12 | gtagtttgCcaggaacc | A | 129-Spre | 43 |
|  | gtagtttgTcaggaacc | B | B6-DBA | 44 |
| 13 | tgctactcctctctactcg | A | 129 | 45 |
|  | tgctattcctctctgctcg | B | B6-DBA-Spre | 46 |
|  | cttgatcaccctctgatga | C | B6-129-DBA | 47 |
|  | cttggtcaccctctaatga | D | Spre | 48 |
| 14 | gaggtggtgcagagtga | A | 129-DBA | 49 |
|  | gaggtggcgcagagtga | B | B6 | 50 |
|  | gaggtggcccagagtga | C | Spre | 51 |
| 15 | cccactgaaccgcacag | A | 129-DBA | 52 |
|  | cccactgagctgcacag | B | B6 | 53 |
|  | cccactcagccgcacag | C | Spre | 54 |
| 16 | tgaagacacagccagcc | A | 129-DBA | 55 |
|  | tgaagacgcagccagcc | B | B6 | 56 |
|  | tgaagacgaagccagcc | C | Spre | 57 |
| 17 | agaagttggtaccaggg | A | 129/FVB/F1/cast/spre | 58 |
|  | agaagttgttaccaggg | B | B6 | 59 |
| 18 | tatgattacgtaatgtt | A | 129/B6/F1 | 60 |
|  | tatgattatgtaatgtt | B | FVB/F1 | 61 |
| 19 | atgattccagtgagtta | A | 129/B6 | 62 |
|  | atgattcctgtgagtta | B | FVB/F1 | 63 |
|  | catactattaacactggaa | C | Cast-129 | 64 |
|  | catattattaacacaggaa | D | Spre | 65 |
| 20 | gtcaagaacaggcaata | A | 129/b6/f1/FVB | 66 |
|  | gtcaagaataggcaata | B | f1 | 67 |
|  | cagactagggaaccttc | C | 129 | 68 |
|  | cagacgagggaaccttc | E | Spre | 69 |
|  | cagactagggagccttc | D | Cast | 70 |
| 21 | tgtccagttgtttgcat | A | 129/ | 71 |
|  | tgtccagtcgtttgcat | B | b6/fvb/f1 | 72 |
|  | ggggtagccagtttggt | C | Cast-129 | 73 |
|  | ggggtagcaagtttggt | D | Spre | 74 |
| 22 | caggaagctgtagctcc | A | 129/f1 | 75 |
|  | caggaagccgtagctcc | B | b6/fvb | 76 |
|  | cctgagcctgtctacct | C | Cast-129 | 77 |
|  | cctgagcccgtctacct | D | Spre | 78 |
| 23 | taacattcttgaagcca | A | 129/FVB/F1/cast/spre | 79 |

-continued

|    | sequence | | | |
|----|----------|---|---|---|
|    | taacattcctgaagcca | B | B6 | 80 |
| 24 | ccaactgaaccgcacag | A | 129/FVB | 81 |
|    | ccaactgagctgcacag | B | B6 | 82 |
|    | gagctagctcacacattct | C | Cast-129 | 83 |
|    | gagttagctcacacgttct | D | Spre | 84 |
| 25 | acgggggggtggcgtta | A | 129/f1 | 85 |
|    | acggggggg-tggcgttaa | B | b6/fvb/cast/spre | 86 |
|    | tagacagccagcgcgtcac | C | Cast-129 | 87 |
|    | tagatagccagcgcatcac | D | Spre | 88 |
| 26 | gcttttcttgagagtggc | A | 129/b6 | 89 |
|    | gcttttctttagagtggc | B | fvb | 90 |
|    | gcttttcgtgagagtggc | C | f1 | 91 |
| 27 | ctacagataaagttata | A | 129/b6/fvb/f1 | 92 |
|    | ctacagatgaagttata | B | f1 | 93 |
|    | tagacctgctgctatct | C | Cast-129 | 94 |
|    | tagacctgttgctatct | D | Spre | 95 |
| 28 | tgttgttctggcctcca | A | 129/F1 | 96 |
|    | tgttgttttggcctcca | B | B6 | 97 |
|    | ttctgagaatttgttag | C | 129/B6 | 98 |
|    | ttctgagagtttgttag | D | F1/spre | 99 |
| 29 | caggaagcagtagctcc | A | 129 | 100 |
|    | caggaagccgtagctcc | B | B6/FVB/F1 | 101 |
|    | agagtcaggtaagttgc | C | Cast-129 | 102 |
|    | agagtcagataagttgc | D | Spre | 103 |
| 30 | agatttcaaaaagtttt | A | 129/b6 | 104 |
|    | agattccaaaaggtttt | B | f1 | 105 |
|    | agatttcaaaaagtttt | C | fvb | 106 |
|    | cctgagggagcaatca | D | Cast-129 | 107 |
|    | cctgagggaagcaatca | E | Spre | 108 |
| 31 | aaggtaagataactaag | A | 129.f1 | 109 |
|    | aaggtaaggtaactaag | B | b6/fvbn | 110 |
|    | ggactacacagagaaac | C | Cast-129 | 111 |
|    | ggactacatagagaaac | D | Spre | 112 |
| 32 | cccaggctacacgaggg | A | 129/fvb/f1 | 113 |
|    | cccaggctacatgaggg | B | b6 | 114 |
|    | cttaccagttgtgagac | C | 129 | 115 |
|    | cttaccacttgtgagac | D | Spre | 116 |
|    | cttaccagtcgtgagac | E | Cast | 117 |
| 33 | ctgccctcaggtcttta | A | 129 | 118 |
|    | ctgccctccggtcttta | B | b6/fvbn | 119 |
|    | gcaataaaattgtttta | C | Cast-129 | 120 |
|    | gcaatgagatcgtttta | D | Spre | 121 |
| 34 | tgttctgtggagacccc | A | 129/fvbn/f1/cast/spre | 122 |
|    | tgttctgtagagacccc | B | b6 | 123 |
| 35 | cacattgaatcaaagcc | A | 129/b6/fvbn/f1 | 124 |
|    | cacattgagtcaaagcc | B | f1 | 125 |
|    | ggactacccacccgttc | C | 129 | 126 |
|    | gcgactgc--acccattct | E | Spre | 127 |
|    | gcgactgccccc--attct | D | Cast | 128 |
| 36 | cctgggccagccaggaa | A | 129/b6/cast | 129 |
|    | cctgggcctgccaggaa | B | fvbn/f1/spre | 130 |
| 37 | ccccaggtaaccatctt | A | 129/f1 | 131 |
|    | ccccaggtgaccatctt | B | b6/fvbn/cast/spre | 132 |
|    | ttctgtatattagctga | C | Cast-129 | 133 |
|    | tttctatattaa--ctgac | D | Spre | 134 |
| 38 | ggacccggacggtcttc | A | 129/b6 | 135 |
|    | ggacccggtcggtcttc | B | bvb/f1 | 136 |
|    | gtccctaatgttagcat | C | Cast-129 | 137 |
|    | gtccccaatgtcagcat | D | Spre | 138 |
| 39 | acgggggggtggcgtta | A | 129/f1 | 139 |
|    | acggggggg-tggcgttaa | B | b6/fvbn/cast/spre | 140 |
|    | tagacagccagcgcgtcac | C | Cast | 141 |
|    | tagatagccagcgcatcac | D | Spre | 142 |
| 40 | gattcttcgtgttcctt | A | 129-b6-F1 | 143 |
|    | gattcttcatgttcctt | B | FVBN-Cast-Spre | 144 |
| 41 | tgtaaaaacttagaata | A | 129/b6/f1 | 145 |
|    | tgtaaaaatttagaata | B | fvbn/cast/spre | 146 |
| 42 | tgtgaaagcgctcccaa | A | 129/fvbn/f1/cast/spre | 147 |
|    | tgtgaaagtgctcccaa | B | b6 | 148 |
| 43 | caaaggctcagagaatc | A | 129/b6/f1 | 149 |
|    | caaaggcttagagaatc | B | fvbn | 150 |
|    | ttaattctctccaaaca | C | 129/b6/fvb/f1 | 151 |
|    | ttaaggctctccggaca | D | f1 | 152 |
| 44 | ctgccaccgtgcacaca | A | 129/b6 | 153 |
|    | ctgccaccatgcacaca | B | fvbn/f1 | 154 |
|    | ccaaatattctgattcc | C | 129-Spre | 155 |
|    | ccaaatattcttttttt | D | Cast | 156 |
| 45 | atgagctgaccctccct | A | 129/B6/F1 | 157 |
|    | atgagctgcccctccct | B | FVB | 158 |

| | | | | |
|---|---|---|---|---|
| | acactaggtaaaagctc | C | 129/B6/FVB/F1 | 159 |
| | acactaggcaaaagctc | D | F1 | 160 |
| | agacaccacgaccgagg | E | 129-Spre | 161 |
| | agacaccaagaccgagg | F | Cast | 162 |
| 46 | gcagcgtccggttaagt | A | 129/f1 | 163 |
| | gcagcgtctggttaagt | B | b6/fvbn/f1 | 164 |
| | cagatactacaaggatg | C | 129 | 165 |
| | tacagatac---aaggatgc | D | SPRE/Cast | 166 |
| 47 | tcagctagtgtatctgt | A | 129/FVB/F1 | 167 |
| | tcacctagtgtatttgt | B | B6/F1 | 168 |
| | tttttattttggatt | C | 129-Cast | 169 |
| | tttt-aattttggattt | D | Spre | 170 |
| 48 | gatattgttttcattta | A | 129/ | 171 |
| | gatattgtcttcattta | B | b6/fvbn/f1 | 172 |
| 49 | agacccggtgctggtgt | A | 129/b6 | 173 |
| | agacccggcgctggtgt | B | fvbn/f1/cast | 174 |
| 50 | cttctaagctttgtctt | A | 129/fvb/f1/cast/spre | 175 |
| | cttctaagttttgtctt | B | b6/f1 | 176 |
| 51 | agttggcaaccagcatg | A | 129/ | 177 |
| | agttggcatccagcatg | B | b6/fvbn/f1 | 178 |
| | ggtgaaatggtaattac | C | 129-Cast | 179 |
| | ggtgaaatagtaattac | D | Spre | 180 |
| 52 | acgggatataacgagtt | A | 129/FVB/F1 | 181 |
| | acgggatacaacgagtt | B | B6/cast/spre | 182 |
| | gggatacaacgagtttc | C | 129-Cast | 183 |
| | gggatacaccgagtttc | D | Spre | 184 |
| 53 | gtatcttgggtgtcctg | A | 129/FVB/F1 | 185 |
| | gtaacttgggtgttctg | B | B6/F1/spre | 186 |
| | gggtgtcctgccccatc | C | 129 | 187 |
| | gggtgttctgtttatc | D | Spre | 188 |
| 54 | tgtccagttgttttgca | A | 129 | 189 |
| | tgtccagtcgttttgca | B | B6/FVB/F1/spre | 190 |
| | aagacagccggaactct | C | 129... | 191 |
| | aagacagcaggaactct | D | Spre | 192 |
| 55 | tgataggaccaaagaga | A | 129/b6/f1 | 193 |
| | cgataggactaaagaga | B | fvbn/f1 | 194 |
| | tccaaagccagggccca | C | 129 | 195 |
| | tccaaattcagggccca | D | Spre | 196 |
| 56 | cctgggccagccagaag | A | 129/B6/cast | 197 |
| | cctgggcctgccagaag | B | FVB/F1/spre | 198 |
| 57 | gattctctgagccttg | A | 129/b6/f1 | 199 |
| | gattctctaagccttg | B | fvbn | 200 |
| | taccattttttagatga | C | 129... | 201 |
| | taccatttcttagatga | D | Spre | 202 |
| | ctggaagggcagtgaat | A | 129 | 203 |
| | tctgga-cgagggtgaat | B | B6/FVB | 204 |
| 59 | tagttgcagcacaaatg | A | 129/B6 | 205 |
| | tagttgtagcacaaatg | B | FVB/F1 | 206 |
| 60 | acactaccgcacagagc | A | 129/b6/fvbn/f1 | 207 |
| | acactaccacacagagc | B | f1 | 208 |
| | aataataagtaaataag | C | 129/ | 209 |
| | aataataaataaataag | D | cast | 210 |
| 61 | tggcagtagttgttcat | A | 129/b6 | 211 |
| | tggcagtaattgttcat | B | fvbn/f1 | 212 |
| | aggtatgacgtcataag | C | 129-cast | 213 |
| | aggtatgatgtcataag | D | Spre | 214 |
| 62 | gttgttgttgaagattt | A | 129/fvbn/f1 | 215 |
| | ttgttgttg---aagattta | B | b6/f1 | 216 |
| | gatagtacaggtgttgtca | C | 129... | 217 |
| | gatggtacaggtgtcgtca | D | Spre | 218 |
| 63 | aatataatgtaacagga | A | 129/F1 | 219 |
| | aatataatataacagga | B | B6/FVB/F1 | 220 |
| 64 | ttaaccatttatctgat | A | 129/FVB | 221 |
| | ttaaccatatatctgat | B | B6/F1 | 222 |
| 65 | agagcccagcaaagttc | A | 129/B6 | 223 |
| | agagcccaacaaagttc | B | FVB/F1 | 224 |
| | atcccgaaccggggaaaat | C | 129-b6 | 225 |
| | atcccaaaccgggggaaaat | D | cast-spre | 226 |
| 66 | atgacaccaccacaacc | A | 129 | 227 |
| | atgacaccgccacaacc | B | B6/FVB/F1 | 228 |
| 67 | aggcaaacagatataac | A | 129/FVB/F1 | 229 |
| | aggcaaacggatataac | B | B6/cast/spre | 230 |
| | tgtattcactaataaga | C | 129-Cast | 231 |
| | tgtattcattaataaga | D | Spre | 232 |
| 68 | ttggcgtatacttcata | A | 129/B6/F1 | 233 |
| | ttggcgtacacttcata | B | FVB | 234 |
| | ctcaccacgctccatct | C | 129 | 235 |
| | ctcaccaccctccatct | D | Cast-Spre | 236 |
| 69 | atatctaaa----ggcacag | A | 129/FVB | 237 |

-continued

|  | | | | |
|---|---|---|---|---|
|  | tatctacataaaggcac | B | B6/F1/cast/spre | 238 |
|  | gtgtctcctagtctccc | C | B6-Cast | 239 |
|  | gtgtctcccagtctccc | D | Spre | 240 |
| 70 | atgagctgaccctccct | A | 129/B6/F1 | 241 |
|  | atgagctgcccctccct | B | FVB/F1 | 242 |
|  | ggacaacatttaattgg | C | 129-Cast | 243 |
|  | ggacaacacttaattgg | D | Spre | 244 |
| 71 | gctttaaaattttttatt | A | 129 | 245 |
|  | gctttaaatttttttatt | B | B6/FVB/F1 | 246 |
|  | aaatttgttcctaaatg | C | 129 | 247 |
|  | aaatttgtacctaaatg | D | Cast-Spre | 248 |
| 72 | gtgttgttctggcctcc | A | 129/FVB/spre | 249 |
|  | gtgttgttttggcctcc | B | B6/F1 | 250 |
| 73 | tgaatgacaaaaagaca | A | 129/B6/FVB | 251 |
|  | tgaatgacgaaaaagaca | B | F1/cast | 252 |
| B2 | 5'Rev    ACTGAGCCATCTCWCCAG | | W = A + T | 253 |
| 101 | acttaacttaagctggc | A | 129/ | 254 |
|  | gtacttaa-----gctggcctg | B | b6/fvb/f1 | 255 |
| 102 | actctaatatcccacag | A | 129/fvbn/f1 | 256 |
|  | actctaatctcccacag | B | b6 | 257 |
|  | cggatcggctctagttc | C | 129/cast | 258 |
|  | cggatcagctctagttc | D | spre | 259 |
| 103 | tcaaaccaataaggagg | A | 129/b6/fvb/f1 | 260 |
|  | tcaaaccagtaaggagg | B | f1 | 261 |
| 104 | gtgtgtgtgtgggggggg | A | 129/f1 | 262 |
|  | gtgtgtgtg---gggggggt | B | b6/fvbn | 263 |
|  | cttaataataatttcat | C | 129/cast | 264 |
|  | cttaataacaatttcat | D | spre | 265 |
| 105 | gtgtctccatatgtgtg | A | 129/b6/f1 | 266 |
|  | gtgtctacacatgtgtg | B | fvbn | 267 |
| 106 | aactcatcatgatggtt | A | 129/ | 268 |
|  | aactcataatgatggtt | B | b6/fvbn/f1 | 269 |
|  | aactcatcacgatggtt | C | cast | 270 |
|  | atcactcatagcccaga | D | 129/ | 271 |
|  | atcacttatagcccaga | F | spre | 272 |
|  | atcactcatatcccaga | E | cast | 273 |
| 107 | catcttaccagcattga | A | 129/cast/spre | 274 |
|  | catcttactagcattga | B | b6/fvbn/f1 | 275 |
| 108 | agtcagccggctctggc | A | 129/b6/f1 | 276 |
|  | agtcagccagctctggc | B | fvbn/f1 | 277 |
|  | gggtaggagtgggatgag | C | 129/ | 278 |
|  | gggcaggagtgggggtgag | E | spre | 279 |
|  | gggtaggagtgggggtgag | D | cast | 280 |
| 109 | tcagtattgttcttctc | A | 129/f1/spre | 281 |
|  | tcagtatttttcttctc | B | b6/fvbn/f1/cast | 282 |
| 110 | agcagagactgagctcg | A | 129/ | 283 |
|  | agcagagaccgagctcg | B | b6/fvbn/f1 | 284 |
|  | acagggtcgattcgtc | c | 129/b6/fvbn/f1/cast | 285 |
|  | acaggggatcgattcgtc | E | spre | 286 |
|  | acagggtcgtttcgtc | D | f1 | 287 |
| 111 | tcccaaagcattcaagg | A | 129/b6/f1 | 288 |
|  | tcccaaagtattcaagg | B | fvbn/f1 | 289 |
|  | gaccagggttaatgact | C | 129/b6 | 290 |
|  | gaccagggctaatgact | D | cast/spre | 291 |
| 112 | ctattaacagagtcgag | A | 129/b6/f1 | 292 |
|  | ctattaacggagtcgag | B | fvbn | 293 |
|  | gtgatactggatgtctg | C | 129/b6 | 294 |
|  | gtgataccg-atgtctgg | D | cast/spre | 295 |
| 113 | ctctctcgatagtctaa | A | 129/f1 | 296 |
|  | ctctctcgctagtctaa | B | b6/fvbn/f1/cast | 297 |
|  | tctctcgatagtctaat | C | 129/ | 298 |
|  | tctctcgctggtctaat | D | cast | 299 |
| 114 | agatgcaaaattcttag | A | 129/ | 300 |
|  | agatgcacagttcttag | B | b6/fvbn/f1 | 301 |
| 115 | ggaaaatgctcaggtag | A | 129/f1/cast/spre | 302 |
|  | ggaaaatgttcaggtag | B | b6/fvbn | 303 |
| 116 | tctgggcagagtgcagg | A | 129/ | 304 |
|  | tctgggcagcgtgcagg | B | b6/fvb/f1 | 305 |
| 117 | tatggaacggttgcttc | A | 129/fvb | 306 |
|  | tatggaactgttgcttc | B | b6/f1 | 307 |
|  | aagcctggtacccgctg | C | 129/cast | 308 |
|  | aagcctggcacccgctg | D | spre | 309 |
| 118 | cattcttcttttctga | A | 129/ | 310 |
|  | cattcttcgttttctga | B | b6/fvbn/f1/cast/spre | 311 |
|  | ctgcaggcttgtctgtg | C | 129/CAST | 312 |
|  | ctgcaggtttgtctgtg | D | spre | 313 |
| 119 | tgccatttcctataaca | A | 129/f1 | 314 |
|  | tgccatttgctataaca | B | b6/fvbn | 315 |
| 120 | ccgccacacccgctcct | A | 129/b6 | 316 |

-continued

| | | | | |
|---|---|---|---|---|
| | ccgccacagccgctcct | B | fvbn/f1 | 317 |
| 121 | caaataatgctagttat | A | 129/b6/f1 | 318 |
| | caaataatgttagttat | B | fvbn | 319 |
| 122 | ggatgttgacacgctac | A | 129/fvbn/f1 | 320 |
| | ggatgttgtcacgctac | B | b6/f1 | 321 |
| | catgtgtc-caacgccat | C | 129/ | 322 |
| | catgtgtcacaacgcca | D | cast/spre | 323 |
| 123 | aaaggggcctaaagga | A | 129/fvbn/f1 | 324 |
| | aaaggggctttaaagga | B | b6 | 325 |
| | tgaaaagttcttttcat | C | 129/cast | 326 |
| | tgaaaagtacttttcat | D | spre | 327 |
| 124 | cctctctatgtgtgagc | A | 129/b6/f1 | 328 |
| | cctctctacgtgtgagc | B | fvbn | 329 |
| | gaagttttaggagattct-t | C | 129/ | 330 |
| | gaagatttaggagagtctc | D | spre | 331 |
| 125 | agggatgtattttgtta | A | 129/fvbn/f1 | 332 |
| | agggatgtgttttgtta | B | b6 | 333 |
| | acaattcaaatgtatat | C | 129/cast | 334 |
| | acaattcatatgtatat | D | spre | 335 |
| 126 | cttgcctaacctgcaca | A | 129/b6/f1 | 336 |
| | cttgcctagcctgcaca | B | fvbn | 337 |
| | caacagc---acctcatatc | C | 129/bt/cast | 338 |
| | acagcggtgcctcgtat | D | spre | 339 |
| 127 | actcacagtgtcagggc | A | 129/fvbn/f1/spre | 340 |
| | actcacagcgtcagggc | B | b6/cast | 341 |
| 128 | ggctgctcctgtgtctg | A | 129/fvbn/f1/cast | 342 |
| | ggctcttcctgtgtctg | B | b6 | 343 |
| | ggctgctcctgtgtttctg | C | spre | 344 |
| 129 | aagatgcccttctga | A | 129/f1 | 345 |
| | aatagatgccctcttga | B | b6/fvbn | 346 |
| | aatcgatgcccttctga | c | spre | 347 |
| 130 | ttggtctagcaggtagc | A | 129/fvbn/f1 | 348 |
| | ttggtctaccaggtagc | B | b6 | 349 |
| | agccttggctcttaaaa | C | 129/cast | 350 |
| | agccttggttcttaaaa | D | spre | 351 |
| 131 | agtctctggcgcctttg | A | 129/fvbn/f1/cast/spre | 352 |
| | agtctctgccgcctttg | B | b6 | 353 |
| 132 | tagcaggaggcacagctta | A | 129/ | 354 |
| | aagcaggaggcacaactta | B | b6 | 355 |
| | aagcaggaggcacagctta | C | fvb/f1/CAST | 356 |
| | tagcaggaggcacagcttg | D | spre | 357 |
| 133 | aggagagaccggactcc | A | 129/fvb/f1 | 358 |
| | aggagagagcggactcc | B | b6 | 359 |
| 134 | tacaagtcatccttcct | A | 129/b6/f1 | 360 |
| | tacaagtcgtccttcct | B | fvbn/f1 | 361 |
| | atacctccctcagacaa | C | 129/cast | 362 |
| | atacctcc-tcagacaag | D | spre | 363 |
| 135 | aaacaaacaaacaaacc | A | 129/b6/f1/cast/spre | 364 |
| | aaacaaaccaacaaacc | B | fvbn | 365 |
| | gtgcgccaccatgacca | C | 129/cast | 366 |
| | gtgcgccatcatgacca | D | spre | 367 |
| 136 | ggctttcccattagtgg | A | 129/ | 368 |
| | ggctttcctattagtgg | B | b6/fvbn/f1 | 369 |
| | ccctcacctctctctca | C | 129/cast | 370 |
| | cctcaccctctctctca | D | spre | 371 |
| 137 | aatctctcgcgttcatt | A | 129/fvbn/f1 | 372 |
| | aatctctcacgttcatt | B | b6 | 373 |
| 138 | aatgataccgatcctta | A | 129/f1 | 374 |
| | aatgatacagatcctta | B | b6/fvbn | 375 |
| | ataaaactgcaattcgtg | C | 129/b6 | 376 |
| | ataaaactacattcgtg | D | cast/spre | 377 |
| B1 Musch | AGTTCCAGGACAGCCAGG | | | 378 |
| 201 | atatctccgactttgaa | A | 129/cast | 379 |
| | atatctccaactttgaa | B | b6/fvb/f1/spre | 380 |
| | tggccctgcagagtctg | C | 129-Cast | 381 |
| | tggctctgcagag-ctgg | D | Spre | 382 |
| 202 | caatggatc---aaagatgc | A | 129-FVB-F1 | 383 |
| | atggatcaacaaagatg | B | B6 | 384 |
| | gctgcctc---aaggtataa | C | 129/b6 | 385 |
| | ctgcctcttaaggtata | D | cast/spre | 386 |
| 203 | acctatggctcctcatc | A | 129/b6/f1 | 387 |
| | acctatggttcctcatc | B | fvb | 388 |
| | tcttctccctgcttta | C | 129-Cast | 389 |
| | tcttctcac-tgctttag | D | Spre | 390 |
| 204 | ccgc-ataaaaagctgag | A | FVB-F1 | 391 |
| | ccgccataaaa-gctgag | B | B6-F1 | 392 |
| | agaatataggggttttt | C | 129/cast | 393 |
| | agaatacag--ttttttt | D | spre | 394 |

| | | | | |
|---|---|---|---|---|
| 205 | agagttgctgtgcaggg | A | 129/b6/f1 | 395 |
| | agagttgccgtgcaggg | B | fvb/cast | 396 |
| | agagttgcagtgcaggg | C | spre | 397 |
| 206 | taagcagtgttcttggc | A | 129-B6-F1 | 398 |
| | taagcagtattcttggc | B | FVBN | 399 |
| | ttctcccctgcttta | C | 129/Cast | 400 |
| | tcttctcac-tgctttag | D | spre | 401 |
| 207 | tttttttattattga | A | 129/fvb/f1 | 402 |
| | ttttttt-attattgaa | B | b6 | 403 |
| | tgtggtacgcacatctg | C | 129-Cast | 404 |
| | tgtggtacacacatctg | D | Spre | 405 |
| 208 | agactcttagacttctg | A | 129/f1 | 406 |
| | agactcttaggcttctg | B | b6/fvb/f1 | 407 |
| | agactcataagcttctg | C | spre | 408 |
| | agactcttaggcttctg | D | cast | 419 |
| 209 | cacgtacccgaacgtga | A | 129-B6 | 410 |
| | cacgtacctgaacgtga | B | FVB-F1 | 411 |
| | attacggtttgtcgtca | C | 129/CAST | 412 |
| | attacggttggtcgtca | D | spre | 413 |
| 210 | ccaagatacgaaaccag | A | 129/f1/cast/spre | 414 |
| | ccaagatatgaaaccag | B | b6 | 415 |
| 211 | tgcaatgaccagcaacc | A | 29/b6 | 416 |
| | tgcaacgaccagcaacc | B | fvb/f1/cast | 417 |
| | tgtaacgaccaacaact | C | spre | 418 |
| 212 | tctaaagggaaagatgg | A | 129-FVB | 419 |
| | tctaaagg-aaagatgga | B | B6-F1 | 420 |
| 213 | ctggactcatacataca | A | 129-FVB-F1 | 421 |
| | ctggactcgtacataca | B | B6-F1-Cast/SPRE | 422 |
| | agtttggtcccctggac | C | 129/FVB/B6-F1-Cast | 423 |
| | agtttggtttcctggac | D | Spre | 424 |
| 214 | tatagcttcatgtaaaa | A | 129/fvb/f1/cast/spre | 425 |
| | tatagctttatgtaaaa | B | b6 | 426 |
| 215 | tttttt-attattgaa | A | 129 | 427 |
| | tttttttttattattga | B | B6-FVB-F1 | 428 |
| | actcattgccaatttaa | C | 129 | 429 |
| | actcattcagaatttaa | D | spre/CAST | 430 |
| 216 | atgcgtaatgggggcta | A | 129 | 431 |
| | atgcgtaacgggggcta | B | b6/fvb/f1/cast/SPRE | 432 |
| | attaattgctcttttaaa | C | 129/b6/fvb/f1/cast | 433 |
| | gtaattgctcttttaaa | D | spre | 434 |
| 217 | tctgattagtgatggat | A | 129-F1 | 435 |
| | tctgatta-tgatggatt | B | B6 | 436 |
| | agcagagtgtctcgtaa | C | 129 | 437 |
| | agcagagtatctcgtaa | D | spre/CAST | 438 |
| 218 | gctggcagatatcggta | A | 129/b6/f1 | 439 |
| | gctggcaggtatcggta | B | fvb/cast | 440 |
| 219 | aactgcaatgaccagca | A | 129-B6 | 441 |
| | aactgcaacgaccagca | B | FVB-F1 | 442 |
| | gctggtcattgcagttt | C | 129 | 443 |
| | gttggtcgttacagttt | D | spre | 444 |
| | gctggtcgttgcagttt | F | cast | 445 |
| 220 | gctggcagatatcggta | A | 129-B6-F1 | 446 |
| | gctggcaggtatcggta | B | FVB | 447 |
| | atagaaagtccaccgtc | C | 129/cast | 448 |
| | atagaaagcccaccgtc | D | spre | 449 |
| 221 | ttagtgaccgtgtaaac | A | 129/b6/f1 | 450 |
| | ttagtgactgtgtaaac | B | fvb | 451 |
| | ggggaggagctttgttc | C | 129-Cast | 452 |
| | ggggaggatctttgttc | D | Spre | 453 |
| 222 | ggcctggacacaaaagc | A | 129/fvb/f1 | 454 |
| | ggcctggaaacaaaagc | B | b6 | 455 |
| | ccctttttctagtattgt | C | 29 | 456 |
| | ccctttttccagtattgt | D | Cast-Spre | 457 |
| 223 | gaattggttttaggaat | A | 129-F1-Cast-Spre | 458 |
| | gaattggtattaggaat | B | B6 | 459 |
| 224 | acccagctttccatggt | A | 129/f1 | 460 |
| | acccagctctccatggt | B | b6/fvb/CAST | 461 |
| 225 | tcacgttcgggtacgtg | A | 129/b6/f1 | 462 |
| | tcacgttcaggtacgtg | B | fvb/f1 | 463 |
| | tgccttccggttggcaa | C | 129-Cast | 464 |
| | tgccttccagttggcaa | D | Spre | 465 |
| 226 | ttttatcatacaattgc | A | 129-F1 | 466 |
| | ttttatcagacaattgc | B | B6-FVB-F1 | 467 |
| 227 | atcttctcttctttgag | A | 129/f1 | 468 |
| | atcttctcctcctttgag | B | b6/fvb | 469 |
| | cagtcctctgctttctc | C | 129-Cast | 470 |
| | cagtcctcagctttctc | D | Spre | 471 |
| 228 | ccaagatacgaaaccag | A | 129/f1/spre | 472 |
| | ccaagatatgaaaccag | B | b6 | 473 |

-continued

| | | | | |
|---|---|---|---|---|
| 229 | ggtattcaagggttact | A | 129/cast/spre | 474 |
| | ggtattca-ggttactg | B | b6/fvb 1bp del | 475 |
| 230 | acctatggctcctcatc | A | 129/b6/f1/cast | 476 |
| | acctatggttcctcatc | B | fvb | 477 |
| 231 | ttttatcatacaattgc | A | 129/f1 | 478 |
| | ttttatcagacaattgc | B | b6/fvb | 479 |
| 232 | aaccagggcttaagtct | A | 129 | 480 |
| | aaccagggattaagtct | B | b6/fvb/f1 | 481 |
| | cagaaaaacagatatac | C | 129-B6-FVB-F1 | 482 |
| | cagaaaagagatatac | D | Spre | 483 |
| 234 | tctgagcgtgagtgctg | A | 129/fvb | 484 |
| | tctgagcgcgagtgctg | B | b6/f1/cast/spre | 485 |
| | acctcagaagcggaggt | C | 129-B6-FVB-F1 | 486 |
| | acctcggaaggggaggt | D | Spre | 487 |
| | acctcggaagcggaggt | E | Cast | 488 |
| 235 | taactcgatcgctatca | A | 129-B6-F1 | 489 |
| | taactcgcttgctatca | B | FVBN-Cast | 490 |
| | taactcgctcgctatca | C | Spre | 491 |
| 236 | gaatttctcaacttctt | A | 129/fvb/f1/spre | 492 |
| | gaatttctgaacttctt | B | b6/f1 | 493 |
| 237 | cagggtccccaatttg | A | 129/f1/SPRE | 494 |
| | cagggtctccaatttg | B | b6/fvb | 495 |
| 238 | ttttgctgtgc-aggcta | A | 129-B6-F1 | 496 |
| | ttttactgtgccaggct | B | FVB | 497 |
| | gacagccctgtctcaaa | C | 129/cast | 498 |
| | agagaaaccctgtctca | D | spre | 499 |
| 239 | gcaccggtctgagcagt | A | 129/f1 | 500 |
| | gcaccggtttgagcagt | B | b6/fvb/f1 | 501 |
| | ccgtgcccctgaacaat | C | 129-B6-FVB-F1-Cast | 502 |
| | ccgtgcccttgaacaat | D | Spre | 503 |
| 240 | tcacgttcgggtacgtg | A | 129/b6/f1 | 504 |
| | tcacgttcaggtacgtg | B | fvb/f1 | 505 |
| | tgattcgctgggactct | C | 129-Cast | 506 |
| | tgattcgccgggactct | D | Spre | 507 |
| 241 | ttgatatccgaggcctt | A | 129/b6/fvb/f1 | 508 |
| | ttgatatctgaggcctt | B | f1/CAST/SPRE | 509 |
| 242 | tccctgggccaagcata | A | 129/b6/fvb | 510 |
| | tccctgggtcaagcata | B | f1 | 511 |
| 243 | ttatggctgaggatcac | A | 129-B6-F1-Cast | 512 |
| | ttatggctgcggatcat | B | FVB | 513 |
| | ttatggcagggatcac | C | Spre | 514 |
| 244 | ctctctgcgctgaagca | A | 129/b6 | 515 |
| | ctctctgctctgaagca | B | fvb/f1 | 516 |
| | agatacagagatgtgtt | C | 129-B6-FVB-F1 | 517 |
| | agatactgaggtgtgtt | D | Spre | 518 |
| 245 | cgacatctggcagatgt | A | 129/f1 | 519 |
| | cgacatctagcagatgt | B | b6/fvb | 520 |
| | gtcacaaatagtatttc | C | 129/cast | 521 |
| | gtcacaaagagtatttc | D | Spre | 522 |
| 246 | aaggtgtgtgcgtgtgt | A | 29/f1 | 523 |
| | aaggtgtgcgcgtgtgt | B | fvb | 524 |
| 247 | agtctttttttcctga | A | 129-B6-FVB | 525 |
| | tagtc-tttttttt-cctgaa | B | F1 | 526 |
| 248 | caggctgtgggaggctt | A | 129/b6/f1 | 527 |
| | caggctgcggaaggctt | B | fvb | 528 |
| | ctgtaagtcattcaata | C | 129-B6-FVB-F1-Cast | 529 |
| | ctgtaagtaattcaata | D | Spre | 530 |
| 249 | cagggtccccaatttg | A | 129/f1 | 531 |
| | cagggtctccaatttg | B | b6/fvb | 532 |
| 250 | gactcatggccgccttg | A | 129 | 533 |
| | gactcattgccgccttgg | B | B6-FVB-F1 | 534 |
| | gactcctggccgcctgg | C | F1 | 535 |
| | gactcctggctgcctgg | D | Spre | 536 |
| | gactcctggccgcctgg | E | Cast | 537 |
| 251 | acaggga-ggaaggaag | A | 129 | 538 |
| | acaggggaaggaaggaa | B | b6/fvb/f1 | 539 |
| 252 | ttgatatagattgattc | A | 129/b6/f1 | 540 |
| | ttgatatatattgattc | B | fvb/f1 | 541 |
| | atagaacagcaaagtaa | C | 129-B6-FVB-F1-Cast | 542 |
| | atagaacaacaaagtaa | D | Spre | 543 |
| 253 | aacaagcatctatggat | A | 129/fvb/f1 | 544 |
| | aacaagcacctatggat | B | b6 | 545 |
| DOP | | | | |
| 300 | gagcaggttaagcgatg | A | 129/ | 546 |
| | gagcaggtgaagcgatg | B | B6 | 547 |
| 301 | ggcttccagcttgattc | A | 129/ | 548 |
| | ggcttccaacttgattc | B | B6 | 549 |
| 302 | agatagggatgaatccc | A | 129/ | 550 |
| | agataggggtgaatccc | B | B6 | 551 |

-continued

| | | | | | |
|---|---|---|---|---|---|
| 303 | tcattcaccgtttattg | A | 129/ | | 552 |
| | tcattcactgtttattg | B | B6 | | 553 |
| 304 | ctgacatactgcttagg | A | 129/ | | 554 |
| | ctgacatattgcttagg | B | B6 | | 555 |
| 305 | ctaggaaagcctaaatt | A | 129/ | | 556 |
| | ctaggaaaacctaaatt | B | B6 | | 557 |
| 306 | atgtcaggattttaaga | A | 129/ | | 558 |
| | atgtcagggttttaaga | B | B6 | | 559 |
| 307 | ggtttccaattggaaag | A | 129/ | | 560 |
| | ggtttccagtggaaag | B | B6 | | 561 |
| 308 | cgaggagtgcaaagcga | A | 129/ | | 562 |
| | cgaggagtccaaagcga | B | B6 | | 563 |
| 309 | tgtgtgtgtgtctgtct | A | 129/ | | 564 |
| | tgtgtgtgcgtctgtct | B | B6 | | 565 |
| 310 | gcaagatgcagctgcat | A | 129/ | | 566 |
| | gcaagatgtagctgcat | B | B6 | | 567 |
| 311 | gctgggctattctgta | A | 129/ | | 568 |
| | gctgggccattctgta | B | B6 | | 569 |
| 312 | caataacggacctgcct | A | 129/ | | 570 |
| | caataacgaacctgcct | B | B6 | | 571 |
| 313 | tagcctctctacatagg | A | 129/ | | 572 |
| | tagcctctgtacatagg | B | B6 | | 573 |

| ASO name | ASO sequence | 12-01 | 104-01 | 884-01 | 1331-01 | |
|---|---|---|---|---|---|---|
| 3A-G | CATCTATAGGTTCACTT | GT | TT | TT | TT | 574 |
| 3A-T | CATCTATATGTTCACTT | | | | | 575 |
| 5A-C | GCCAACAACATTGAGAG | GG | CG | GG | GG | 576 |
| 5A-G | GCCAACAAGATTGAGAG | | | | | 577 |
| 7A-C | GGGTCGTGCGTCCCCCT | TT | CT | TT | TT | 578 |
| 7A-T | GGGTCGTGTGTCCCCCT | | | | | 579 |
| 9A-A | ATTGTCTCACATTTCTT | AA | GG | AA | AA | 580 |
| 9A-G | CATTGTCTCGCATTTCTT | | | | | 581 |
| 12A-C | DGGTGTGGTCGCAGAAGG | CC | CC | CT | CT | 582 |
| 12A-T | AGGTGTGGTTGCAGAAGG | | | | | 583 |
| 15A-A | TCATTGCCACACTTGAA | AA | GG | AA | GG | 584 |
| 15A-G | ArCATTGCCGCACTTGAA | | | | | 585 |
| 20A-A | ATCTGTCTACAATGATC | AG | GG | AA | AG | 586 |
| 20A-G | ATCTGTCTGCAATGATC | | | | | 587 |
| 22A-A | BGGCTGGGCACAGTGGCT | AA | GG | AA | AA | 588 |
| 22A-G | GGCTGGGCGCAGTGGCT | | | | | 589 |
| 34A-A | CAGCCTGGAGAACAAGT | CC | CC | CC | AC | 590 |
| 34A-C | CAGCCTGGCGAACAAGT | | | | | 591 |
| 39A-C | TTTGACACCCGGAAGCT | CT | CC | CC | CC | 592 |
| 39A-T | TTTGACACTCGGAAGCT | | | | | 593 |
| 40A-C | CTGCCTTTCATACTGCC | CT | TT | CT | TT | 594 |
| 40A-T | CTGCCTTTTATACTGCC | | | | | 595 |
| 40B-C | ACAATAGACGTTCCCCG | TT | CT | TT | CT | 596 |
| 40B-T | ACAATAGATGTTCCCCG | | | | | 597 |
| 41A-A | GGTGTTTGATTTGTACT | CC | AC | CC | CC | 598 |
| 41A-C | GGTGTTTGCTTTGTACT | | | | | 599 |
| 42A-A | TCCAACTCAAAAAATGT | AT | AA | AT | AT | 600 |
| 42A-T | TCCAACTCTAAAAATGT | | | | | 601 |
| 44A-C | GGGCCGCTCACAGTCCA | CC | CT | CC | CC | 602 |
| 44A-T | GGGCCGCTTACAGTCCA | | | | | 603 |
| 44B-C | GCATGGCTCGTGGGTTT | CT | CT | TT | CT | 604 |
| 44B-T | GCATGGCTTGTGGGTTT | | | | | 605 |
| 46A-G | GTTGGGAAGTGGAGCGG | GG | TT | GG | TT | 606 |
| 46A-T | GTTGGGAATTGGAGCGG | | | | | 607 |
| 50A-A | AAGGGATGAGGATGTGA | AG | AA | AA | AG | 608 |
| 50A-G | AAGGGATGGGGATGTGA | | | | | 609 |
| 50B-A | TCCTCGAGAGCTTTGCT | AG | AG | AA | AG | 610 |
| 50B-G | TCCTCGAGGGCTTTGCT | | | | | 611 |
| 51A-C | TGACAATGCGTGCCCAA | CT | CC | CC | CC | 612 |
| 51A-T | TGACAATGTGTGCCCAA | | | | | 613 |
| 53A-A | TCCATGTCATAGATTTC | AG | AA | AA | AA | 614 |
| 53A-G | TCCATGTCGTAGATTTC | | | | | 615 |
| 66A-A | TGGAGGACAGTGGAGGG | TT | TT | TT | AT | 616 |
| 66A-T | TGGAGGACTGTGGAGGG | | | | | 617 |
| 69A-C | ACCCATTTCCTGAAAAT | TT | CT | TT | TT | 618 |
| 69A-T | ACCCATTTTCTGAAAAT | | | | | 619 |
| 71A-G | CTGAGTTCGGCACTGCT | TT | GG | GG | TT | 620 |
| 71A-T | CTGAGTTCTGCACTGCT | | | | | 621 |
| 71B-G | ACCAGTTTGGCTCAAAG | GG | TT | TT | GG | 622 |
| 71B-T | ACCAGTTTTGCTCAAAG | | | | | 623 |
| 72A-A | CCAATCAGAACGTGCAG | AA | GG | GG | AA | 624 |
| 72A-G | CCAATCAGAGCGTGCAG | | | | | 625 |
| 73A-A | ACCCACACAGACACTGC | AA | AT | TT | AT | 626 |
| 73A-T | ACCCACACTGACACTGC | | | | | 627 |

-continued

| | | | | | | |
|---|---|---|---|---|---|---|
| 81A-C | GGACAAAGCGCTGGTGT | TT | CT | CC | CT | 628 |
| 81A-T | GGACAAAGTGCTGGTGT | | | | | 629 |
| 81C-C | AGCTGGTCCCCCTMCCC | TT | CT | CC | CC | 630 |
| 81C-T | AGCTGGTCTCCCTMCCC | | | | | 631 |
| 90A-A | GGTGTAGTAAGCACAGC | AA | AA | AC | AA | 632 |
| 90A-C | GGTGTAGTCAGCACAGC | | | | | 633 |
| 91A-C | AGCGAACACGGGGGAAA | CC | CC | TT | CC | 634 |
| 91A-T | AGCGAACATGGGGGAAA | | | | | 635 |
| 98D-A | GTGACAGCACCAAACTT | GG | AG | GG | GG | 636 |
| 98D-G | GTGACAGCGCCAAACTT | | | | | 637 |
| 101A-C | GTCTGTTGCTGTTATTT | TT | TT | TT | CT | 638 |
| 101A-T | GTCTGTTGTTGTTATTT | | | | | 639 |
| 111A-A | ACCAGCATAGCCCAGAG | GG | GG | GG | AG | 640 |
| 111A-G | ACCAGCATGGCCCAGAG | | | | | 641 |
| 111B-A | CGTAGGAGACAAGACCT | GG | GG | GG | AG | 642 |
| 111B-G | CGTAGGAGGCAAGACCT | | | | | 643 |
| 117A-A | CTCTGCTGAATCTCCCA | | GG | GG | AG | 644 |
| 117A-G | CTCTGCTGGATCTCCCA | | | | | 645 |
| 124A-A | AAGCAAAGACTGATTCA | TT | AT | TT | TT | 646 |
| 124A-T | AAGCAAAGTCTGATTCA | | | | | 647 |
| 125A-A | AGGCAGCTAGAGGGAGA | CC | AA | AC | AA | 648 |
| 125A-C | AGGCAGCTCGAGGGAGA | | | | | 649 |
| 130C-C | TTCCATTCCGTTCAATT | TT | TT | TT | CC | 650 |
| 130C-T | TTCCATTCTGTTCAATT | | | | | 651 |
| 130D-C | TATTGTTACTGATTTTG | CT | CT | CT | TT | 652 |
| 130D-T | TATTGTTATTGATTTTG | | | | | 653 |
| 136A-A | GAGCTTTCAGAGGCTGA | AA | AG | AG | AG | 654 |
| 136A-G | GAGCTTTCGGAGGCTGA | | | | | 655 |
| 137A-A | GGGGGAAGATATGGAGT | GG | AG | AA | AG | 656 |
| 137A-G | GGGGGAAGGTATGGAGT | | | | | 657 |
| 143A-C | CATGGCCTCGTGGGTTT | TC | TC | TT | TC | 658 |
| 143A-T | CATGGCCTTGTGGGTTT | | | | | 659 |
| 147B-A | GGGKAGGGAGACCAGCT | AA | AG | GG | GG | 660 |
| 147B-G | GGGKAGGGGGACCAGCT | | | | | 661 |
| 147C-A | GCAGTGTCAGTGTGGGT | TT | AT | AA | AT | 662 |
| 147C-T | GCAGTGTCTGTGTGGGT | | | | | 663 |
| 147D-A | ACACCAGCACTTTGATC | AA | AG | GG | AG | 664 |
| 147D-G | ACACCAGCGCTTTGATC | | | | | 665 |
| 151A-A | CCTTCTGCAACCACACC | GG | GG | AG | AG | 666 |
| 151A-G | CCTTCTGCGACCACACC | | | | | 667 |
| 163A-A | AAATTCGCAGGAGCCGA | GG | AG | GG | GG | 668 |
| 163A-G | AAATTCGCGGGAGCCGA | | | | | 669 |
| 164B-A | AGGTCTAGACGCTCACC | AG | GG | AG | GG | 670 |
| 164B-G | AGGTCTAGGCGCTCACC | | | | | 671 |
| 164C-A | GGAGGAACACTTCAAAC | GG | AG | GG | GG | 672 |
| 164C-G | GGAGGAACGCTTCAAAC | | | | | 673 |
| 170A-A | TTTGTGCTATACCTTGA | AA | AG | AG | AG | 674 |
| 170A-G | TTTGTGCTGTACCTTGA | | | | | 675 |
| 179A-C | ATGATGCACACACCCTG | CT | CC | TT | CC | 676 |
| 179A-T | ATGATGCATACACCCTG | | | | | 677 |
| 181B-C | TATTGCTCCGCCTCCTC | CT | TT | CC | TT | 678 |
| 181B-T | TATTGCTCTGCCTCCTC | | | | | 679 |
| 181D-C | CTCAGAGACTGTGTGCC | CG | CC | CC | CC | 680 |
| 181D-G | CTCAGAGAGTGTGTGCC | | | | | 681 |
| 187A-C | ATCTTCTGCGTCACTCA | CT | CT | CC | CC | 682 |
| 187A-T | ATCTTCTGTGTCACTCA | | | | | 683 |
| 187B-A | CAGCATCTAGTAACCAC | AG | AA | GG | AG | 684 |
| 187B-G | CAGCATCTGGTAACCAC | | | | | 685 |
| 190A-C | ATTAGTGCCAAATACAT | CC | CC | CT | CT | 686 |
| 190A-T | ATTAGTGCTAAATACAT | | | | | 687 |
| 195B-A | TGCTCCACAGCAGCCGT | AT | TT | TT | TT | 688 |
| 195B-T | TGCTCCACTGCAGCCGT | | | | | 689 |
| 196A-A | TAGGGGAGAATCTGTTT | CC | AC | AC | AA | 690 |
| 196A-C | TAGGGGAGCATCTGTTT | | | | | 691 |

The invention also encompasses a composition comprising a plurality of RCGs immobilized on a surface, wherein the RCGs are composed of a plurality of DNA fragments, each DNA fragment including a $(N)_x$-TARGET polynucleotide structure as described above, i.e., wherein the TARGET portion is identical in all of the DNA fragments of each RCG, the portion includes at least 7 nucleotide residues, wherein x is an integer from 0 to 9, and wherein each N is any nucleotide residue. Preferably the TARGET portion includes at least 8 nucleotides residues.

In other aspects, the invention includes a method for performing DOP-PCR. The prior art DOP-PCR technique was originally developed to amplify the entire genome in cases where DNA was in short supply. This method is accomplished using a primer set wherein each primer has an arbitrarily selected six nucleotide residue portion, at its 3' end. The complexity of the resultant product is extremely high due to the short length and results in amplification of the genome. By increasing the length of the arbitrarily selected of the DOP-PCR primer from 6 nucleotides to 7, and preferably 8, or more nucleotide residues the complexity of the genome is significantly reduced.

EXAMPLE

Example 1

Identification and Isolation of SNPs

High allele frequency SNPs are estimated to occur in the human genome once every kilobase or less (Cooper et al., 1985). A method for identifying these SNPs is illustrated in FIG. 1. As shown in FIG. 1, inter-Alu PCR was performed on genomes isolated from three unrelated individuals. The PCR products were cloned, and a mini library was made for each of the 3 individuals. The library clone inserts were PCR-amplified and spotted on nylon filters. Clones were matched by hybridization into two sets of identical clones from each individual, for a total of 6 clones per matched clone set. These sets of clones were sequenced, and the sequences were compared in order to identify SNPs. This method of identifying SNPs has several advantages over the prior art PCR amplification methods. For instance, a higher quality sequence is obtained from cloned DNA than is obtained from cycle sequencing of PCR products. Additionally, every sequence represents a specific allele, rather than potentially representing a heterozygote. Finally, sequencing ambiguities, Taq polymerase errors, and other source of sequence error particular to one representation of the sequence are reduced by application of an algorithm which requires that the same variant sequence be present in at least 2 of the 6 clones sampled.

In general, the Alu PCR method for identifying SNPs can be performed using genomic DNA obtained from independent individuals, unrelated or related. Briefly, Alu PCR is performed which yields a product having an estimated complexity of approximately 100 different single copy genomic DNA sequences and an average sequence length of between about 500 base pairs and 1 kilobase pairs. The PCR products are cloned, and a mini library is made for each individual. Approximately 800 clones are selected from each library and transferred into a 96-well dish. Filter replicas of each plate are hybridized with PCR probes from individual clones selected from one of the libraries in order to create a matched clone set of 6 clones, 2 from each individual. Many sets of clones can be isolated from these libraries. The clones can be sequenced and compared to identify SNPs.

Methods

An Alu primer designated primer 8C was designed to produce an Alu PCR product having a complexity of approximately 100 independent products. Primer 8C (having the nucleotide sequence CTT GCA GTG AGC CGA GATC; SEQ ID NO: 3) is complementary with base pairs 218–237 of the Alu consensus sequence (Britten et al., 1994). In order to reduce the complexity of the product, however, the last base pair of the primer was selected to correspond to base pair 237 of the consensus sequence, a nucleotide which has been shown to be highly variable among Alu sequences. Primer 8C therefore produces a product having complexity lower than that produced using Alu primers which match a segment of the Alu sequence in which there is little variation in nucleotide sequence among Alu family members.

Preliminary experiments were conducted to estimate the complexity of the product produced by Alu PCR reaction with primer 8C on the CEPH Mega Yacs. These preliminary experiments confirmed that primer 8C produced a lower number of Alu PCR products than other Alu PCR primers closely matching less variable sequences in the Alu consensus.

Three libraries of Alu PCR products were produced from inter-Alu PCR reactions involving genomic DNA derived from three unrelated CEPH individuals designated 201, 1701, and 2301. The reactions were performed at an annealing temperature of 58° C. for 32 cycles using the 8C Alu primer. Each set of PCR reaction products was purified by phenol:chloroform extraction followed by ethanol precipitation. The products were shotgun cloned into the T-vector pCR2.1 (Invitrogen); electroporated into *E. coli* strain DH10B Electromax ampicillin-containing LB agar plates. 768 colonies were picked from each of the three libraries into eight 96-well format plates containing LB+ampicillin and grown overnight. The following day, an equal volume of glycerol was added and the plates were stored at −80° C. An initial survey of the picked clones indicated an average insert size of between 500 base pairs and 1 kilobase pair.

To identify matching clones in each library, 1 microliter of an overnight culture made from each library plate well was subjected to PCR amplification using vector-derived primers. Amplified inserts were spotted onto Hybond™ N+ filters (Amersham) using a 96-pin replicating device such that each filter had 384 products present in duplicate. The DNA was subjected to alkali denaturation by standard methods and fixed by baking at 80° C. for 2 hours. Individual inserts derived from the library were radiolabeled by random hexamer priming and used as probes against the three libraries (6 filters per probe). Hybridization was carried out overnight at 42° C. in buffer containing 50% formamide as described in Sambrook et al. The following day, the filters were washed in 2×standard saline citrate (SSC), 0.1% SDS at room temperature for minutes, followed by 2 washes in 0.1×X SSC, 0.1% SDS at 65° C. for 45 minutes each. The filters were then exposed to Kodak X-OMAT X-ray film overnight.

Results

Figure 2:
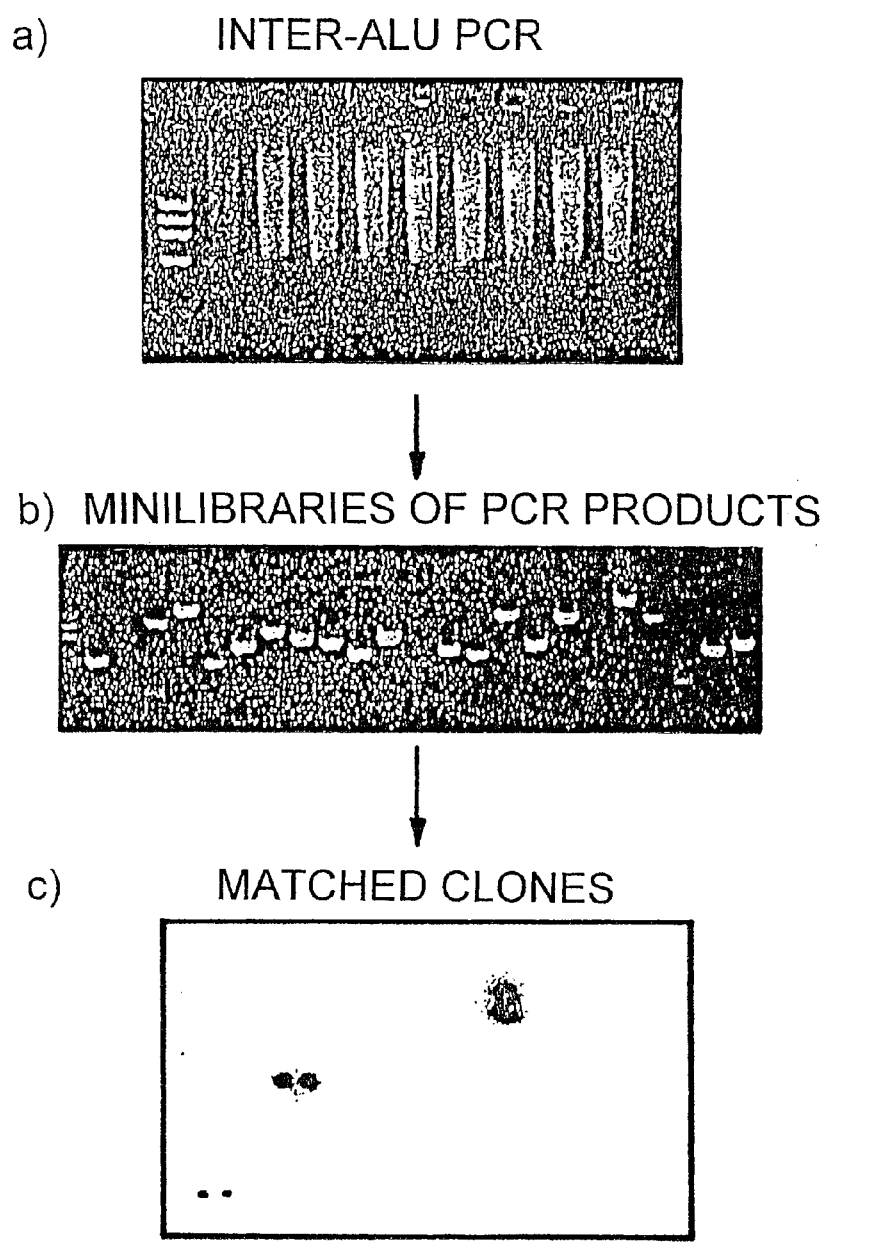
FIG. 2 shows data depicting the process of identifying a SNP: (a) depicts a gel in which inter-Alu PCR genomic DNA products prepared from the 8C primer (which has the nucleotide sequence SEQ ID NO:3) were separated; (b) depicts a gel in which inserts from the library clones were separated; and (c) depicts a filter having two positive or matched clones.

FIG. 2 shows the data obtained for identification of SNPs. The results of the gel electrophoresis of inter-Alu PCR genomic DNA products prepared using the 8C primer is shown in FIG. 2A. Mini libraries were prepared from the Alu PCR genomic DNA products. Colonies were picked from the libraries, and inserts were amplified. The inserts were separated by gel electrophoresis to demonstrate that each was a single insert. The gel is shown in FIG. 2B. Once the individual amplified inserts were spotted on Hybond™ N+ filters, the inserts were radiolabeled by random hexamer primary and used as probes of the entire contents against the three mini libraries. One of the filters, having 2 positive or matched clones, is shown in FIG. 2C.

The results of screening 330 base pairs of genomic DNA by the matched clone method led to the identification of 6 SNPs, 4 in single copy DNA, 2 in the flanking Alu sequence. These observations were consistent with the projected rate of SNP currents of 1 high frequency SNP per 1,000 base pairs or less. The single copy SNPs identified are presented below in Table I.

TABLE 1

| CEPH Individual | 1 | 2 | 3 | 4 |
|---|---|---|---|---|
| 201 | taagtGtacaa (SEQ ID NO. 5) | cccacGgagaa (SEQ ID NO. 7) | aattgCttccc (SEQ ID NO. 9) | aaattcaatgt (SEQ ID NO. 11) |
| | taagtGtacaa (SEQ ID NO. 5) | cccacGgagaa (SEQ ID NO. 7) | aattgCttccc (SEQ ID NO. 9) | aaattCaatgt.. (SEQ ID NO. 11) |

TABLE 1-continued

| CEPH Individual | 1 | 2 | 3 | 4 |
|---|---|---|---|---|
| 1701 | taagtAtacaa (SEQ ID NO. 6) | cccacAgagaa (SEQ ID NO. 8) | aattgCttccc (SEQ ID NO. 9) | aaattcaatgt.. (SEQ ID NO. 11) |
|  | taagtGtacaa (SEQ ID NO. 5) | cccacGgagaa (SEQ ID NO. 7) | aattgTttccc (SEQ ID NO. 10) | aaattCaatgt.. (SEQ ID NO. 11) |
| 2301 | taagtGtacaa (SEQ ID NO. 5) | cccacAgagaa (SEQ ID NO. 8) | aattgCttccc (SEQ ID NO. 9) | aaattAaatgt.. (SEQ ID NO. 12) |
|  | taagtGtacaa (SEQ ID NO. 5) | cccacGgagaa (SEQ ID NO. 7) | aattgTttccc (SEQ ID NO. 10) | aaattCaatgt.. (SEQ ID NO. 11) |

To verify the identities of the SNPs shown in Table I, specific primers were synthesized which permitted amplification of each single copy locus. Cycle sequencing was then performed on PCR products from each of the three unrelated individuals, and the site of the putative SNP was examined. In all cases, the genotype of the individual derived by cycle sequencing was consistent with the genotype observed in the matched clone set.

Example 2

Allele-specific Oligonucleotide Hybridization to Alu PCR SNPs

Methods

Inter-Alu PCR was performed using genomic DNA obtained from 136 members of 8 CEPH families (numbers 102, 884, 1331, 1332, 1347, 1362, 1413, and 1416) using the 8C Alu primer, as described above. The products from these reactions were denatured by alkali treatment (10-fold addition of 0.5 M NaOH, 2.0 M NaCl, 25 mM EDTA) and dot blotted onto multiple Hybond™ N+ filters (Amersham) using a 96-well dot blot apparatus (Schleicher and Schull). For each SNP, a set of two allele-specific oligonucleotides consisting of two 17-residue oligonucleotides centered on the polymorphic nucleotide residue were synthesized. Each filter was hybridized with 1 picomole $^{32}$P-kinase labeled allele-specific oligonucleotides and a 50-fold excess of non-labeled competitor oligonucleotide complementary to the opposite allele (Shuber et al., 1993). Hybridizations were carried out overnight at 52° C. in 10 mL TMAC buffer 3.0 M TMAC, 0.6% SDS, 1 mM EDTA, 10 mM NaPO$_4$, pH 6.8, 5×Denhardt's solution, 40 micrograms/milliliter yeast RNA). Blots were washed for 20 minutes at room temperature in TMAC wash buffer (3 M TMAC, 0.6% SDS, 1 mM EDTA, 10 mM Na$_3$PO$_4$ pH 6.8) followed by minutes at 52° C. (52° C.-52° C. is optimal). The blots were then exposed to Kodak X OMAT AR X-ray film for 8–24 hours and genotypes were determined by the hybridization pattern.

Results

Figure 3:
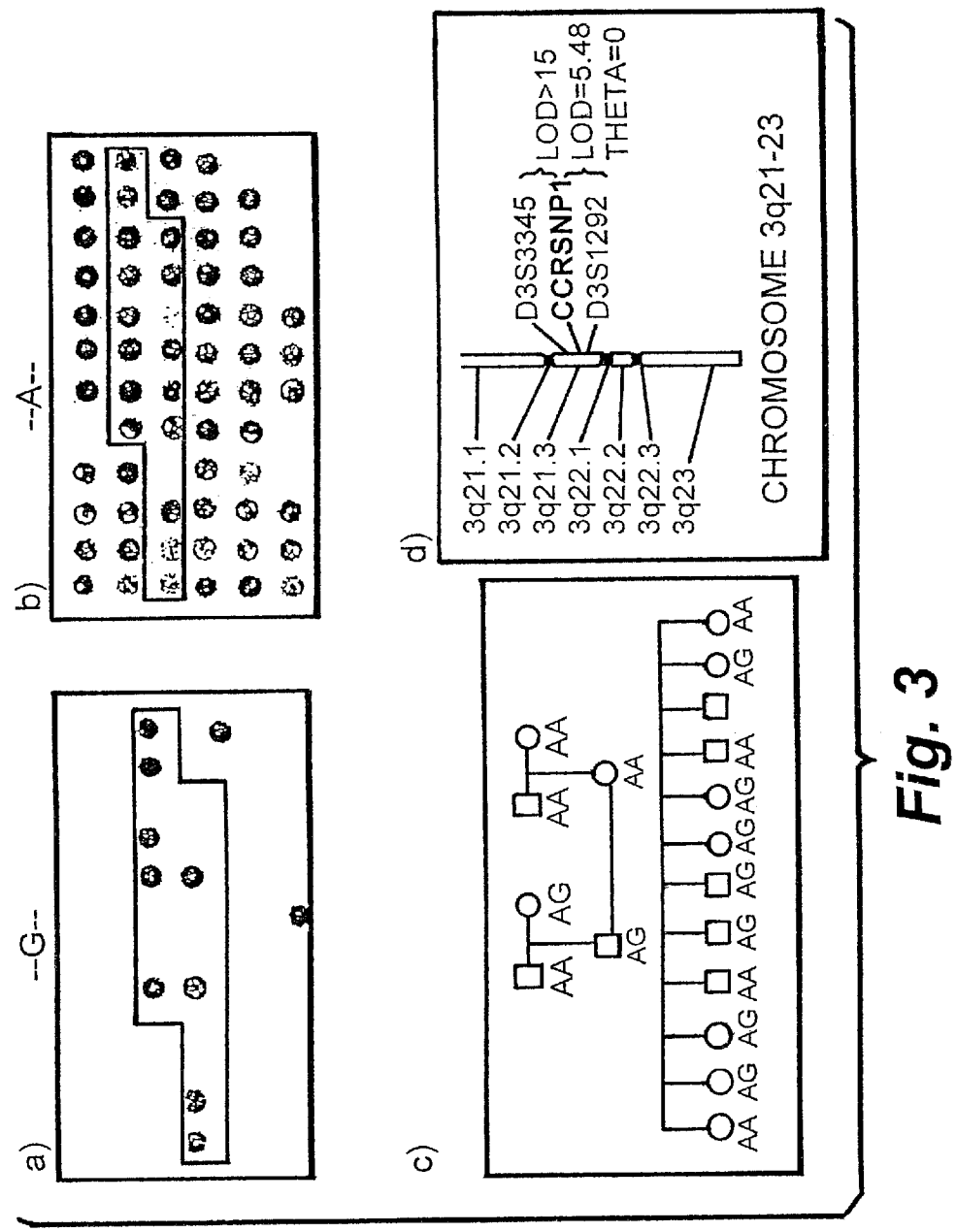
FIG. 3 depicts the results of a genotyping and mapping experiment: (a) depicts hybridization results obtained using G allele ASO; (b) depicts hybridization results obtained using A allele ASO; (c) is a pedigree of CEPH family #884 with genotypes indicted from (a) and (b); and (d) is a map of chromosome 3q21-23.

The results of the genotyping and mapping are shown in FIG. 3. In order to determine the map location of the SNP, the genotype data determined from CEPH families number 884 and 1347 were compared to the CEPH genotype database version 8.1 (HTTP:\\www.cephb.fr/cephdb/) by calculating a 2 point lod score using the computer software program MultiMap version 2.0 running on a Sparc Ultra I computer. This analysis revealed a linkage to marker D3S1292 with a lod score of 5.419 at a theta value of 0.0. To confirm this location, PCR amplification of the CCRSNP1 marker was performed on the Gene Bridge 4 radiation hybrid panel (Research Genetics). This analysis placed marker CCRSNP1 at 4.40 cR from D3S3445 with a lod score greater than 15.0. Integrated maps from the genetic location database (Collins et al., 1996) indicated that the locations of the markers identified by these two independent methods are overlapping. These results support the mapping of even low frequency polymorphisms by two point linkage to markers previously established on CEPH families.

Of the dot blots performed on each CEPH family PCR, two families were informative at this SNP locus, namely families number, 884 and 1347. The dot blot is shown in FIG. 3A. Lines are drawn around signals representing CEPH family 884 on the dot blot shown in FIGS. 3A and 3B. Allele-specific oligonucleotide hybridizations were performed on the filters shown in FIGS. 3A and 3B under TMAC buffer conditions with G allele-specific oligonucleotide (FIG. 3A) and A allele-specific oligonucleotide (FIG. 3B). The pedigree of CEPH family number 884 with genotypes as scored from the filter shown in FIGS. 3A and 3B is shown in FIG. 3C. The DNA was not available for one individual in this pedigree, and that square is left blank. Mapping of CCRSNP1 was performed by two independent methods. First, genotype data from informative CEPH families numbers 884 and 1347 were compared to the CEPH genotype database version 8.1 by calculation of a 2 point lod score. Secondly, PCR amplification of the CCRSNP1 marker was performed on the Gene Bridge 4 radiation hybrid panel. The highest lod scores determined by these analyses were D3S1292 and D3S3445, respectively, as shown in FIG. 3D.

The percentage of SNPs detected using the above-described methods is dependent on the number of chromosomes sampled, as well as the allele frequency.

Example 3

Confirmation of SNP Identity

Allele-specific oligonucleotides are synthesized based on standard protocols (Shuber et al., 1997). Briefly, polynucleotides of 17 bases centering on the polymorphic site are synthesized for each allele of a SNP. Hybridization with DNA dots of IRS or DOP-PCR products affixed to a membrane were performed, followed by hybridization to end labeled allele-specific oligonucleotides under TMAC buffer conditions. These conditions are known to equalize the contribution of AT and GC base pairs to melting temperature, thereby providing a uniform temperature for hybridization of allele-specific oligonucleotides independent of nucleotide composition.

Using this methodology, genotypes of CEPH progenitors and their offspring are determined. The Mendelian segregation of each SNP marker confirms its identity as a SNP marker and accrued estimate of its relative allele frequency, hence, its likely usefulness as a genetic marker. Markers which yield complex segregation patterns or show very low allele frequencies on CEPH progenitors are set aside for future analysis, and remaining markers are further characterized.

Example 4

Development of Detailed Information on Map Position and Allele Frequency for Each SNP Two complementary methods are used to establish genetic map position for each marker. Each marker is genotyped on a number of CEPH families. The result is compared, using MultiMap (Matise et al., 1993, as described above) or other appropriate software, against the CEPH database to determine by linkage the most likely position of the SNP marker.

Allele frequencies are determined by hybridization with the standard worldwide panel which U.S. NIH currently is making available to researchers for standardization of allele frequency comparison. Allele-specific oligonucleotide methodology used for genetic mapping is used to determine allele frequency.

Example 5

Development of a System for Scoring Genotype Using SNPs

After the identification of a set of SNPs, automated genotyping is performed. Genomic DNA of a well-characterized set of subjects, such as the CEPH families, is PCR-amplified using appropriate primers. These DNA samples serve as the substrate for system development. The DNA is spotted onto multiple glass slides for genotyping. This process can be carried out using a microarray spotting apparatus which can spot greater than 1,000 samples within a square centimeter area or more than 10,000 samples on a typical microscope slide. Each slide is hybridized with a fluorescently tagged allele-specific oligonucleotide under TMAC conditions analogous to those described above. The genotype of each individual is determined by the presence or absence of a signal for a selected set of allele-specific oligonucleotides. A schematic of the method is shown in FIG. 4.

PCR products are attached to the slide using any methods for attaching DNA to a surface that are known in the art. For instance, PCR products may be spotted onto poly-L-lysine-coated glass slides, and crosslinked by UV irradiation prior to hybridization. A second, more preferred method, which has been developed according to the invention, involves use of oligonucleotides having a 5' amino group for each of the PCR reactions described above. The PCR products are spotted onto silane-coated slides in the presence of NaOH to covalently attach the products to the slide. This method is advantageous because a covalent bond is formed, which produces a stable attachment to the surface.

SNP-ASO are hybridized under TMAC hybridization conditions with the RCGs covalently conjugated to the surface. The allele-specific oligonucleotides are labeled at their 5'-ends with a fluorescent dye, (e.g., Cy3). After washing, detection of the fluorescent oligonucleotides is performed in one of two ways. Fluorescent images can be captured using a fluorescence microscope equipped with a CCD camera and automated stage capabilities. Alternatively, the data can be obtained using a microarray scanner (e.g. one made by Genetic Microsystems). A microarray scanner provides image analysis which can be converted to a digital (e.g. +/−) signal for each sample using any of several available software applications (e.g., NIH image, ScanAnalyze, etc.). The high signal/noise ratio for this analysis allows for the determination of data in this mode to be straightforward and automated. These data, once exported, can be manipulated to conform with a format which can be analyzed by any of several human genetics applications such as CRI-MAP and LINKAGE software. Additionally, the methods may involve use of two or more fluorescent dyes or other labels which can be spectrally differentiated to reduce the number of samples which need to be analyzed. For instance, if four fluorescent spectrally distinct dyes, (e.g., ABI Prism dyes 6-FAM, HEX, NED, ROX) are used, then four hybridization reactions can be performed in a single hybridization mixture.

Example 6

Reduction of Genome Complexity Using IRS-PCR or DOP-PCR

The initial step of the SNP identification method and the genotyping approach described above is to reduce the complexity of genomic DNA in a reproducible manner. The purpose of this step with respect to genotyping is to allow genotyping of multiple SNPs using the products of a single PCR reaction. Using the IRS-PCR approach, a PCR primer was synthesized which bears homology to a repetitive sequence present within the genome of the species to be analyzed (e.g., Alu sequence in humans). When two repeat elements bearing the primer sequence are present in a head-to-head fashion within a limited distance (approximately 2 kilobase pairs), the inter-repeat sequence can be amplified. The method has the advantage that the complexity of the resultant PCR can be controlled by how closely the nucleotide sequence primer chosen is to the consensus nucleotide sequence of the repeat element (that is, the closer to the repeat consensus, the more complex the PCR product).

In detail, a 50 microliter reaction for each sample was set up as follows:

| | |
|---|---|
| distilled, deionized $H_2O$ (dd$H_2O$) | 30.75 |
| 10× PCR Buffer | 5 μl |
| (500 mM KCl, 100 mM Tris-HCl pH 8.3, 15 mM $MgCl_2$ μM, 0.1% gelatin) | |
| 1.25 mM dNTPs | 7.5 μl |
| 20 μm Primer 8C | 1.5 μl |
| Taq polymerase (1.25 units) | 0.25 μl |
| Template (50 ng genomic DNA in dd$H_2O$) | 5.0 μl |
| | 50 ul total |

The PCR reaction was performed, for example, in a Perkin Elmer 9600 thermal cycler under the following conditions:

| | |
|---|---|
| 1 min. | 94° C. |
| 30 sec. | 94° C. ⎫ |
| 45 sec. | 58° C. ⎬ 32 cycles |
| 90 sec. | 72° C. ⎭ |
| 10 min. | 72° C. |
| Hold | 4° C. |

An aliquot of the reaction mixture was separated on an agarose gel to confirm successful amplification.

RCGs were also performed using DOP-PCR with the following primer (CTC GAG NNN NNN AAG CGA TG) (SEQ ID NO: 4) (wherein N is any nucleotide). DOP-PCR uses a single primer which is typically composed of 3 parts, herein designated tag-$(N)_x$-TARGET. The TARGET portion is a polynucleotide which comprises at least 7, and preferably at least 8, arbitrarily-selected nucleotide residues, x is an integer from 0 to 9, and N is any nucleotide residue. Tag is a polynucleotide as described above.

The initial rounds of DOP-PCR were performed at a low temperature, because the specificity of the reaction is determined primarily by the nucleotide sequence of the TARGET portion and the $N_x$ residues. A slow ramp time during these cycles insures that the primers do not detach from the template prior to chain extension. Subsequent amplification rounds were carried out at a higher annealing temperature because of the fact that the 5' end of the DOP-PCR primer can also contribute to primer annealing.

The DOP-PCR method was performed using a reaction mixture comprising the following ingredients:

| | |
|---|---|
| distilled deionized H$_2$O | 24 µl |
| 10× PCR Buffer | 5 µl |
| 1.25 mM dNTPs | 8 µl |
| 20 µM Primer DOP-BJ1 (SEQ ID No. 4) | 7.5 µl |
| Taq polymerase (1.25 units) | 0.5 µl |
| Template | 5 µl |
| (50 ng genomic DNA in distilled deionized H$_2$O) | 50 µl |

The PCR reaction was performed, for example, in a Perkin Elmer 9600 thermal cycler using the following reaction conditions:

| | | |
|---|---|---|
| 1 min. | 94° C. | |
| 1 min. | 94° C. | |
| 1.5 min. | 45° C. | 5 cycles |
| 2 min. ramp to | 72° C. | |
| 3 min. | 72° C. | |
| 1 min. | 94° C. | |
| 1.5 min. | 58° C. | 35 cycles |
| 3 min. | 72° C. | |
| 10 min. | 72° C. | |
| Hold | 4° C. | |

Example 7

Attachment of PCR Products to a Solid Support

Once the complexity of the genomic DNA from an individual has been reduced, it can be attached to a solid support in order to facilitate hybridization analysis. One method of attaching DNA to a solid support involves spotting PCR products onto a nylon membrane. This protocol was performed as follows:

Upon completion of the PCR reaction (typically in a 50 µl reaction mixture), a 10-fold amount of denaturing solution (500 mM NaOH, 2.0 M NaCl, 25 mM EDTA) and a small amount (5 ul) of India Ink were added. Sixty microliters of product was applied to a pre-wetted Hybond™ N+ membrane (Amersham) using a Schleicher and Schull 96-well dot blot apparatus. The membrane was immediately removed and placed DNA side up on top of Whatmann 3MM paper saturated with 2×SSC for 2 minutes. The filters were air-dried and the DNA was fixed to the membrane by baking in an 80° C. oven for 2 hours. The membranes were then used for hybridization.

Another method for attaching nucleic acids to a support involves the use of microarrays. This method attaches minute quantities of PCR products samples onto a glass slide. The number of samples that can be spotted is greater than 1000/cm$^2$, and therefore over 10,000 samples can be analyzed simultaneously on a glass slide. To accomplish this, pre-cleaned glass slides were placed in a mixture of 80 ml dry xylene, 32 ml 96% 3-glycidoxy-propyltrimethoxy silane, and 160 µl 99% N-ethyldiisopropylamin at 80° C. overnight. The slides were rinsed for 5 minutes in ethylacetate and dried at 80° C. for 30 minutes. An equal volume of 0.8 M NaOH (0.6M NaOH and 0.6–0.8M KOH also works) was added directly to the PCR product (which contained a 5' amino group incorporated into the PCR primer) and the components were mixed. The resulting solution was spotted onto a glass slide under humid conditions. At the earliest opportunity, the slide was placed in a humid chamber overnight at 37° C. The next day, the slide was removed from the humid chamber and kept at 37° C. for an additional 1 hour. The slide was incubated in an 80° C. oven for 2.5 hours, and then washed for 5 minutes in 0.1% SDS. The slide was washed for an additional 5 minutes in ddH20 and air dried. Attachment to the slide was monitored by OilGreen staining (obtained from Molecular Probes), which specifically binds single-stranded DNA.

Example 8

Hybridization Using Allele Specific Oligonucleotides for Each SNP

In order to determine the genotype of an individual at a selected SNP locus, we employed allele-specific oligo hybridizations. Using this method, 2 hybridization reactions were performed at each locus. The first hybridization reaction involved a labeled (radioactive or fluorescent) SNP-ASO (typically 17 nucleotides residues) centered around and complementary to one allele of the SNP. To increase specificity, a 20 to 50-fold excess of non-labeled SNP-ASO complementary to the opposite allele of the SNP was included in the hybridization mixture. For the second hybridization, the allele specificity of the previously labeled and non-labeled SNP-ASOs was reversed. Hybridization occurred in the presence of TMAC buffer, which has the property that oligonucleotides of the same length have the same annealing temperature.

Specifically, for analysis of each SNP, a pair of SNP allele-specific oligos (SNP-ASOs) consisting of two 1 7mers centered around the polymorphic nucleotide were synthesized. Each filter was hybridized with 20 pmol $^{33}$P-labeled kinase labeled SNP-ASO (0.66 pmol/ml) and a 50-fold excess of non-labeled competitor oligonucleotide complementary to the other allele of the SNP. Hybridizations was performed overnight at 52° C. in 10 ml TMAC buffer (3.0M TMAC, 0.6% SDS, 1 mM EDTA, 10 mM NaPO$_4$ 6.8, 5×Denhardt's solution, 40 µg/ml yeast RNA). Blots were washed for 20 minutes at room temperature in TMAC Wash Buffer (3M TMAC, 0.6% SDS, 1 mM EDTA, 10 mM Na$_3$PO$_4$ pH 6.8) followed by 20 minutes washing at 52° C. The blots were exposed to Kodak X-OMATAR X-ray film for 8–24 hours, and genotypes were determined by analyzing the hybridization pattern.

Example 9

Scoring the Hybridization Pattern for Each Sample to Determine Genotype

Hybridization of SNP-ASOs (2 for each locus) to with IRS-PCR or DOP-PCR products of several individuals has been performed. The final step in this process is to determine if a positive or negative signal exists for each hybridization for an individual and then, based on this information, determine the genotype for that particular locus. Essentially, all of the detection methods described herein can be reduced to a digital image file, for example using a microarray reader or using a phosphoimager. Presently, there are several software products which will overlay a grid onto the image and determine the signal strength value at each element of the grid. These values are imported into a spreadsheet program, like Microsoft Excel™, and simple analysis is performed to assign each signal a + or − value. Once this is accomplished, an individual's genotype can be determined by its pattern of hybridization to the SNP alleles present at a given loci.

Example 10

Genomic Analysis Using DOP-PCR

Genomic DNA isolated from approximately 40 individuals was subjected to DOP-PCR using primer BJ1 (CTC GAG NNN NNN AAG CGA TG) (SEQ ID NO: 4). 100 microliter of the DOP-PCR mixture was precipitated by addition of 10 microliters 3M sodium acetate (pH 5.2) and 110 microliters of isopropanol and were stored at −20° C. for at least 1 hour. The samples were spun down in a microcentrifuge for 30 minutes and the supernatant was removed. The pellets were rinsed with 70% ethanol and spun again for 30 minutes. The supernatant was removed and the pellets were air-dried overnight at room temperature.

Figure 8:
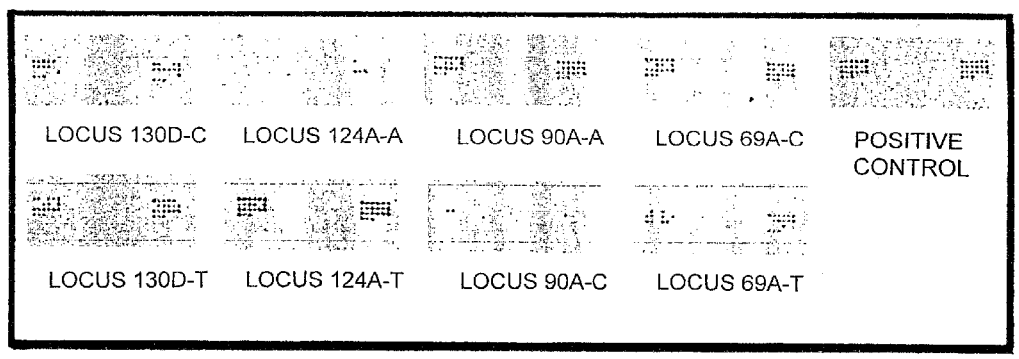
FIG. 8 depicts results obtained from a hybridization reaction involving RCGs prepared by DOP-PCR and SNP-ASOs immobilized on a surface in a microarray format.

The pellets were then resuspended in 12 microliters of distilled water and stored at −20° C. until denatured by the addition of 3 microliter of 2N NaOH/50 mM EDTA and maintained at 37° C. for 20 minutes and then at room temperature for 15 minutes. The samples were then spotted onto nylon coated-glass slides using a Genetic Microsystems GMS417 microarrayer. Upon completion of the spotting, the slides were placed in an 80° C. vacuum oven for 2 hours, and then stored at room temperature. A set of 2 allele specific SNP-ASOs consisting of two 17mers centered around a polymorphic nucleotide residue were synthesized. Each slide was prehybridized for 1 hour in Hyb Buffer (3M TMAC/0.5% SDS/1 mM EDTA/10 mM NaPO$_4$/5× Denhardt's solution/40 µg/ml yeast RNA) followed by hybridization with 0.66 picomoles per milliliter $^{33}$P-labeled kinase labeled SNP-ASO and a 50-fold excess of cold-competitor SNP-ASO of the opposite allele in Hyb Buffer. Hybridizations were carried out overnight at 52° C. The slides were washed twice for 30 minutes at room temperature in TMAC Wash Buffer (3M TMAC, 0.6% SDS, 1 mM EDTA, 10 mM NaPO$_4$ pH 6.8) followed by 20 minutes at 54° C. The slides were exposed to Kodak BioMax MR X-ray film. The results are shown in FIG. 8. The genotypes were determined by the hybridization patterns shown in FIG. 8 wherein loci are indicated.

The foregoing written specification is considered to be sufficient to enable one skilled in the art to practice the invention. The present invention is not limited in scope by the examples provided, since the examples are intended as illustrations of various aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for detecting the presence or absence of a single nucteotide polymorphism (SNP) allele in a genomic DNA sample, the method comprising:
preparing a reduced complexity genome (RCG) from the genomic DNA sample, wherein the RCG is a randomly primed PCR-derived RCG, and
analyzing the RCG for the presence or absence of a SNP allele.

2. The method of claim 1, wherein the analysis comprises hybridizing a SNP-ASO and the RCG, wherein the SNP-ASO is complementary to one allele of a SNP, with the RCG, and wherein the presence or absence of the SNP is used to characterize the genomic DNA sample.

3. The method of claim 2, wherein the RCG is immobilized on a surface.

4. The method of claim 2, wherein the SNP-ASO is immobilized on a surface.

5. The method of claim 4, wherein a plurality of different SNP-ASOs are attached to the surface.

6. The method of claim 2, wherein the SNP-ASO is individually hybridized with a plurality of RCGs.

7. The method of claim 2, wherein the SNP-ASO is a plurality of SNP ASOs, at least a fraction which are labeled.

8. The method of claim 7, wherein an excess of a non-labeled SNP-ASO is added during the hybridization step, wherein the non-labeled oligonucleotide is complementary to a different allele of the same SNP than the labeled SNP-ASO.

9. The method of claim 7, further comprising performing a parallel hybridization reaction wherein the RCG is hybridized with a labeled SNP-ASO, wherein the oligonucleotide is complementary to a different allele of the same SNP than the labeled SNP-ASO.

10. The method of claim 9, wherein the two SNP-ASOs are distinguishably labeled.

11. The method of claim 7, an excess of non-labeled SNP-ASO is present during the hybridization.

12. The method of claim 7, wherein the label is a radioactive isotope.

13. The method of claim 12, further comprising the step of exposing the RCG to a film to produce a signal on the film which corresponds to the radioactively labeled hybridization products if the SNP is present in the RCG.

14. The method of claim 7, wherein the label is a fluorescent molecule.

15. The method of claim 14, further comprising the step of exposing the RCG to an automated fluorescence reader to generate an output signal which corresponds to the fluorescently labeled hybridization products if the SNP is present in the RCG.

16. The method of claim 7, wherein the plurality of SNP-ASOs are labeled with fluorescent molecules, each SNP-ASO of a particular sequence being labeled with a spectrally distinct fluorescent molecule from a SNP-ASO having a different sequence.

17. The method of claim 16, wherein the number of SNP-ASOs having a spectrally distinct fluorescent molecule is at least two.

18. The method of claim 16, wherein the number is selected from the group consisting of three, four and eight.

19. The method of claim 2, wherein a plurality of RCGs are labeled with fluorescent molecules, each RCG being labeled with a spectrally distinct fluorescent molecule, and wherein all of the RCGs having a spectrally distinct fluorescent molecule.

20. The method of claim 2, wherein the SNP-ASO is composed of from about 10 to about 50 nucleotide residues.

21. The method of claim 20, wherein the SNP-ASO is composed of from about 10 to about 25 nucleotide residues.

22. The method of claim 2, wherein the RCG is labeled.

23. The method of claim 2, wherein the genomic DNA sample is characterized by generating a genomic pattern based on the presence or absence of the allele of the SNP in the genomic DNA sample.

24. The method of claim 23, wherein the genomic pattern is a genomic classification code.

25. The method of claim 1, wherein the method further comprises identifying a genotype of the genomic DNA sample, whereby the genotype is identified by the presence or absence of the allele of the SNP in the RCG.

26. The method of claim 25, wherein the presence or absence of the SNP allele is analyzed in a plurality of genomic DNA samples selected randomly from a population, the method further comprising determining the allele frequency of the SNP allele in the population by comparing the number of genomic DNA samples in which the allele is detected and the number of genomic DNA samples analyzed.

27. The method of claim 1, wherein the genomic DNA sample is obtained from a tumor.

28. The method of claim 27, wherein a plurality of RCGs are prepared from genomic DNA samples isolated from a plurality of subjects and the plurality of RCGs are analyzed for the presence of the SNP.

29. The method of claim 1, wherein the RCG is prepared by performing degenerate oligonucleotide priming-polymerase chain reaction (DOP-PCR) using a degenerate oligonucleotide primer having a tag-$(N)_x$-TARGET nucleotide sequence, wherein the TARGET nucleotide sequence includes at least 7 TARGET nucleotide residues, wherein x is an integer from 0–9, and wherein each N is any nucleotide residue, and wherein the tag is a polynucleotide having from about 0 to about 20 nucleotides.

30. The method of claim 29, wherein the TARGET nucleotide sequence includes at least 8 nucleotide residues.

31. The method of claim 1, wherein the RCG is prepared by interspersed repeat sequence-polymerase chain reaction (IRS-PCR).

32. The method of claim 1, wherein the RCG is prepared by arbitrarily primed-polymerase chain reaction (AP-PCR).

33. The method of claim 1, wherein the RCG is prepared by adapter-polymerase chain reaction.

34. The method of claim 1, wherein the RCG is prepared by performing degenerate oligonucleotide priming-polymerase chain reaction using a degenerate oligonucleotide primer having a tag-$(N)_x$-TARGET nucleotide sequence, wherein the TARGET nucleotide sequence includes fewer than 7 TARGET nucleotide residues wherein x is an integer from 0 to 9, wherein each N is any nucleotide residues, and wherein the tag is a polynucleotide having from about 0–20 nucleotides.

35. The method of claim 34 wherein the TARGET nucleotide sequence includes at least 5 nucleotide residues.

36. The method of claim 34 wherein the TARGET nucleotide sequence includes at least 6 nucleotide residues.

37. The method of claim 1, wherein the RCG is prepared by performing multiple primed OP-PCR.

38. The method of claim 1, wherein the complexity of the genomic is reduced by 50%.

39. The method of claim 1, wherein the complexity of the genomic is reduced by 95%.

40. The method of claim 1, wherein the complexity of the genomic is reduced by 99%.

* * * * *

UNITED STATES PATENT AND TRADEMARK OFFICE
CERTIFICATE OF CORRECTION

PATENT NO. : 6,703,228 B1
DATED : March 9, 2004
INVENTOR(S) : Landers et al.

It is certified that error appears in the above-identified patent and that said Letters Patent is hereby corrected as shown below:

Column 19,
Line 53, please replace "DOP-PCW" with -- DOP-PCR --.

Column 241,
Line 12, please replace "nucteotide" with -- nucleotide --.
Line 17, please insert -- directly by hybridization -- after "RCG".
Line 21, please insert -- whereby the allele of the SNP is present in the genomic DNA sample if the SNP-ASO hybridizes -- after "SNP".
Line 22, please insert -- allele -- after "SNP".

Column 244,
Lines 6, 8 and 10, please replace "genomic" with -- genome --.

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,703,228 B1
APPLICATION NO. : 09/404912
DATED : March 9, 2004
INVENTOR(S) : John Landers et al.

Page 1 of 1

It is certified that error appears in the above-identified patent and that said Letters Patent is hereby corrected as shown below:

Col. 1, line 11, should read:

This invention was made with government support under grant number R01 HG000299 awarded by the NIH. The government has certain rights in the invention.

Signed and Sealed this
Twenty-first Day of June, 2011

David J. Kappos
*Director of the United States Patent and Trademark Office*